US006761758B2

(12) United States Patent
Boils-Boissier et al.

(10) Patent No.: US 6,761,758 B2
(45) Date of Patent: Jul. 13, 2004

(54) ALKYLATED TETRAKIS (TRIAMINOTRIAZINE) COMPOUNDS AND PHASE CHANGE INKS CONTAINING SAME

(75) Inventors: Danielle C. Boils-Boissier, Mississauga (CA); Marcel P. Breton, Mississauga (CA); Jule W. Thomas, Jr., West Linn, OR (US); Donald R. Titterington, Newberg, OR (US); Jeffrey H. Banning, Hillsboro, OR (US); H. Bruce Goodbrand, Hamilton (CA); James D. Wuest, Montreal (CA); Marie-Eve Perron, Les Cedres (CA); Francis Monchamp, Montreal (CA); Hugues Duval, Montreal (CA)

(73) Assignee: Xerox Corporation, Stamford, CT (US)

( * ) Notice: Subject to any disclaimer, the term of this patent is extended or adjusted under 35 U.S.C. 154(b) by 44 days.

(21) Appl. No.: 10/235,514

(22) Filed: Sep. 4, 2002

(65) Prior Publication Data

US 2004/0050295 A1 Mar. 18, 2004

(51) Int. Cl.$^7$ .......................... C09D 11/00; G01D 11/00; C07D 251/48; C07D 251/52; C07D 403/14
(52) U.S. Cl. ............................... 106/31.29; 106/31.61; 106/31.47; 106/31.77; 347/99; 544/197; 544/198; 544/208; 544/209; 544/211; 544/212
(58) Field of Search ......................... 106/31.29, 31.61, 106/31.47, 31.77; 347/99; 544/197, 198, 208, 209, 211, 212

(56) References Cited

U.S. PATENT DOCUMENTS

| | | | |
|---|---|---|---|
| 2,703,808 A | 3/1955 | Buchman | 260/456 |
| 3,653,932 A | 4/1972 | Berry et al. | 106/22 |
| 4,390,369 A | 6/1983 | Merritt et al. | 106/31 |
| 4,484,948 A | 11/1984 | Merritt et al. | 106/31 |
| 4,538,156 A | 8/1985 | Durkee et al. | 346/21 |
| 4,684,956 A | 8/1987 | Ball | 346/1.1 |
| 4,745,420 A | 5/1988 | Gerstenmaier | 346/140 |
| 4,790,961 A | 12/1988 | Weiss et al. | 260/376 |
| 4,851,045 A | 7/1989 | Taniguchi | 106/31 |
| 4,889,560 A | 12/1989 | Jaeger et al. | 106/27 |
| 4,889,761 A | 12/1989 | Titterington et al. | 428/195 |
| 5,006,170 A | 4/1991 | Schwarz et al. | 106/20 |
| 5,021,802 A | 6/1991 | Allred | 346/1.1 |
| 5,099,256 A | 3/1992 | Anderson | 346/1.1 |
| 5,122,187 A | 6/1992 | Schwarz et al. | 106/25 |
| 5,151,120 A | 9/1992 | You et al. | 106/27 |
| 5,180,425 A | 1/1993 | Matrick et al. | 106/22 |
| 5,195,430 A | 3/1993 | Rise | 100/168 |
| 5,221,335 A | 6/1993 | Williams et al. | 106/23 A |
| 5,298,618 A | 3/1994 | Speranza et al. | 540/454 |
| 5,372,852 A | 12/1994 | Titterington et al. | 427/288 |
| 5,389,958 A | 2/1995 | Bui et al. | 347/103 |
| 5,462,591 A | 10/1995 | Karandikar et al. | 106/20 |
| 5,476,540 A | 12/1995 | Shields et al. | 106/20 |
| 5,496,879 A | 3/1996 | Griebel et al. | 524/320 |
| 5,531,817 A | 7/1996 | Shields et al. | 106/22 |
| 5,554,212 A | 9/1996 | Bui et al. | 106/20 |
| 5,621,022 A | 4/1997 | Jaeger et al. | 523/161 |
| 5,761,597 A | 6/1998 | Smith et al. | 399/339 |
| 5,892,116 A | 4/1999 | Weiss et al. | 564/281 |
| 6,320,018 B1 | 11/2001 | Sijbesma et al. | 528/310 |

FOREIGN PATENT DOCUMENTS

| | | |
|---|---|---|
| CA | 941377 | 2/1974 |
| EP | 0 187 352 | 7/1986 |
| EP | 0 206 286 | 12/1986 |
| WO | WO 90/11283 | 10/1990 |
| WO | WO 94/04619 | 3/1994 |
| WO | WO 97/24364 | 7/1997 |

OTHER PUBLICATIONS

Marion Lescanne et al., "Flow–Induced Alignment of Fiber–like Supramolecular Self–Assemblies During Organogel Formation with Various Low Molecular Mass Organogelator—Solvent Systems," *Am. Chem. Soc.*, vol. 18, (2002), pp. 7151–7153, no month available.

G.M. Clavier et al., "Organogelators for Making Porous Sol–Gel Derived Silica at Two Different Length Scales," *J. Mater. Chem.*, (2000), 10, pp. 1725–1730, no month available.

Saleh A. Ahmed et al., "Multiaddressable Self–Assembling Organogelators Based on 2H–Chromene and N–Acyl–1, ω–amino Acid Units," *Am. Chem. Soc.*, (2002), 18, pp. 7096–7101, no month available.

Franz Alfred Neugebauer et al., "Tetrakis [4–(3–tert–butyl–5–phenylverdazyl–1–yl)phenyl]methan, in Tetraadikal," *Chem. Ber.*, (1976) 109, pp. 2389–2394 (not translated).

English abstract by SciFinder for Franz Alfred Neugebauer et al., "Tetrakis [4–(3–tert–butyl–5–phenylverdazyl–1–yl)phenyl]methan, in Tetraradikal," *Chem. Ber.*, (1976), 109 (7), pp. 2389–2394, no month available.

English Abstract of Japanese Patent Publication JP 62181279, Oct. 1987.

English abstract for Japanese Patent Publication JP 06157529, Jun. 1994.

English abstract for Japanese Patent Publication JP 3217541, Sep. 1991.

G. Clavier et al., "Remarkably Simple Small Organogelators: Di–n–alkoxy–benzene Derivatives," *Tetrahedron Letters*, 40, 9021–9024 (1999), no month available.

G. Mieden–Gundert et al., "Rational Design of Low Molecular Mass Organogelators: Toward a Library of Functional N–Acyl–1–ω–Amino Acid Derivatives," *Angew. Chem. Int. Ed.*, 40, No. 17, 3164–3166 (2001), no month available.

J–L. Pozzo et al., "Rational Design of New Acid–Sensitive Organogelators," *J. Mater. Chem.*, vol. 8, pp. 2575–2577 (1998), no month available.

J. T. Thurston et al., "Cyanuric Chloride Derivatives. I. Aminochloro–s–triazines," *J. Am. Chem. Soc.*, vol. 73, pp. 2981–3008 (1951), Jul.

Huckin et al., "Alkylation of Dianions of β–Keto Esters," *J. Am. Chem. Soc.*, vol. 96, pp. 1082–1087 (1974), no month available.

J–L. Pozzo et al., "Photochromic Guests in Organogels," *Mol. Cryst. Liq. Cryst.*, vol. 344, pp. 101–106 (2000), no month available.

Murata et al, "Thermal and Light Control of the Sol–Gel Phase Transition in Cholesterol–Based Organic Gels. Novel Helical Aggregation Modes as Detected by Circular Dichroism and Electron Microscopic Observation," *J. Am. Chem. Soc.*, vol. 116, No. 15, pp. 6664–6676 (1994), no month available.

Rabolt et al., *Macromolecules*, vol. 17, p. 2786 (1984), no month available.

L. Lu et al., "New lyotrophic Phases (thermally–reversible organogels) of simple tertiary amines and related tertiary and quaternary ammonium halide salts," *Chem. Commun.*, 1996, p. 2029, no month available.

B.L. Feringa et al., *J. Org. Chem.*, vol. 53, p. 1125 (1988), no month available.

U. Zehavi et al., :The Reactions of Carbobenzoxyamino Acid Amides with Carbonyl Compounds, *J. Org. Chem.*, vol. 26, pp. 1097–1101 (1961), no month available.

Tabushi et al., Lipophilic Diammonium Cation Having a Rigid Structure Complementary to Pyrophosphate Dianions of Nucleotides. Selective Extraction and Transport of Nucleotides, *J. Am. Chem. Soc.*, vol. 103, pp. 6152–6157 (1981), no month available.

R. Dagani, "Supramolecular Polymers," *Chemical and Engineering News*, p. 4 (Dec. 1997).

J.H.K. Hirschberg et al., "Supramolecular Polymers from Linear Telechelic Siloxanes with Quadruple–Hydrogen–Bonded Units," *Macromolecules*, vol. 32, p. 2696 (1999), no month available.

A.C. Griffin et al., "Design and Synthesis of 'Smart' Supramolecular Liquid Crystalline Polymers via Hydrogen–Bond Associations," *PMSE Proceedings*, vol. 72, p. 172 (1995), no month available.

Andrew J. Carr et al., "The Design of Organic Gelators: Solution and Solid State Properties of a Family of Bis–Ureas," *Tetrahedron Letters*, vol. 39, p. 7447 (1998), no month available.

Ronald F.M. Lange et al., "Hydrogen–Bonded Supramolecular Polymer Networks," *Journal of Polymer Science, Part A: Polymer Chemistry*, vol. 37, p. 3657 (1999), no month available.

Arno Kraft et al., "Combining Self–Assembly and Self–Association—Towards Columnar Supramolecular Structures in Solution and in Liquid–Crystalline Mesophase," *Polym. Mater. Sci. Eng.*, vol. 80, p. 18 (1999), no month available.

Y. Yuasa et al., "Facile Synthesis of β–Keto Esters from Methyl Acetoacetate and Acid Chloride: The Barium Oxide/Methanol System," *Organic Process Research and Development*, vol. 2, p. 412 (1998), no month available.

F. Hoogesteger et al., "Self–Complementary Hydrogen Bonding of 1,1'–Bicyclohexylidene–4,4'–dione Dioxime. Formation of a Non–Covalent Polymer," *Tetrahedron*, vol. 52, No. 5, p. 1773 (1996), no month available.

X. Wang et al., "Molecular Tectonics. Three–Dimensional Organic Networks with Zeolite Properties," *J. Am. Chem. Soc.*, vol. 116, p. 12119 (1994), no month available.

J. H. K. KY Hirschberg et al., "Helical Self–Assembled Polymers from Cooperative Stacking of Hydrogen–Bonded Pairs," *Nature*, vol. 407, p. 167 (2000), Sep.

Abdullah Zafar et al., "New Supramolecular Arrays based on Interactions between Carboxylate and Urea Groups: Solid–State and Solution Behavior," *New J. Chem.*, 1998, 137–141, no month available.

J–L. Pozzo et al., "The Unusual Molecular Organization of 2,3–Bis(n–hexyloxy)–anthracene in the Crystal, A Hint to the Origin of the Gelifying Properties of 2,3–Bis(n–alkyloxy)–anthracenes?", *J. Chem. Soc., Perkin Trans.*, 2, 824–826 (2001), no month available.

D. Abdallah et al., "The Quest for the Simplest Possible Organogelators and Some Properties of their Organogels," *J. Braz. Chem. Soc.*, vol. 11, No. 3, 209–218 (2000), no month available.

F. Placin et al., "Organogel Electrolytes Based on a Low Molecular Weight Gelator: 2,3–Bis(n–decyloxy)anthracene," *Chem. Mater.* 13, 117–121 (2001), no month available.

J. Jung et al., "Novel Vesicular Aggregates of Crown–Appended Cholesterol Derivatives Which Act as Gelators of Organic Solvents and as Templates for Silica Transcription," *J. Am. Chem. Soc.*, vol. 122, No. 36, 8648–8653 (2000), no month available.

D. Abdallah et al., "n–Alkanes Gel n–Alkanes (and Many Other Organic Liquids)," *Langmuir*, 16, 352–355 (2000), no month available.

P. Terech et al., "Low Molecular Mass Gelators of Organic Liquids and the Properties of their Gels," *Chem. Rev.*, 97, 3133–3159 (1997), no month available.

D. Abdallah et al., "Organogels and Low Molecular Mass Organic Gelators," *Adv. Mater.*, 12, No. 17, 1237 (2000), no month available.

F. Schoonbeek, "Making it All Stick Together: the Gelation of Organic Liquids by Small Organic Molecules," Doctoral Thesis, U. of Groningen, Netherlands, Apr. 2001.

Twieg et al., "Observations of a "Gel" Phase in Binary Mixtures of Semifluorinated n–Alkanes with Hydrocarbon Liquids," *Macromolecules*, vol. 18, p. 1361 (1985), no month available.

M.F. Shostakovskii et al., "Synthesis and Reactions of Polyhydric Alcohols I. Synthesis and Reactions of p–Toluenesulfonates of Polyhydric Alcohols," *Zhurnal Obshchei Khimii*, vol. 35, No. 5, p. 804–807 (1965), no month available.

J. Ashley et al., "The Chemotherapy of Schistosomiasis. Part I. Derivatives and Analogs of αω–Di(p–aminophenoxy)alkanes," *J. Chem. Soc.*, 1958, 3293, no month available.

Copending Application U.S. Ser. No. 09/949,315, filed Sep. 7, 2001, entitled "Aqueous Ink Compositions," by Thomas W. Smith et al.

Copending Application U.S. Ser. No. 09/948,958, filed Sep. 7, 2001, entitled "Phase Change Ink Compositions," by H. Bruce Goodbrand et al.

Copending Application U.S. Ser. No. (not yet assigned; Attorney Docket No. D/A2177), filed concurrently herewith, entitled "Alkylated Urea and Triaminotriazine Compounds and Phase Change Inks Containing Same," by Marcel P. Breton et al.

Copending Application U.S. Ser. No. (not yet assigned; Attorney Docket No. D/A2176), filed concurrently herewith, entitled "Guanidinopyrimidinone Compounds and Phase Change Inks Containing Same," by Danielle C. Boils–Boissier et al.

Copending Application U.S. Ser. No. (not yet assigned; Attorney Docket No. D/A2403), filed concurrently herewith, entitled "Phase Change Inks Containing Gelator Additives," by Marcel P. Breton et al.

English Abstract for German Patent Publication DE 4205713AL, Mar. 1993.

English Abstract for German Patent Publication DE 4205636, Aug. 1993.

R. P. Sijbesma et al., "Reversible Polymers Formed Self–Complementary Monomers Using Quadruple Hydrogen Bonding," *Science*, vol. 278, p. 1601 (1997), Nov.

J–L. Pozzo et al., *Tetrahedron*, vol. 53, No. 18, pp. 6377–6390 (1997), no month available.

Y.C. Lin et al., *Macromolecules*, vol. 20, p. 414 (1987), no month available.

A. Ikeda et al., *Rep. Asahi Glass Found. Ind. Technol.*, vol. 61, p. 115, (1992), no month available.

D.J. Abdallah et al., *Chem. Mater.*, vol. 11, p. 2907 (1999), no month available.

Ralston et al., *J. Org. Chem.*, vol. 9, p. 259 (1944), no month available.

*J. Prakt. Chem.*, vol. 327 (3), pp. 383–398 (1985), no month available.

J.C. Dejong et al., *Tetrahedron Lett.*, vol. 30, p. 7239 (1989), no month available.

J.C. DeJong, Ph.D. thesis, University of Groningen, The Netherlands, 1991, no month available.

J. March, *Advanced Organic Chemistry*, 4th Edition, pp. 903 and 1091–1092, Wiley Interscience (New York 1992), no month available.

J. Crossley Maxwell, *Aust. J. Chem.*, vol. 47, pp. 723–738 (1994), no month available.

T. Giorgi et al., "Gel–like lyomesophases formed in organic solvents by self–assembled guanine ribbons," *Chemistry—A European Journal* (2002), 8(9), 2143–2152, no month available.

T. Suyama et al., "A method for the preparation of substituted biguanides," *Nippon Kagaku Kaishi* (1989), (5), 884–7, no month available.

C.S. Snijder et al., *Chem. Eur. J.*, vol. 1, No. 9, pp. 594–597 (1995), no month available.

S. Senda et al., Gifu Coll. Pharm., Gifu, Japan, *Yakugaku Zasshi* (1969), 89 (2), 254–259, no month available.

B. Gluncic et al, *Acta Pharm. Jugosl.* (1986), 36(4), 393–404, no month available.

M. Klein, Recent Dev. Mass Spectrom. Biochem. Med., [Proc. Int. Symp.], 4th (1978), Meeting Date 1977, 1, 471–82, no month available.

T. Wada et al., "A New Boranophosphorylation Reaction for the Synthesis of Deoxyribonucleoside Boranophosphates," *Tetrahedron Letters*, vol. 43, No. 23, pp. 4137–4140 (2002), no month available.

R. Schirrmacher et al., "Dimethylpyridin–4–ylamine–catalysed alcoholysis of 2–amino–N,N,N–trimethyl–9H–purine–6–ylammonium chloride: An effective route to O6–substituted guanine derivatives from alcohols with poor nucleophilicity," *Synthesis*, vol. 4, pp. 538–542 (2002), no month available.

S. Bailey et al., "Synthesis and Antiviral Activity of 9–Alkoxypurines. New 9–(Hydroxyalkoxy) Derivatives of Guanine and 8–Methylguanine," *Antiviral Chem. Chemother.*, vol. 5, No. 1, pp. 21–33 (1994), no month available.

M. R. Harndenen et al., "Synthesis, Oral Bioavailability and In Vivo Activity of Acetal Derivatives of the Selective Antiherpesvirus Agent 9–(3–Hydroxypropoxy)Guanine (BRL44385)," *Antiviral Chem. Chemother.*, vol. 5, No. 3, pp. 147–154 (1994), no month available.

B. K. Bhattacharya et al., "Synthesis of Certain N–and C–alkyl Purine Analogs," *J. Heterocycl. Chem.*, vol. 30, No. 5, pp. 1341–1349 (1993), no month available.

*Primary Examiner*—Helene Klemanski
*Assistant Examiner*—Veronica F. Faison
(74) *Attorney, Agent, or Firm*—Judith L. Byorick

(57) ABSTRACT

Disclosed are compounds of the formulae

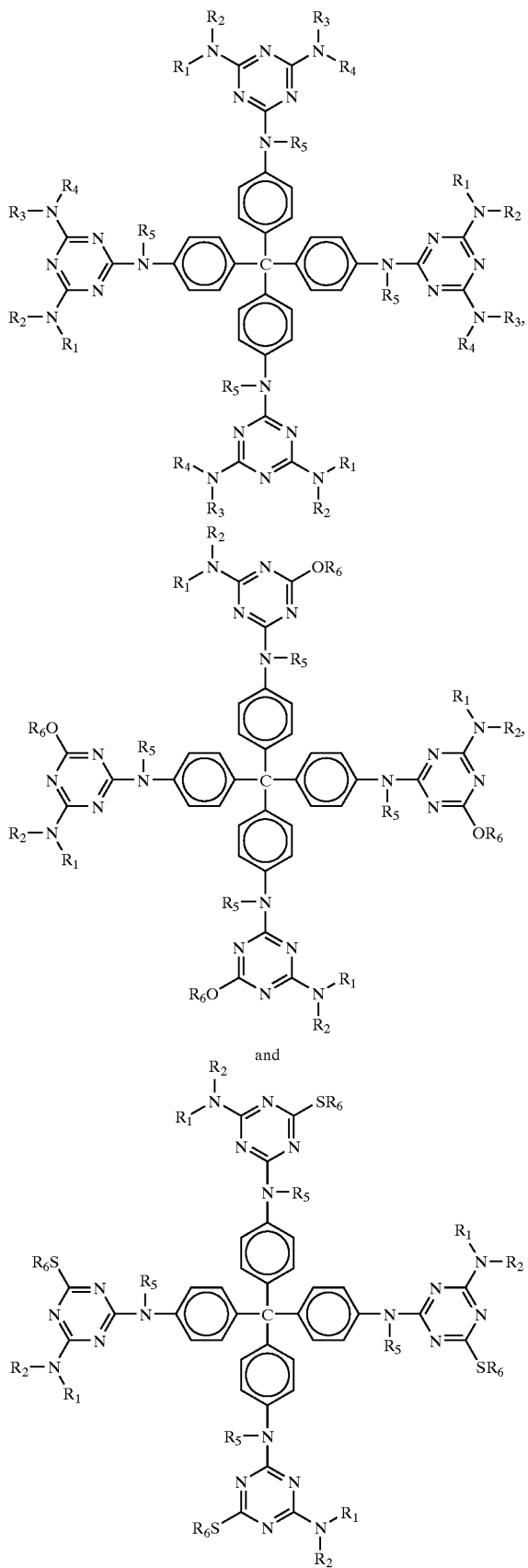

wherein, provided that at least one of $R_1$, $R_2$, $R_3$, $R_4$, $R_5$, and $R_6$ is a hydrogen atom, and provided that at least one of $R_1$, $R_2$, $R_3$, $R_4$, $R_5$, and $R_6$ is not a hydrogen atom, $R_1$, $R_2$, $R_3$, $R_4$, $R_5$, and $R_6$ each, independently of the others, is (i) a hydrogen atom, (ii) an alkyl group, (iii) an aryl group, (iv) an arylalkyl group, or (v) an alkylaryl group. Also disclosed are phase change ink compositions comprising a colorant and a phase change ink carrier comprising a material of this formula.

63 Claims, No Drawings

ALKYLATED TETRAKIS (TRIAMINOTRIAZINE) COMPOUNDS AND PHASE CHANGE INKS CONTAINING SAME

Cross-reference is made to the following applications:

Copending Application U.S. Ser. No. 09/949,315, filed Sep. 7, 2001, entitled "Aqueous Ink Compositions," with the named inventors Thomas W. Smith, David J. Luca, and Kathleen M. McGrane, the disclosure of which is totally incorporated herein by reference, discloses an aqueous ink composition comprising an aqueous liquid vehicle, a colorant, and an additive wherein, when the ink has been applied to a recording substrate in an image pattern and a substantial amount of the aqueous liquid vehicle has either evaporated from the ink image, hydrogen bonds of sufficient strength exist between the additive molecules so that the additive forms hydrogen-bonded oligomers or polymers.

Copending Application U.S. Ser. No. 09/948,958, filed Sep. 7, 2001, entitled "Phase Change Ink Compositions," with the named inventors H. Bruce Goodbrand, Thomas W. Smith, Dina Popovic, Daniel A. Foucher, and Kathleen M. McGrane, the disclosure of which is totally incorporated herein by reference, discloses a phase change ink composition comprising a colorant and an ink vehicle, the ink being a solid at temperatures less than about 50° C. and exhibiting a viscosity of no more than about 20 centipoise at a jetting temperature of no more than about 160° C., wherein at a first temperature hydrogen bonds of sufficient strength exist between the ink vehicle molecules so that the ink vehicle forms hydrogen-bonded dimers, oligomers, or polymers, and wherein at a second temperature which is higher than the first temperature the hydrogen bonds between the ink vehicle molecules are sufficiently broken that fewer hydrogen-bonded dimers, oligomers, or polymers are present in the ink at the second temperature than are present in the ink at the first temperature, so that the viscosity of the ink at the second temperature is lower than the viscosity of the ink at the first temperature.

Copending Application U.S. Ser. No. 10/235,061, filed concurrently herewith, entitled "Guanidinopyrimidinone Compounds and Phase Change Inks Containing Same," with the named inventors Danielle C. Boils-Boissier, Marcel P. Breton, Jule W. Thomas, Jr., Donald R. Titterington, Jeffery H. Banning, H. Bruce Goodbrand, James D. Wuest, Marie-Ève Perron, and Hugues Duval, the disclosure of which is totally incorporated herein by reference, discloses compounds of the formulae

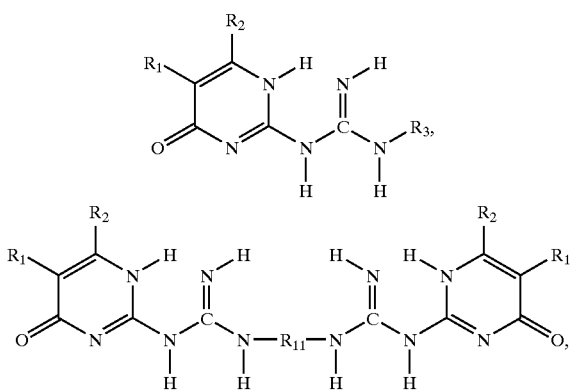

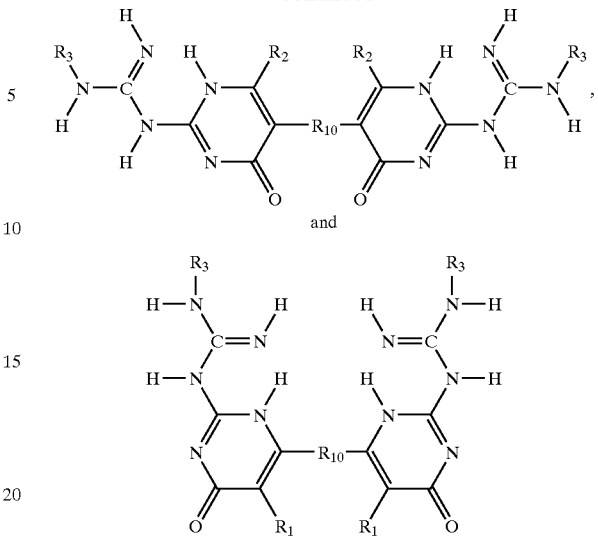

wherein, provided that at least one of $R_1$, $R_2$, and $R_3$ is not a hydrogen atom, $R_1$, $R_2$, and $R_3$ each, independently of the other, is (i) a hydrogen atom, (ii) an alkyl group, (iii) an aryl group, (iv) an arylalkyl group, or (v) an alkylaryl group, and wherein $R_1$ and $R_2$ can also be (vi) an alkoxy group, (vii) an aryloxy group, (viii) an arylalkyloxy group, (ix) an alkylaryloxy group, (x) a polyalkyleneoxy group, (xi) a polyaryleneoxy group, (xii) a polyarylalkyleneoxy group, (xiii) a polyalkylaryleneoxy group, (xiv) a silyl group, (xv) a siloxane group, (xvi) a polysilylene group, (xvii) a polysiloxane group, or (xviii) a group of the formula

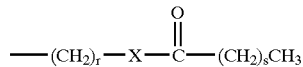

wherein r is an integer representing a number of repeat —$CH_2$— groups, wherein s is an integer representing a number of repeating —$CH_2$— groups, and wherein X is (a) a direct bond, (b) an oxygen atom, (c) a sulfur atom, (d) a group of the formula —$NR_{40}$— wherein $R_{40}$ is a hydrogen atom, an alkyl group, an aryl group, an arylalkyl group, or an alkylaryl group, or (e) a group of the formula —$CR_{50}R_{60}$— wherein $R_{50}$ and $R_{60}$ each, independently of the other, is a hydrogen atom, an alkyl group, an aryl group, an arylalkyl group, or an alkylaryl group, and $R_{10}$ and $R_{11}$ each, independently of the other, is (i) an alkylene group, (ii) an arylene group, (iii) an arylalkylene group, or (iv) an alkylarylene group, and wherein $R_{10}$ can also be (v) a polyalkyleneoxy group, (vi) a polyaryleneoxy group, (vii) a polyarylalkyleneoxy group, (viii) a polyalkylaryleneoxy group, (ix) a silylene group, (x) a siloxane group, (xi) a polysilylene group, or (xii) a polysiloxane group. Also disclosed are phase change ink compositions comprising a colorant and a phase change ink carrier comprising a material of this formula.

Copending Application U.S. Ser. No. 10/235,109, filed concurrently herewith, entitled "Alkylated Urea and Triaminotriazine Compounds and Phase Change Inks Containing Same," with the named inventors Marcel P. Breton, Danielle C. Boils-Boissier, Jule W. Thomas, Jr., Donald R. Titterington, H. Bruce Goodbrand, Jeffery H. Banning, James D. Wuest, Dominic Laliberté, and Marie-Ève Perron, the disclosure of which is totally incorporated herein by reference, discloses compounds of the formulae

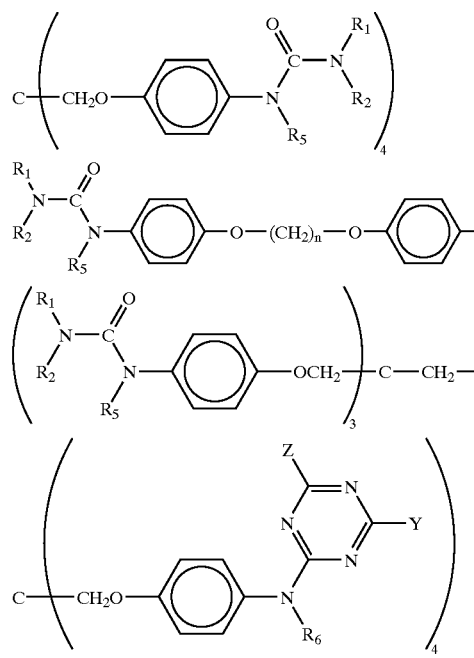

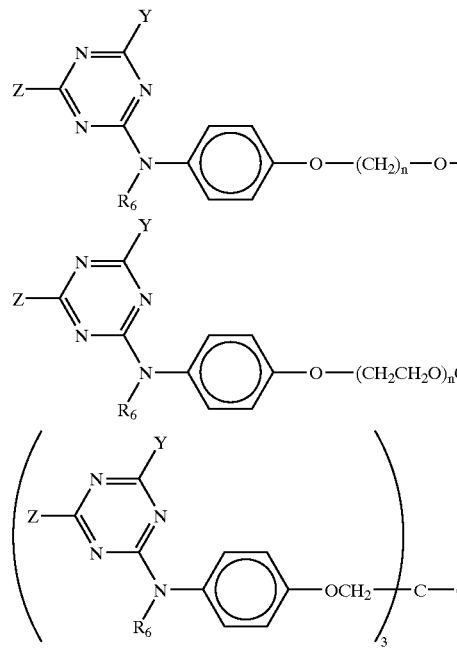

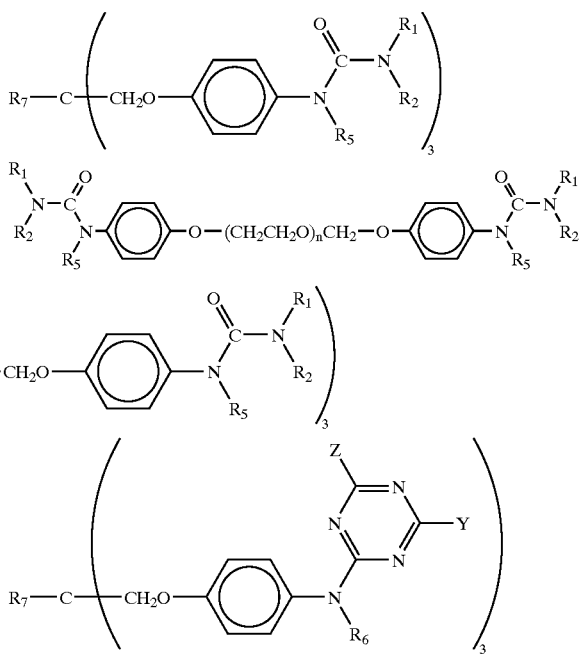

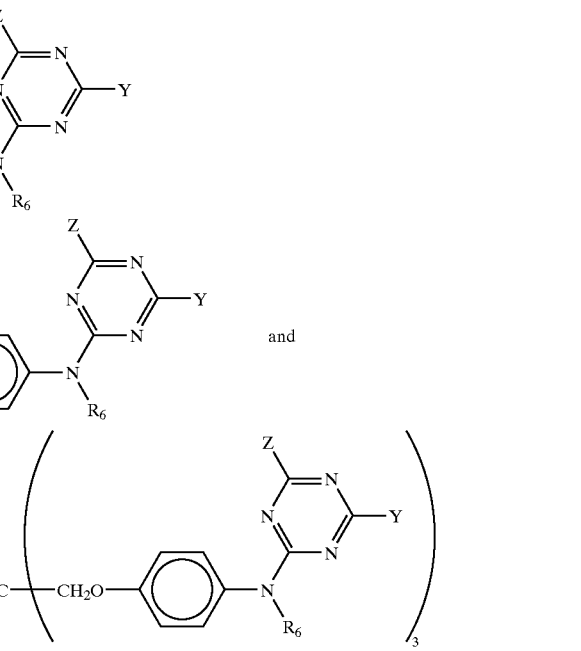

and

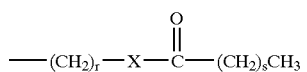

wherein Z is a group of the formula —$OR_1$, a group of the formula —$SR_1$, or a group of the formula —$NR_1R_2$, Y is a group of the formula —$OR_3$, a group of the formula —$SR_3$, or a group of the formula —$NR_3R_4$, n is an integer representing the number of repeat —($CH_2$)— or —($CH_2CH_2O$)— units, wherein, provided that at least one of $R_1$, $R_2$, $R_3$, $R_4$, $R_5$, and $R_6$ is a hydrogen atom, provided that at least one of $R_1$, $R_2$, $R_3$, $R_4$, $R_5$, and $R_6$ is other than a hydrogen atom, and provided that at least one Z or Y within the compound is a group of the formula —$NR_1R_2$ or a group of the formula —$NR_3R_4$, $R_1$, $R_2$, $R_3$, $R_4$, $R_5$, $R_6$, and $R_7$ each, independently of the others, is (i) a hydrogen atom, (ii) an alkyl group, (iii) an aryl group, (iv) an arylalkyl group, or (v) an alkylaryl group, and wherein $R_7$ can also be (vi) an alkoxy group, (vii) an aryloxy group, (viii) an arylalkyloxy group, (ix) an alkylaryloxy group, (x) a polyalkyleneoxy group, (xi) a polyaryleneoxy group, (xii) a polyarylalkyleneoxy group, (xiii) a polyalkylaryleneoxy group, (xiv) a silyl group, (xv) a siloxane group, (xvi) a polysilylene group, (xvii) a polysiloxane group, or (xviii) a group of the formula $$—(CH_2)_r—X—\overset{O}{\underset{\|}{C}}—(CH_2)_sCH_3$$

wherein r is an integer representing a number of repeat —$CH_2$— groups, wherein s is an integer representing a number of repeating —$CH_2$— groups, and wherein X is (a) a direct bond, (b) an oxygen atom, (c) a sulfur atom, (d) a group of the formula —NR$_{40}$— wherein R$_{40}$ is a hydrogen atom, an alkyl group, an aryl group, an arylalkyl group, or an alkylaryl group, or (e) a group of the formula —CR$_{50}$R$_{60}$— wherein R$_{50}$ and R$_{60}$ each, independently of the other, is a hydrogen atom, an alkyl group, an aryl group, an arylalkyl group, or an alkylaryl group, and wherein R$_6$ can also be

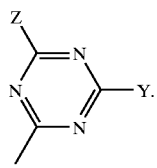

Also disclosed are phase change ink compositions comprising a colorant and a phase change ink carrier comprising a material of this formula.

Copending Application U.S. Ser. No. 10/235,125, filed concurrently herewith, entitled "Phase Change Inks Containing Gelator Additives," with the named inventors Marcel P. Breton, Danielle C. Boils-Boissier, Donald R. Titterington, Jule W. Thomas, Jr., Jeffery H. Banning, Christy Bedford, and James D. Wuest, the disclosure of which is totally incorporated herein by reference, discloses a phase change ink composition comprising an ink vehicle, a colorant, and a nonpolymeric organic gelator selected from the group consisting of anthracene-based compounds, steroid compounds, partially fluorinated high molecular weight alkanes, high molecular weight alkanes with exactly one hetero atom, chiral tartrate compounds, chiral butenolide-based compounds, bis-urea compounds, guanines, barbiturates, oxamide compounds, ureidopyrimidone compounds, and mixtures thereof, said organic gelator being present in the ink in an amount of no more than about 20 percent by weight of the ink, said ink having a melting point at or below which the ink is a solid, said ink having a gel point at or above which the ink is a liquid, and said ink exhibiting a gel state between the melting point and the gel point, said ink exhibiting reversible transitions between the solid state and the gel state upon heating and cooling, said ink exhibiting reversible transitions between the gel state and the liquid state upon heating and cooling, said melting point being greater than about 35° C., said gel point being greater than said melting point. Also disclosed are imaging processes employing phase change inks containing gelator additives.

BACKGROUND OF THE INVENTION

The present invention is directed to alkylated tetrakis (triaminotriazine) compounds and to phase change (hot melt) ink compositions. More specifically, the present invention is directed to compositions of matter and to phase change ink compositions suitable for use in ink jet printing processes that contain these compositions. One embodiment of the present invention is directed to compounds of the formulae

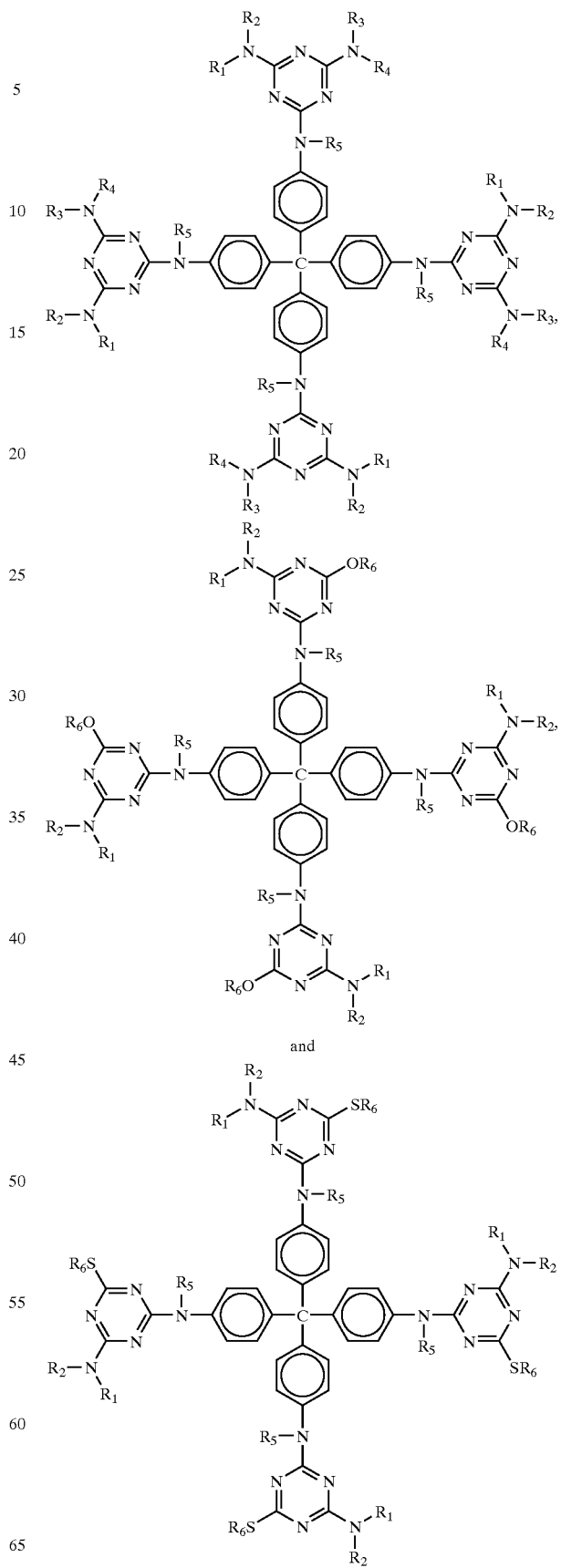

wherein, provided that at least one of $R_1$, $R_2$, $R_3$, $R_4$, $R_5$, and $R_6$ is a hydrogen atom, and provided that at least one of $R_1$, $R_2$, $R_3$, $R_4$, $R_5$, and $R_6$ is not a hydrogen atom, $R_1$, $R_2$, $R_3$, $R_4$, $R_5$, and $R_6$ each, independently of the others, is (i) a hydrogen atom, (ii) an alkyl group, (iii) an aryl group, (iv) an arylalkyl group, or (v) an alkylaryl group. Another embodiment of the present invention is directed to a phase change ink composition comprising a colorant and a phase change ink carrier comprising a material of this formula.

In general, phase change inks (sometimes referred to as "hot melt inks") are in the solid phase at ambient temperature, but exist in the liquid phase at the elevated operating temperature of an ink jet printing device. At the jet operating temperature, droplets of liquid ink are ejected from the printing device and, when the ink droplets contact the surface of the recording substrate, either directly or via an intermediate heated transfer belt or drum, they quickly solidify to form a predetermined pattern of solidified ink drops. Phase change inks have also been used in other printing technologies, such as gravure printing, as disclosed in, for example, U.S. Pat. No. 5,496,879 and German Patent Publications DE 4205636AL and DE 4205713AL, the disclosures of each of which are totally incorporated herein by reference.

Phase change inks for color printing typically comprise a phase change ink carrier composition which is combined with a phase change ink compatible colorant. In a specific embodiment, a series of colored phase change inks can be formed by combining ink carrier compositions with compatible subtractive primary colorants. The subtractive primary colored phase change inks can comprise four component dyes, namely, cyan, magenta, yellow and black, although the inks are not limited to these four colors. These subtractive primary colored inks can be formed by using a single dye or a mixture of dyes. For example, magenta can be obtained by using a mixture of Solvent Red Dyes or a composite black can be obtained by mixing several dyes. U.S. Pat. No. 4,889,560, U.S. Pat. No. 4,889,761, and U.S. Pat. No. 5,372,852, the disclosures of each of which are totally incorporated herein by reference, teach that the subtractive primary colorants employed can comprise dyes from the classes of Color Index (C.I.) Solvent Dyes, Disperse Dyes, modified Acid and Direct Dyes, and Basic Dyes. The colorants can also include pigments, as disclosed in, for example, U.S. Pat. No. 5,221,335, the disclosure of which is totally incorporated herein by reference. U.S. Pat. No. 5,621,022, the disclosure of which is totally incorporated herein by reference, discloses the use of a specific class of polymeric dyes in phase change ink compositions.

Phase change inks have also been used for applications such as postal marking and industrial marking and labelling.

Phase change inks are desirable for ink jet printers because they remain in a solid phase at room temperature during shipping, long term storage, and the like. In addition, the problems associated with noble clogging as a result of ink evaporation with liquid ink jet inks are largely eliminated, thereby improving the reliability of the ink jet printing. Further, in phase change ink jet printers wherein the ink droplets are applied directly onto the final recording substrate (for example, paper, transparency material, and the like), the droplets solidify immediately upon contact with the substrate, so that migration of ink along the printing medium is prevented and dot quality is improved.

Compositions suitable for use as phase change ink carrier compositions are known. Some representative examples of references disclosing such materials include U.S. Pat. No. 3,653,932, U.S. Pat. No. 4,390,369, U.S. Pat. No. 4,484,948, U.S. Pat. No. 4,684,956, U.S. Pat. No. 4,851,045, U.S. Pat. No. 4,889,560, U.S. Pat. No. 5,006,170, U.S. Pat. No. 5,151,120, U.S. Pat. No. 5,372,852, U.S. Pat. No. 5,496,879, European Patent Publication 0187352, European Patent Publication 0206286, German Patent Publication DE 4205636AL, German Patent Publication DE 4205713AL, and PCT Patent Application WO 94/04619, the disclosures of each of which are totally incorporated herein by reference. Suitable carrier materials can include paraffins, microcrystalline waxes, polyethylene waxes, ester waxes, fatty acids and other waxy materials, fatty amide containing materials, resinous materials, resinous materials made from different natural sources (tall oil rosins and rosin esters, for example), and many synthetic resins, oligomers, polymers, and copolymers.

U.S. Pat. No. 5,006,170 (Schwarz et al.) and U.S. Pat. No. 5,122,187 (Schwarz et al.), the disclosures of each of which are totally incorporated herein by reference, disclose hot melt ink compositions suitable for ink jet printing which comprise a colorant, a binder, and a propellant selected from the group consisting of hydrazine; cyclic amines; ureas; carboxylic acids; sulfonic acids; aldehydes; ketones; hydrocarbons; esters; phenols; amides; imides; halocarbons; urethanes; ethers; sulfones; sulfamides; sulfonamides; phosphites; phosphonates; phosphates; alkyl sulfines; alkyl acetates; and sulfur dioxide. Also disclosed are hot melt ink compositions suitable for ink jet printing which comprise a colorant, a propellant, and a binder selected from the group consisting of rosin esters; polyamides; dimer acid amides; fatty acid amides; epoxy resins; fluid paraffin waxes; fluid microcrystalline waxes; Fischer-Tropsch waxes; polyvinyl alcohol resins; polyols; cellulose esters; cellulose ethers; polyvinyl pyridine resins; fatty acids; fatty acid esters; poly sulfonamides; benzoate esters; long chain alcohols; phthalate plasticizers; citrate plasticizers; maleate plasticizers; sulfones; polyvinyl pyrrolidinone copolymers; polyvinyl pyrrolidone/polyvinyl acetate copolymers; novalac resins; natural product waxes; mixtures of linear primary alcohols and linear long chain amides; and mixtures of linear primary alcohols and fatty acid amides. In one embodiment, the binder comprises a liquid crystalline material.

U.S. Pat. No. 5,021,802 (Allred), the disclosure of which is totally incorporated herein by reference, discloses impulse ink or bubble jet inks which comprise 90 to 99.9 percent by weight of aqueous sol-gel medium and 0.1 to 10 percent by weight colorant. The inks are thermally reversible sol-gels which are gels at ambient temperatures and sols at temperatures between about 40 to 100° C.

U.S. Pat. No. 5,180,425 (Matrick et al.), the disclosure of which is totally incorporated herein by reference, discloses an ink for ink jet printers which comprises an aqueous carrier medium, pigment dispersion or dye, and a polyol/alkylene oxide condensate cosolvent which eliminates film formation on thermal ink jet resistor surfaces thereby eliminating non-uniformity in optical density. The cosolvent present at least 5 percent has a solubility in water of at least 4.5 parts in 100 parts of water at 25° C. and a general formula:

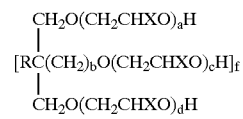

wherein X=—H or —$CH_3$; R=—H, —$CH_3$, —$C_2H_5$, —$C_3H_7$, —$C_4H_9$, or —$CH_2O(CH_2CH_2O)_eH$; b=0 or 1, a+d+f(c+e)=2 to 100; and f=1 to 6, the cosolvent being present in the amount of at least 4.5 percent based on the total weight of the ink jet ink composition. These inks exhibit freedom from thermal resistor film formation, have excellent decap performance, are storage stable and give images having excellent print quality.

U.S. Pat. No. 5,531,817 (Shields et al.), the disclosure of which s totally incorporated herein by reference, discloses the control of color bleed (the invasion of one color into another on the surface of the print medium) using ink-jet inks by employing either high molecular weight polymers that exhibit a reversible gelling nature with heat or certain amine oxide surfactants that undergo sol-gel transitions. The inks of the invention further include a vehicle and a dye. The vehicle typically comprises a low viscosity, high boiling point solvent and water. Certain high molecular weight polymers, under the correct solution conditions, can form gels which can be subsequently melted by heating of the gel. When the melted gel is cooled, it will then reform into a gel. The viscosity of an ink employing such a gel can be reduced to a viscosity low enough to permit jetting from the print cartridge. After leaving the print cartridge, the melted gel will again reform into a highly viscous gel to immobilize the droplet of ink and prevent its migration on the media. Therefore, two drops of different colors, when printed next to one another will thus be inhibited from migrating or bleeding into one another.

U.S. Pat. No. 5,476,540 (Shields et al.), the disclosure of which is totally incorporated herein by reference, discloses a method for controlling color bleed between adjacent multi-color ink regions on a print medium. Color bleed involves the migration of color agents between adjacent zones in a multicolored printed image on a print medium. A first composition containing a gel-forming species and a color agent is brought into contact on a region of the print medium with a second composition having a color agent and a gel-initiating species or chemical conditions which bring about gelation. In alternative embodiments, the print medium may be pretreated with either a gel-initiating species or a gel-forming species (with no colorant), followed by treatment with a gel-forming species or gel-initiating species (with colorant), respectively. The formation of the gel upon the print medium impedes the movement of the color agent or agents and thus reduces the color bleed between adjacent zones.

U.S. Pat. No. 5,389,958 (Bui et al.), the disclosure of which is totally incorporated herein by reference, discloses a method and apparatus whereby an intermediate transfer surface of a layer of sacrificial liquid is applied to a supporting surface and a phase change ink is deposited on the liquid layer. The inked image is then contact transferred to a final receiving substrate.

U.S. Pat. No. 5,554,212 (Bui et al.), the disclosure of which is totally incorporated herein by reference, discloses an aqueous phase change ink containing a water dispersible sulfonated polyester gloss agent and a selected concentration of hyperthermogelling component that causes the ink to gel when its temperature is increased to its thermo-inversion point or when the concentration of the hyperthermogelling component is increased by evaporation, or substrate absorption, of water from the ink. The ink may be jetted directly onto a heated and/or absorptive substrate or jetted onto a cooler and/or hydrophobic surface before being transferred to the substrate. The thermo-inversion point is preferably about ambient temperature, and the preferred hyperthermogelling component is a nonionic surfactant, such as an ethylene oxide propylene oxide block copolymer surfactant.

U.S. Pat. No. 5,462,591 (Karandikar et al.), the disclosure of which is totally incorporated herein by reference, discloses an aqueous phase change ink that contains a selected concentration of hyperthermogelling component that causes the ink to gel when its temperature is increased to its thermo-inversion point or when the concentration of the hyperthermogelling component is increased by evaporation, or substrate absorption, of water from the ink. The ink may be jetted directly onto a heated and/or absorptive substrate or jetted onto a cooler and/or hydrophobic surface before being transferred to the substrate. The thermo-inversion point is preferably about ambient temperature, and the preferred hyperthermogelling component is a nonionic surfactant, such as an ethylene oxide propylene oxide block copolymer surfactant.

U.S. Pat. No. 5,099,256 (Anderson), the disclosure of which is totally incorporated herein by reference, discloses an ink jet printer having a rotatable intermediate drum having a thermally conductive surface on which the ink droplets are printed from the printhead. The drum surface material is a suitable film forming silicone polymer having a high surface energy and surface roughness to prevent movement of the droplets after impact thereon. The printhead is located relative to the intermediate drum surface so that the ink droplets impact the drum surface with a large contact angle and the ink droplet image is transferred at a second location spaced from the printhead to minimize contaminating particles from the recording medium from reaching the printhead nozzles. The intermediate drum surface is heated to dehydrate the ink droplets prior to transfer from the intermediate drum to the recording medium. The silicone polymer coating enables substantially complete transfer of the dehydrated droplets to the recording medium, so that subsequent removal of the residual ink from the drum by a cleaning system is eliminated.

U.S. Pat. No. 4,538,156 (Durkee et al.), the disclosure of which is totally incorporated herein by reference, discloses an ink jet printer utilizing a smooth surfaced transfer drum as an illustrative embodiment of the invention. The transfer drum and the print head assembly are mounted between a pair of side plates. A print head assembly, which comprises a number of ink jet nozzles, is also mounted between the side plates. The print head assembly is spaced apart from the drum and the nozzles thereof are spaced at equal distances along a line which is parallel to the axis of the drum. The print head assembly is movable in fine steps from left to right so that on successive rotations of the drum each nozzle is directed to a new track of a succession of tracks. After all tracks of the transfer drum have been served by a nozzle assembly, a printing medium, e.g., paper is brought in rolling contact with the drum to transfer the indicia on the drum to the printing medium while the print head assembly is returned to its starting position; and thereafter, if required, the drum is wiped clean in preparation for receiving the next page of information.

U.S. Pat. No. 5,761,597 (Smith et al.), the disclosure of which is totally incorporated herein by reference, discloses an improved fusing apparatus for fixing or fusing images on print media wherein a relatively small pressure applying surface, such as the surface of a rotatable pressure wheel, is lubricated with a lubricating medium such as silicone oil, and engages the printed image to apply pressure and fuse the image to the image receiving substrate. The fusing apparatus is mounted for reciprocal back and forth movement across the printed image on the image receiving substrate or medium to fuse the image into the substrate and flatten or smooth the upper exposed surface of the ink image. The pressure wheel is passed in multiple overlapping passes over the printed image to uniformly fuse the image into the media.

U.S. Pat. No. 5,195,430, (Rise), the disclosure of which is totally incorporated herein by reference, discloses a fixing and developing apparatus in which sheet material to be treated is passed through a high pressure nip defined by a pair of rollers. At least one of the rollers may have a composite construction. The composite roller includes an elongated tubular shell with a pressure applying external surface, an elongated core positioned within the tubular shell, and an elastomeric material disposed between the core and shell to support the shell on the core. The core may be of a number of configurations and may increase in transverse cross-sectional dimension from the respective ends of the core toward the center of the core. The core may taper continuously or in discrete steps from its center toward its first and second ends. In addition, the core may have a longitudinal cross-section with a crown in the shape of a beam deflection curve for a simply supported, uniformly constant cross-section beam. The shell may be similarly configured along its interior surface. Also, the elastomer may be compressed at the center of the roller relative to the ends of the roller to preload its center portion.

U.S. Pat. No. 4,889,761 (Titterington et al.), the disclosure of which is totally incorporated herein by reference, discloses a method for producing a light-transmissive phase change ink printed substrate which comprises providing a substrate, and then printing on at least one surface of the substrate a predetermined pattern of a light-transmissive phase change ink which initially transmits light in a non-rectilinear path. The pattern of solidified phase change ink is then reoriented to form an ink layer of substantially uniform thickness. This ink layer will, in turn, produce an image which then will transmit light in a substantially rectilinear path. In one aspect of the invention, the substrate is light transmissive, and the reoriented printed substrate exhibits a high degree of lightness and chroma, and transmits light in a substantially rectilinear path. In this way, the reoriented printed substrate can be used in a projection device to project an image containing clear, saturated colors.

U.S. Pat. No. 4,745,420 (Gerstenmaier), the disclosure of which is totally incorporated herein by reference, discloses a method of ejecting droplets of phase change or hot melt ink jet ink upon a target such as paper which includes a step of applying pressure to the droplets after they have cooled upon the paper in order to increase their coverage and, thus, minimize the volume of ink required to produce a high quality print with a high degree of resolution. Including a means for applying pressure to the cooled droplets, a suitable apparatus increases the area of the target covered by a particular droplet after spreading by at least five percent and preferably by twenty percent.

U.S. Pat. No. 6,320,018 (Sijbesma et al.), the disclosure of which is totally incorporated herein by reference, discloses a polymer comprising monomeric units linked via four H-bridges and bound within said polymer via a different bond. The bond via the H-bridges is much stronger than with known supramolecular polymers.

U.S. Pat. No. 5,892,116 (Weiss et al.) and PCT Patent Publication WO 97/24364 (Weiss et al.), the disclosures of each of which are totally incorporated herein by reference, disclose gelators that gel a variety of nonpolar and polar liquids. Moreover, gelation of various monomers with subsequent polymerization of the gelled monomers forms organic zeolites and membrane materials. An ionic gelator includes salts of compounds of formula (I)

$$[R^1R^2R^3X-R^4]^{+Y\pm} \qquad \qquad \text{I}$$

where $R^1$, $R^2$, and $R^3$ are the same or different hydrogen or organic groups including alkyl groups, alkenyl groups, alkynyl groups, aryl groups, arylalkyl groups, alkoxy groups, aryloxy groups; X is a Group IIIA or Group VA element; $R^4$ is a steroidal group, an alkyl group, an alkenyl group, an alkynyl group, an aryl group, an arylalkyl group, an alkoxy group, or an aryloxy group; and Y is a Group IA or Group VIIA element or one-half of a Group IIA or VIA element, that is, a divalent counterion. The gelling agent composition may include a single isomer or mixtures of isomers of the formula (I). A non-ionic gelator also includes compounds of the formula (II):

$$R^1R^2R^3X \qquad \qquad \text{II}$$

where $R^1$, $R^2$, $R^3$, and X are defined as above.

Also of interest with respect to the present invention are the following references: "Reversible Polymers Formed from Self-Complementary Monomers Using Quadruple Hydrogen Bonding," R. P. Sijbesma et al., *Science*, Vol. 278, p. 1601 (1997); "Supramolecular Polymers," R. Dagani, *Chemical and Engineering News*, p. 4 (December 1997); "Supramolecular Polymers from Linear Telechelic Siloxanes with Quadruple-Hydrogen-Bonded Units," J. H. K. Hirschberg et al., *Macromolecules*, Vol. 32, p. 2696 (1999): "Design and Synthesis of 'Smart' Supramolecular Liquid Crystalline Polymers via Hydrogen-Bond Associations," A. C. Griffin et al., *PMSE Proceedings*, Vol. 72, p. 172 (1995); "The Design of Organic Gelators: Solution and Solid State Properties of a Family of Bis-Ureas," Andrew J. Carr et al., *Tetrahedron Letters*, Vol. 39, p. 7447 (1998); "Hydrogen-Bonded Supramolecular Polymer Networks," Ronald F. M. Lange et al., *Journal of Polymer Science, Part A: Polymer Chemistry*, Vol. 37, p. 3657 (1999); "Combining Self-Assembly and Self-Association—Towards Columnar Supramolecular Structures in Solution and in Liquid-Crystalline Mesophase," Arno Kraft et al., *Polym. Mater. Sci. Eng.*, Vol. 80, p. 18 (1999); "Facile Synthesis of β-Keto Esters from Methyl Acetoacetate and Acid Chloride: The Barium Oxide/Methanol System," Y. Yuasa et al., *Organic Process Research and Development*, Vol. 2, p. 412 (1998); "Self-Complementary Hydrogen Bonding of 1,1'-Bicyclohexylidene-4,4'-dione Dioxime. Formation of a Non-Covalent Polymer," F. Hoogesteger et al., *Tetrahedron*, Vol. 52, No. 5, p. 1773 (1996); "Molecular Tectonics. Three-Dimensional Organic Networks with Zeolite Properties," X. Wang et al., *J. Am. Chem. Soc.*, Vol. 116, p. 12119 (1994); "Helical Self-Assembled Polymers from Cooperative Stacking of Hydrogen-Bonded Pairs," J. H. K. Ky Hirschberg et al., *Nature*, Vol. 407, p. 167 (2000); "New Supramolecular Arrays based on Interactions between Carboxylate and Urea Groups: Solid-State and Solution Behavior," Abdullah Zafar et al., *New J. Chem.*, 1998, 137–141; "The Unusual Molecular Organization of 2,3-Bis (n-hexyloxy)-anthracene in the Crystal. A Hint to the Origin of the Gelifying Properties of 2,3-Bis(n-alkyloxy)anthracenes?", J-L. Pozzo et al., *J. Chem. Soc., Perkin Trans.*, 2, 824–826 (2001); "The Quest for the Simplest Possible Organogelators and Some Properties of their Organogels," D. Abdallah et al., *J. Braz. Chem. Soc.*, Vol. 11, No. 3, 209–218 (2000); "Organogel Electrolytes Based on a Low Molecular Weight Gelator: 2,3-Bis(n-decyloxy)anthracene," F. Placin et al., *Chem. Mater.* 13, 117–121 (2001); "Novel Vesicular Aggregates of Crown-Appended Cholesterol Derivatives Which Act as Gelators of Organic Solvents and as Templates for Silica Transcription," J. Jung et al., *J. Am. Chem. Soc.*, Vol. 122, No. 36, 8648–8653 (2000); "n-Alkanes Gel n-Alkanes (and Many Other Organic Liquids)," D. Abdallah et al., *Langmuir*, 16, 352–355 (2000); "Low Molecular Mass Gelators of Organic Liquids and the Properties of their Gels," P. Terech et al., *Chem. Rev.*, 97, 3133–3159 (1997); "Organogels and Low Molecular Mass Organic Gelators," D. Abdallah et al., *Adv. Mater.*, 12, No. 17, 1237 (2000); "Making it All Stick Together: the Gelation of Organic Liquids by Small Organic Molecules," F. Schoonbeek, Doctoral Thesis, U. of Groningen, Netherlands, April 2001; Twieg et al., *Macromolecules*, Vol. 18, p. 1361 (1985); "Synthesis and Reactions of Polyhydric Alcohols I. Synthesis and Reactions of p-Toluenesulfonates of Polyhydric Alcohols," *Zhurnal Obshchei Khimii*, Vol. 35, No. 5, p. 804–807 (1965); "The Chemotherapy of Schistosomiasis. Part I. Derivatives and Analogs of αω-Di-(p-aminophenoxy)alkanes," J. Ashley et al., *J. Chem. Soc.* 1958, 3293; "Remarkably Simple Small Organogelators: Di-n-alkoxy-benzene Derivatives," G. Clavier et al., *Tetrahedron Letters*, 40, 9021–9024 (1999); "Rational Design of Low Molecular Mass Organogelators: Toward a Library of Functional N-Acyl-1-ω-Amino Acid Derivatives," G. Mieden-Gundert et al., *Angew. Chem. Int. Ed.*, 40, No. 17, 3164–3166 (2001); U.S. Pat. No. 2,703,808 (Buchman); "Rational Design of New Acid-Sensitive Organogelators," J-L. Pozo et al., *J. Mater. Chem.*, Vol. 8, pp. 2575–2577 (1998); J. T. Thurston et al., *J. Am. Chem. Soc.*, Vol. 73, pp. 2981–3008 (1951); *J. Am. Chem. Soc.*, Vol. 96, pp. 1082–1087 (1974); J-L. Pozo et al., *Tetrahedron*, Vol. 53, No. 18, pp. 6377–6390 (1997); J-L. Pozo et al., *Mol. Cryst. Liq. Cryst.*, Vol. 344, pp. 101–106 (2000); Y. C. Lin, R. G. Weiss, *Macromolecules*, Vol. 20, p. 414 (1987); Weiss et al., U.S. Pat. No. 4,790,961; Murata et al, *J. Am. Chem. Soc.*, Vol. 116, No 15, pp. 6664–6676 (1994); A. Ikeda et al., *Rep. Asahi Glass Found. Ind. Technol.*, Vol. 61, p. 115, (1992); Rabolt et al., *Macromolecules*, Vol. 17, p. 2786 (1984); D. J. Abdallah et al., *Chem. Mater.*, Vol. 11, p. 2907 (1999); Ralston et al., *J. Org. Chem.*, Vol. 9, p. 259 (1944); L. Lu et al., *Chem. Commun.*, 1996, p. 2029; *J. Prakt. Chem.*, Vol. 327 (3), pp. 383–98 (1985); B. L. Feringa et al., *J. Org. Chem.*, Vol. 53, p. 1125 (1988); J. C. DeJong et al., *Tetrahedron Lett.*, Vol. 30, p. 7239 (1989); J. C. DeJong, Ph.D. thesis, University of Groningen, The Netherlands, 1991; F. A. Neugebauer et al., *Chem. Ber.*, 1976, 109, 2389; U. Zehavi et al., *J. Org. Chem.*, Vol. 26, pp. 1097–1101 (1961); J. March, *Advanced Organic Chemistry*, 4th Edition, pp. 903 and 1091–1092, Wiley Interscience (New York 1992); J. Crossley Maxwell, *Aust. J. Chem.*, Vol. 47, pp. 723–738 (1994); V. J. Wotring et al., *Analytical Chemistry*, Vol. 62, No. 14, pp. 1506–1510 (1990); Tabushi et al., *J. Am. Chem. Soc.*, Vol. 103, pp. 6152–6157 (1981); T. Giorgi et al., "Gel-like lyomesophases formed in organic solvents by self-assembled guanine ribbons," *Chemistry—A European Journal* (2002), 8(9), 2143–2152; T. Suyamaet al., "A method for the preparation of substituted biguanides," *Nippon Kagaku Kaishi* (1989), (5), 884–7; Polish Patent Publication PL 148060 B1; Polish Patent Publication PL 134682 B1; C. S. Snijder et al., *Chem. Eur. J.*, Vol. 1, No. 9, pp. 594–597 (1995); S. Senda et al., Gifu Coll. Pharm., Gifu, Japan. *Yakugaku Zasshi* (1969), 89 (2), 254–259; B. Gluncic et al, *Acta Pharm. Jugosl.* (1986), 36(4), 393–404; Canadian Patent Publication CA 941377; M. Klein, Recent Dev. Mass Spectrom. Biochem. Med., [Proc. Int. Symp.], 4th (1978), Meeting Date 1977, 1, 471–82; PCT Patent Publication WO/9011283; Japanese Patent Publication JP 62181279; T. Wada et al., "A New Boranophosphorylation Reaction for the Synthesis of Deoxyribonucleoside Boranophosphates," *Tetrahedron Letters*, Vol. 43, No. 23, pp. 4137–4140 (2002); R. Schirrmacher et al., "Dimethylpyridin-4-ylamine-catalysed alcoholysis of 2-amino-N,N,N-trimethyl-9H-purine-6-ylammonium chloride: An effective route to O6-substituted guanine derivatives from alcohols with poor nucleophilicity," *Synthesis*, Vol. 4, pp. 538–542 (2002); Z. Situ, "Synthesis of Tricyclic Derivatives of Guanine Analogue Catalyzed by KF-Al$_2$O$_3$," *Huaxue Shiji*, Vol. 24, No. 1, p. 57 (2002); Korean Patent 2000003081 (Korean Patent Application KR 1998-24185); S. Bailey et al., "Synthesis and Antiviral Activity of 9-Alkoxypurines: New 9-(Hydroxyalkoxy) Derivatives of Guanine and 8-Methylguanine," *Antiviral Chem. Chemother.*, Vol. 5, No. 1, pp. 21–33 (1994); Japanese Patent Publication JP 06157529; Japanese Patent Publication JP 3217541; M. R. Harnden et al., "Synthesis, Oral Bioavailability and In Vivo Activity of Acetal Derivatives of the Selective Antiherpesvirus Agent 9-(3-Hydroxypropoxy)Guanine (BRL44385)," *Antiviral Chem. Chemother.*, Vol. 5, No. 3, pp. 147–54 (1994); Spanish Patent Publication ES 2047457; B. K. Bhattacharya et al., "Synthesis of Certain N- and C-alkyl Purine Analogs," *J. Heterocycl. Chem.*, Vol. 30, No. 5, pp. 1341–9 (1993); Polish Patent Publication PL 148969; PCT Patent Publication WO/9011283; U.S. Pat. No. 5,298,618 (Speranza et al.); and Japanese Patent Publication JP 62181279, the disclosures of each of which are totally incorporated herein by reference.

While known compositions and processes are suitable for their intended purposes; a need remains for phase change inks that are suitable for hot melt ink jet printing processes, such as hot melt piezoelectric ink jet printing processes and the like. In addition, a need remains for phase change inks that generate images with reduction in waxy texture and feel. Further, a need remains for phase change inks that generate images with improved rub and scratch resistance. Additionally, a need remains for phase change inks that generate images with improved smear resistance. There is also a need for phase change inks with desirably low viscosity values at the jetting temperature of a hot melt ink jet printer. In addition, there is a need for nonaqueous phase change inks wherein water-soluble dyes can be selected as colorants. Further, there is a need for phase change inks that generate images with improved image permanence. Additionally, there is a need phase change inks that generate images with improved adhesion to print substrates such as paper and transparency material. A need also remains for phase change inks that can be fused or transfused to substrates at relatively high temperatures, thereby enabling better control of the fusing process and better penetration of the inks into the final recording substrates.

SUMMARY OF THE INVENTION

The present invention is directed to compounds of the formulae

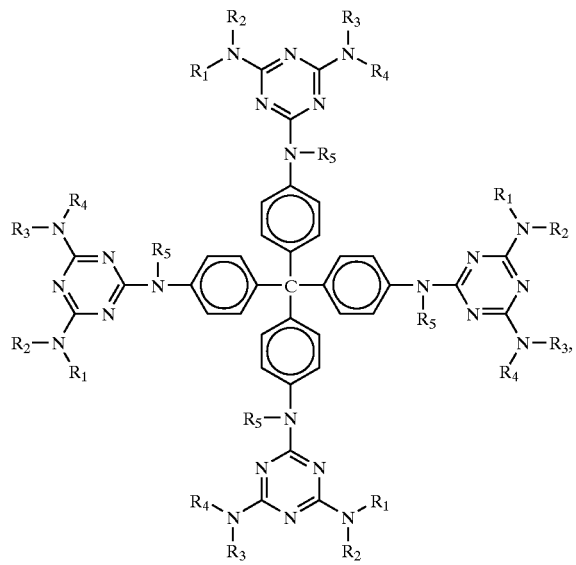

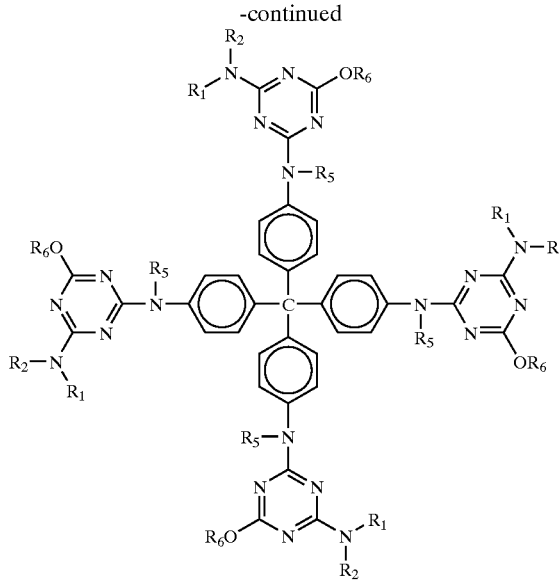

and

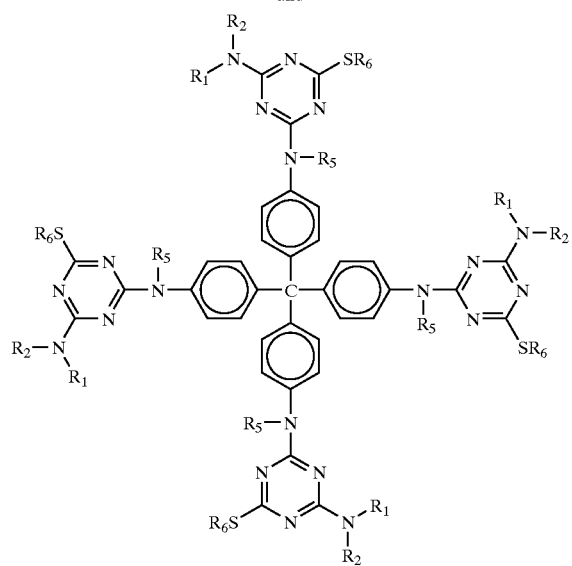

wherein, provided that at least one of $R_1$, $R_2$, $R_3$, $R_4$, $R_5$, and $R_6$ is a hydrogen atom, and provided that at least one of $R_1$, $R_2$, $R_3$, $R_4$, $R_5$, and $R_6$ is not a hydrogen atom, $R_1$, $R_2$, $R_3$, $R_4$, $R_5$, and $R_6$ each, independently of the others, is (i) a hydrogen atom, (ii) an alkyl group, (iii) an aryl group, (iv) an arylalkyl group, or (v) an alkylaryl group. Another embodiment of the present invention is directed to a phase change ink composition comprising a colorant and a phase change ink carrier comprising a material of this formula.

DETAILED DESCRIPTION OF THE INVENTION

The present invention is directed to compounds of the formula

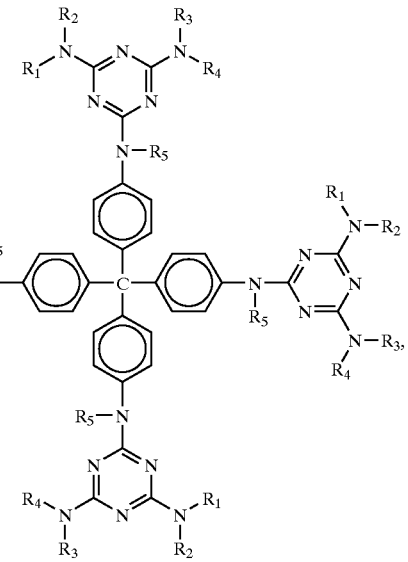

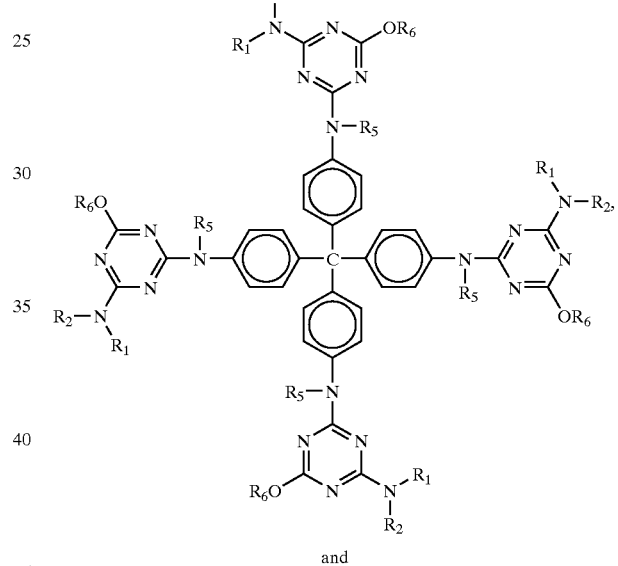

and

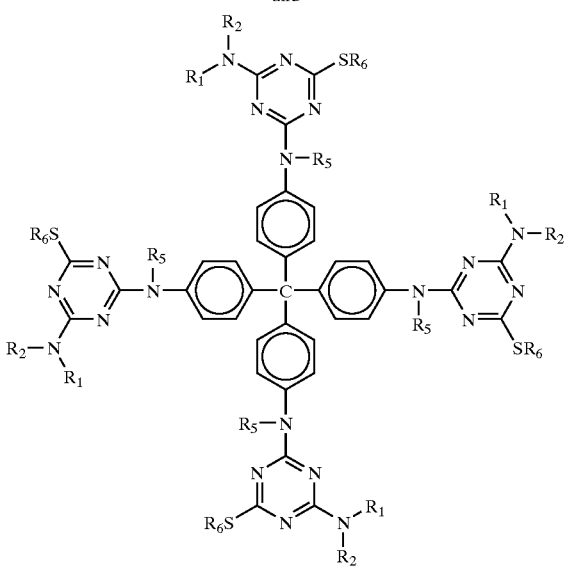

wherein, provided that at least one of $R_1$, $R_2$, $R_3$, $R_4$, $R_5$, and $R_6$ is a hydrogen atom, and provided that at least one of $R_1$, $R_2$, $R_3$, $R_4$, $R_5$, and $R_6$ is not a hydrogen atom, $R_1$, $R_2$, $R_3$, $R_4$, $R_5$, and $R_6$ each, independently of the others, is (i) a hydrogen atom, (ii) an alkyl group (including linear, branched, saturated, unsaturated, cyclic, unsubstituted, and substituted alkyl groups, and wherein hetero atoms, such as oxygen, sulfur, nitrogen, silicon, phosphorus, or the like, either may or may not be placed between the carbon atoms in the alkyl group), in one embodiment with at least about 1 carbon atom, in another embodiment with at least about 3 carbon atoms, in yet another embodiment with at least about 4 carbon atoms, in still another embodiment with at least about 6 carbon atoms, and in yet another embodiment with at least about 8 carbon atoms, and in one embodiment with no more than about 96 carbon atoms, in another embodiment with no more than about 48 carbon atoms, in yet another embodiment with no more than about 25 carbon atoms, and in still another embodiment with no more than about 20 carbon atoms, although the number of carbon atoms can be outside of these ranges, (iii) an aryl group (including unsubstituted and substituted aryl groups, and wherein hetero atoms, such as oxygen, sulfur, nitrogen, silicon, phosphorus, or the like, either may or may not be present in the aryl group), in one embodiment with at least about 6 carbon atoms, and in one embodiment with no more than about 50 carbon atoms, in another embodiment with no more than about 22 carbon atoms, in yet another embodiment with no more than about 18 carbon atoms, and in still another embodiment with no more than about 12 carbon atoms, although the number of carbon atoms can be outside of these ranges, (iv) an arylalkyl group (including unsubstituted and substituted arylalkyl groups, and wherein hetero atoms, such as oxygen, nitrogen, sulfur, silicon, phosphorus, and the like either may or may not be present in either or both of the alkyl portion and the aryl portion of the arylalkyl group), in one embodiment with at least about 7 carbon atoms, and in another embodiment with at least about 8 carbon atoms, and in one embodiment with no more than about 96 carbon atoms, in another embodiment with no more than about 24 carbon atoms, and in yet another embodiment with no more than about 12 carbon atoms, although the number of carbon atoms can be outside of these ranges, or (v) an alkylaryl group (including unsubstituted and substituted alkylaryl groups, and wherein hetero atoms, such as oxygen, nitrogen, sulfur, silicon, phosphorus, and the like either may or may not be present in either or both of the alkyl portion and the aryl portion of the alkylaryl group), in one embodiment with at least about 7 carbon atoms, and in another embodiment with at least about 8 carbon atoms, and in one embodiment with no more than about 96 carbon atoms, in another embodiment with no more than about 24 carbon atoms, and in yet another embodiment with no more than about 12 carbon atoms, although the number of carbon atoms can be outside of these ranges, wherein the substituents on the substituted alkyl, aryl, arylalkyl, and alkylaryl groups can be (but are not limited to) hydroxy groups, halogen atoms, amine groups, imine groups, ammonium groups, pyridine groups, pyridinium groups, ether groups, aldehyde groups, ester groups, amide groups, carbonyl groups, thiocarbonyl groups, sulfate groups, sulfonate groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, azo groups, cyanato groups, isocyanato groups, thiocyanato groups, isothiocyanato groups, alkoxy groups wherein the alkyl portion thereof is defined as alkyl is defined for $R_1$, aryloxy groups wherein the aryl portion thereof is defined as aryl is defined for $R_1$, arylalkyloxy groups wherein the arylalkyl portion thereof is defined as arylalkyl is defined for $R_1$, alkylaryloxy groups wherein the alkylaryl portion thereof is defined as alkylaryl is defined for $R_1$, a polyalkyleneoxy groups, wherein the alkyl portion of the repeat alkyleneoxy groups typically has from about 1 to about 12 carbon atoms, although the number of carbon atoms can be outside of these ranges, such as a polyethyleneoxy group, a polypropyleneoxy group, a polybutyleneoxy group, or the like, and wherein the number of repeat alkyleneoxy groups typically is from about 2 to about 50 repeat alkyleneoxy groups, although the number of repeat units can be outside of these ranges, polyaryleneoxy groups, wherein the aryl portion of the repeat aryleneoxy groups typically has from about 6 to about 14 carbon atoms, although the number of carbon atoms can be outside of these ranges, such as a polyphenyleneoxy group, a polynaphthaleneoxy group, a polyphenanthreneoxy group, or the like, and wherein the number of repeat aryleneoxy groups typically is from about 2 to about 20 repeat aryleneoxy groups, although the number of repeat units can be outside of these ranges, polyarylalkyleneoxy groups, wherein the arylalkyl portion of the repeat arylalkyleneoxy groups typically has from about 7 to about 50 carbon atoms, although the number of carbon atoms can be outside of these ranges, such as a polybenzyleneoxy group, a polyphenylethyleneoxy group, or the like, and wherein the number of repeat arylalkyleneoxy groups typically is from about 2 to about 20 repeat arylalkyleneoxy groups, although the number of repeat units can be outside of these ranges, polyalkylaryleneoxy group, wherein the alkylaryl portion of the repeat alkylaryleneoxy groups typically has from about 7 to about 50 carbon atoms, although the number of carbon atoms can be outside of these ranges, such as a polytolueneoxy group or the like, and wherein the number of repeat alkylaryleneoxy groups typically is from about 2 to about 20 repeat alkylaryleneoxy groups, although the number of repeat units can be outside of these ranges, silyl groups, siloxane groups, polysilylene groups, typically with from 2 to about 100 repeat silylene units, although the number of repeat silylene units can be outside of this range, polysiloxane groups, typically with from 2 to about 200 repeat siloxane units, although the number of repeat siloxane units can be outside of this range, mixtures thereof, and the like, wherein two or more substituents can be joined together to form a ring.

In a specific embodiment, the compounds of the present invention are nonpolymeric.

Some specific examples of $R_1$ include hydrogen, groups of the formula —$(CH_2)_n CH_3$ wherein n is an integer of from 0 to about 40, such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl (also called arachidyl), and the like.

Some specific examples of $R_2$ include hydrogen, groups of the formula —$(CH_2)_n CH_3$ wherein n is an integer of from 0 to about 40, such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl (also called arachidyl), and the like.

Some specific examples of $R_3$ include hydrogen, groups of the formula —$(CH_2)_n CH_3$ wherein n is an integer of from 0 to about 40, such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl (also called arachidyl), and the like.

Some specific examples of $R_4$ include hydrogen, groups of the formula —$(CH_2)_n CH_3$ wherein n is an integer of from 0 to about 40, such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl (also called arachidyl), and the like.

Some specific examples of $R_5$ include hydrogen, groups of the formula —$(CH_2)_n CH_3$ wherein n is an integer of from 0 to about 40, such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl (also called arachidyl), and the like.

Some specific examples of $R_6$ include hydrogen, groups of the formula —$(CH_2)_n CH_3$ wherein n is an integer of from 0 to about 40, such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl (also called arachidyl), and the like, branched hydrocarbons (including those having hetero atoms therein), such as groups of the formula

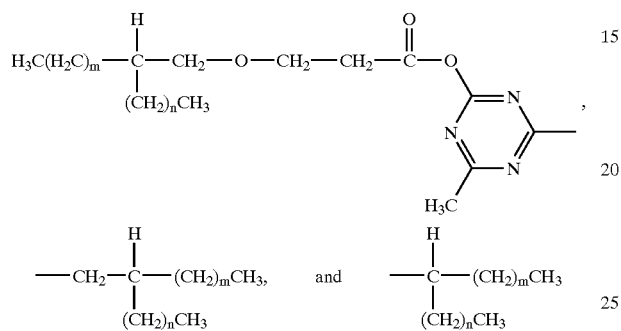

wherein m and n each represent numbers of repeat —$CH_2$— groups and each, independently of the other, is from 1 to about 40, and the like,

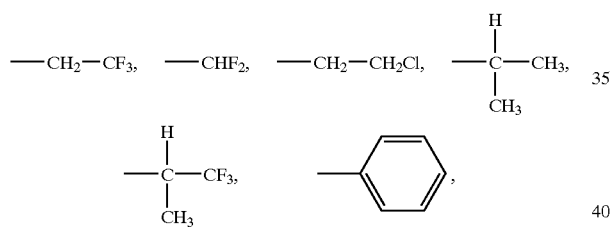

and the like.

Some specific examples of compounds according to the present invention include

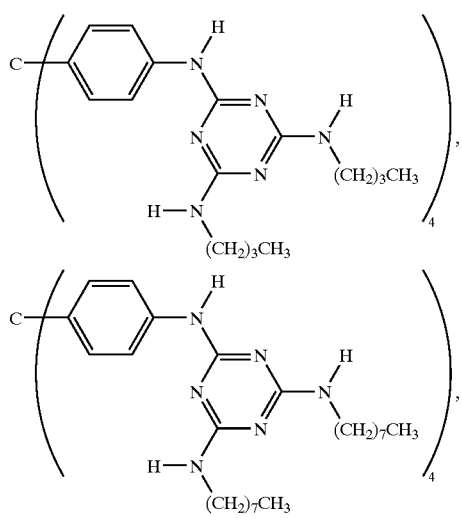

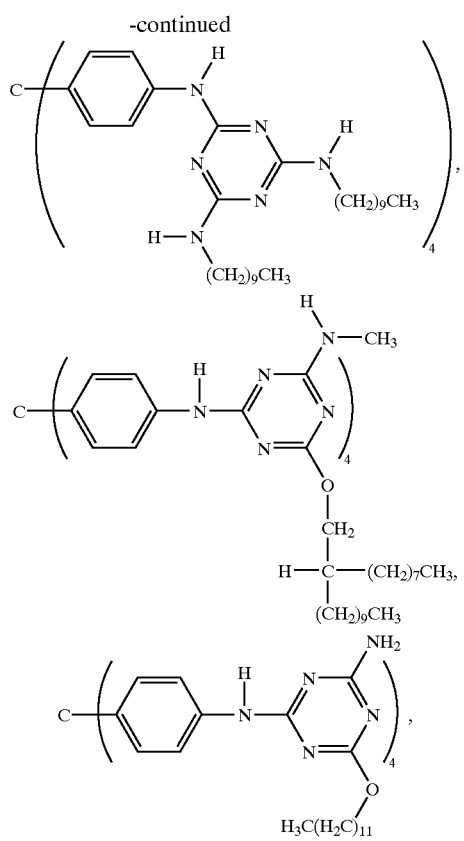

and the like, as well as mixtures thereof.

These materials can be prepared by any desired or suitable process. Another embodiment of the present invention is directed to a process for preparing a compound of the formula

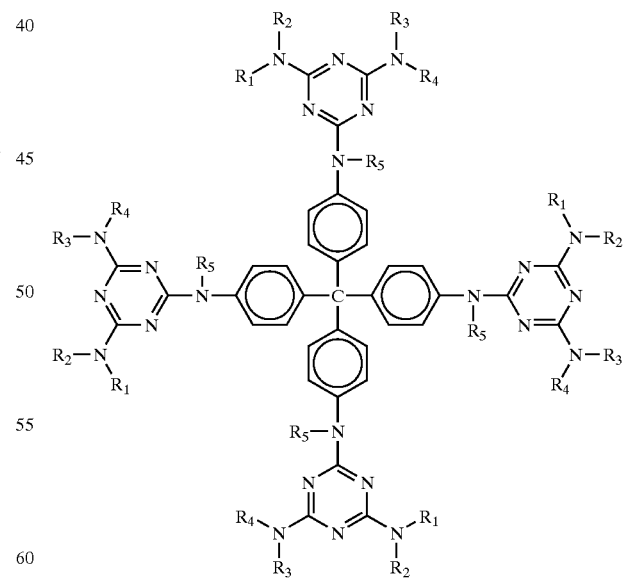

wherein, provided that at least one of $R_1$, $R_2$, $R_3$, $R_4$, and $R_5$ is a hydrogen atom, and provided that at least one of $R_1$, $R_2$, $R_3$, $R_4$, $R_5$, and $R_6$ is not a hydrogen atom, $R_1$, $R_2$, $R_3$, $R_4$, and $R_5$ each, independently of the others, is (i) a hydrogen atom, (ii) an alkyl group, (iii) an aryl group, (iv) an arylalkyl group, or (v) an alkylaryl group, which comprises preparing a reaction mixture by admixing a compound of the formula

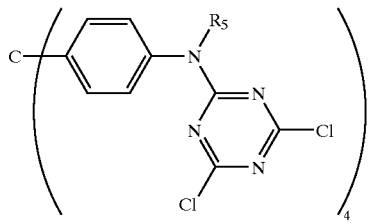

with one or more amines of the formulae $R_1R_2NH$ and $R_3R_4NH$, wherein $R_1$, $R_2$, $R_3$, and $R_4$ can be either the same as each other or different from each other and allowing the reactants to react at a temperature of at least about 40° C., thereby generating a compound of the formula

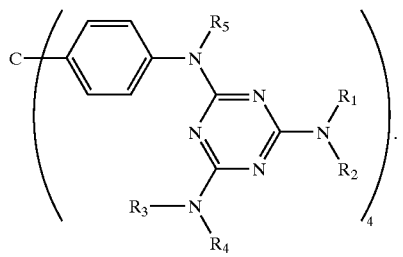

More specifically, in one embodiment, these compounds can be prepared by the reaction of an amine or a mixture of amines with tetrakis[4[(2,4-dichloro-1,3,5-triazin-6-yl)amino]phenyl]methane or a substituted form thereof as follows:

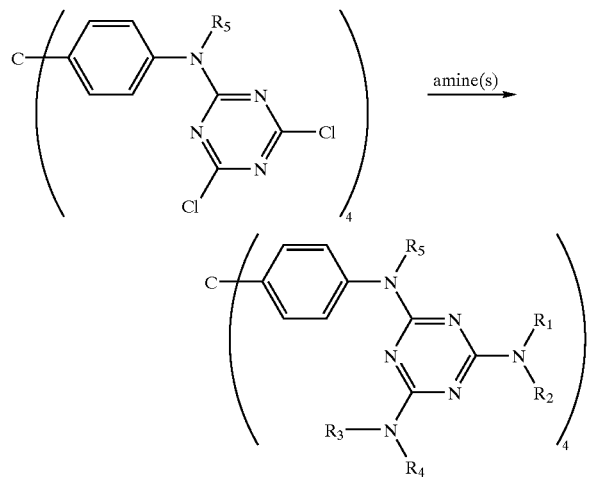

The desired amine or mixture of amines corresponding to the desired $R_1$, $R_2$, $R_3$, and $R_4$ groups is admixed with the tetrakis[4[(2,4-dichloro-1,3,5-triazin-6-yl)amino]phenyl]methane.

The amine or mixture of amines is present in any desired or effective amount, in one embodiment at least about 4 moles of amine per mole of tetrakis[4[(2,4-dichloro-1,3,5-triazin-6-yl)amino]phenyl]methane, in another embodiment at least about 8 moles of amine per mole of tetrakis[4[(2,4-dichloro-1,3,5-triazin-6-yl)amino]phenyl]methane, and in yet another embodiment at least about 12 moles of amine per mole of tetrakis[4[(2,4-dichloro-1,3,5-triazin-6-yl)amino]phenyl]methane, and in one embodiment no more than about 40 moles of amine per mole of tetrakis[4[(2,4-dichloro-1,3,5-triazin-6-yl)amino]phenyl]methane, in another embodiment no more than about 20 moles of amine per mole of tetrakis[4[(2,4-dichloro-1,3,5-triazin-6-yl)amino]phenyl]methane, and in yet another embodiment no more than about 15 moles of amine per mole of tetrakis[4[(2,4-dichloro-1,3,5-triazin-6-yl)amino]phenyl]methane, although the relative amounts can be outside of these ranges.

Optionally, the tetrakis[4[(2,4-dichloro-1,3,5-triazin-6-yl)amino]phenyl]methane and the amines are admixed in the presence of a solvent. Any desired or effective solvent can be used, such as tetrahydrofuran, dioxane, acetonitrile, mixtures thereof, or the like. When used, the solvent is present in any desired or effective amount, in one embodiment at least about 0.5 liters of solvent per every one mole of tetrakis[4[(2,4-dichloro-1,3,5-triazin-6-yl)amino]phenyl]methane, in another embodiment at least about 1 liter of solvent per every one mole of tetrakis[4[(2,4-dichloro-1,3,5-triazin-6-yl)amino]phenyl]methane, and in yet another embodiment at least about 2 liters of solvent per every one mole of tetrakis[4[(2,4-dichloro-1,3,5-triazin-6-yl)amino]phenyl]methane, and in one embodiment no more than about 10 liters of solvent per every one mole of tetrakis[4[(2,4-dichloro-1,3,5-triazin-6-yl)amino]phenyl]methane, in another embodiment no more than about 4 liters of solvent per every one mole of tetrakis[4[(2,4-dichloro-1,3,5-triazin-6-yl)amino]phenyl]methane, and in yet another embodiment no more than about 2 liters of solvent per every one mole of tetrakis[4[(2,4-dichloro-1,3,5-triazin-6-yl)amino]phenyl]methane, although the relative amount of solvent can be outside of these ranges.

The reaction between the amine or mixture of amines and the tetrakis [4[(2,4-dichloro-1,3,5-triazin-6-yl)amino]phenyl]methane can take place at any desired or effective temperature, in one embodiment at least about 40° C., in another embodiment at least about 50° C., and in yet another embodiment at least about 60° C., and in one embodiment no more than about 160° C., in another embodiment no more than about 80° C., and in yet another embodiment no more than about 70° C., although the temperature can be outside of these ranges.

The reaction between the amine or mixture of amines and the tetrakis[4[(2,4-dichloro-1,3,5-triazin-6-yl)amino]phenyl]methane can take place for any desired or effective period of time, in one embodiment at least about 20 minutes, in another embodiment at least about 1 hour, and in yet another embodiment at least about 2 hours, and in one embodiment no more than about 24 hours, in another embodiment no more than about 6 hours, and in yet another embodiment no more than about 4 hours, although the reaction time can be outside of these ranges.

Subsequent to completion of the reaction, the product can be purified.

Another embodiment of the present invention is directed to a process for preparing a compound of the formula

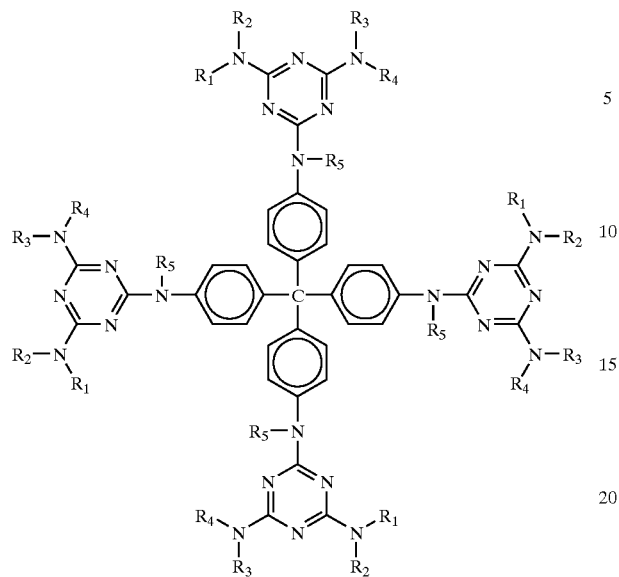

wherein, provided that at least one of $R_1$, $R_2$, $R_3$, $R_4$, and $R_5$ is a hydrogen atom, and provided that at least one of $R_1$, $R_2$, $R_3$, $R_4$, $R_5$, and $R_6$ is not a hydrogen atom, $R_1$, $R_2$, $R_3$, $R_4$, and $R_5$ each, independently of the others, is (i) a hydrogen atom, (ii) an alkyl group, (iii) an aryl group, (iv) an arylalkyl group, or (v) an alkylaryl group, which comprises (I) preparing a reaction mixture by admixing a compound of the formula

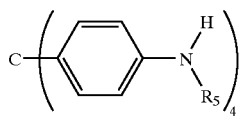

with a cyanuric halide at a temperature below about 0° C.; and (II) thereafter adding thereto one or more amines of the formulae $R_1R_2NH$ and $R_3R_4NH$, wherein $R_1$, $R_2$, $R_3$, and $R_4$ can be either the same as each other or different from each other and allowing the reactants to react at a temperature of at least about 40° C., thereby generating a compound of the formula

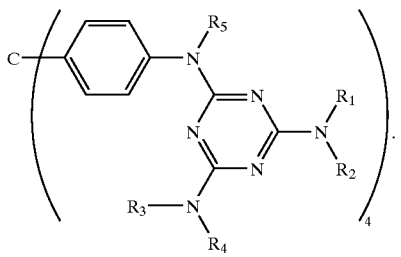

More specifically, these materials can be prepared by the reaction of tetrakis(4-aminophenyl)methane or a substituted form thereof with a cyanuric halide such as cyanuric chloride or cyanuric bromide at cold temperatures, followed by the reaction of the product thus generated with the desired amine or mixture of amines corresponding to the desired $R_1$, $R_2$, $R_3$, and $R_4$ groups as follows:

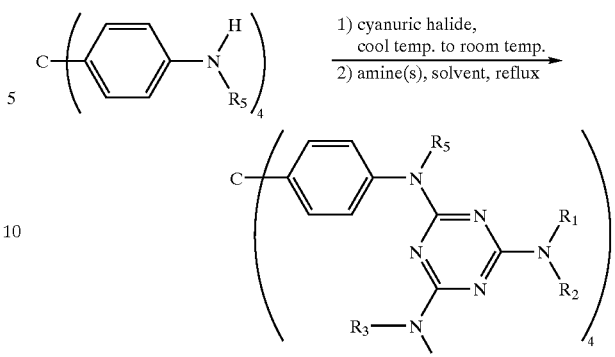

The tetrakis(4-aminophenyl)methane and the cyanuric halide are admixed in any desired or effective relative amounts, in one embodiment at least about 4 moles of cyanuric halide per every one mole of tetrakis(4-aminophenyl)methane, in another embodiment at least about 6 moles of cyanuric halide per every one mole of tetrakis (4-aminophenyl)methane, and in yet another embodiment at least about moles of cyanuric halide per every one mole of tetrakis(4-aminophenyl)methane, and in one embodiment no more than about 20 moles of cyanuric halide per every one mole of tetrakis(4-aminophenyl)methane, in another embodiment no more than about 12 moles of cyanuric halide per every one mole of tetrakis(4-aminophenyl)methane, and in yet another embodiment no more than about 8 moles of cyanuric halide per every one mole of tetrakis(4-aminophenyl)methane, although the relative amounts of these reactants can be outside of these ranges.

When $R_5$ is not hydrogen, and if $R_5$ is an electron withdrawing group, the reaction with the cyanuric halide may also be assisted by the presence of a strong non-nucleophilic base, such as sodium hydride (NaH). This strong non-nucleophilic base is added to the reaction mixture containing the tetrakis(4-aminophenyl)methane and the cyanuric halide in any desired or effective amount; for example, if it is desired to substitute each hydrogen atom on the —$NHR_5$ group with the triazine moiety, then about one molar equivalent of strong non-nucleophilic base is added for every —$NHR_5$ group desired to be substituted with the triazine moiety (for example, four equivalents in the reaction

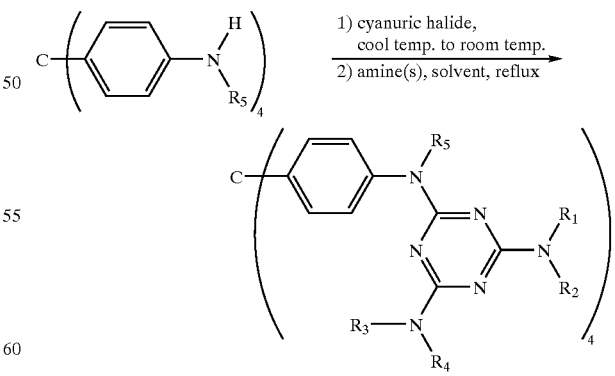

Optionally, the tetrakis(4-aminophenyl)methane and the cyanuric halide are admixed in the presence of a solvent. Any desired or effective solvent can be used, such as tetrahydrofuran, dioxane, acetonitrile, mixtures thereof, or the like. When used, the solvent is present in any desired or effective amount, in one embodiment at least about 0.5 liters of solvent per every one mole of tetrakis(4-aminophenyl) methane, in another embodiment at least about 1 liter of solvent per every one mole of tetrakis(4-aminophenyl) methane, and in yet another embodiment at least about 2 liters of solvent per every one mole of tetrakis(4-aminophenyl)methane, and in one embodiment no more than about 10 liters of solvent per every one mole of tetrakis(4-aminophenyl)methane, in another embodiment no more than about 4 liters of solvent per every one mole of tetrakis(4-aminophenyl)methane, and in yet another embodiment no more than about 2 liters of solvent per every one mole of tetrakis(4-aminophenyl)methane, although the relative amount of solvent can be outside of these ranges.

The reaction between the tetrakis(4-aminophenyl) methane and the cyanuric halide is initiated at any desired or effective lowered temperature, in one embodiment about −10° C., in another embodiment about 0° C., and in yet another embodiment about 5° C., although the initial temperature can be outside of these ranges.

The reaction mixture containing the tetrakis(4-aminophenyl)methane and the cyanuric halide is then allowed to warm to room temperature (typically about 20° C.) over any desired or effective period of time, in one embodiment at least about 5 minutes, in another embodiment at least about 30 minutes, and in yet another embodiment at least about 1 hour, and in one embodiment no more than about 4 hours, although the time can be outside of these ranges.

After the reaction mixture containing the tetrakis(4-aminophenyl)methane and the cyanuric halide has warmed to room temperature, the desired amine or mixture of amines is added to the reaction mixture. The amine or amines are added in any desired or effective amount, in one embodiment at least about 8 moles of amine per every one mole of tetrakis(4-aminophenyl)methane, and in another embodiment at least about 20 moles of amine per every one mole of tetrakis(4-aminophenyl)methane, and in one embodiment no more than about 60 moles of amine per every one mole of tetrakis(4-aminophenyl)methane, and in another embodiment no more than about 40 moles of amine per every one mole of tetrakis(4-aminophenyl)methane, although the relative amounts can be outside of these ranges.

The reaction mixture containing the amine is then heated, in one embodiment at least about 40° C., and in another embodiment at least about 50° C., and in one embodiment no more than about 80° C., and in another embodiment no more than about 60° C., although the temperature can be outside of these ranges.

The reaction mixture containing the amine is heated for any desired or effective period of time, in one embodiment at least about 30 minutes, in another embodiment at least about 1 hour, and in yet another embodiment at least about 2 hours, and in one embodiment no more than about 24 hours, in another embodiment no more than about 4 hours, and in yet another embodiment no more than about 2 hours, although the reaction time can be outside of these ranges.

Subsequent to cooling of the reaction mixture, the solvent can be removed and the product purified.

Starting materials for these reactions can be prepared by any desired or effective methods. For example, tetrakis(4-aminophenyl)methane and tetrakis[4[(2,4-dichloro-1,3,5-triazin-6-yl)amino]phenyl]methane can be prepared as described in Examples A, B, C, and D hereinbelow or as described in, for example, J. T. Thurston et al., *J. Am. Chem. Soc.*, Vol. 73, pp. 2981–3008 (1951); and F. A. Neugebauer et al., *Chem. Ber.*, Vol. 109, p. 2389 (1976), the disclosures of each of which are totally incorporated herein by reference.

The triaminotriazines in the phase change ink carriers of the inks of the present invention form reversible hydrogen bonds, resulting in the formation of dimers, oligomers, polymers, or polymer networks held together by hydrogen bonds instead of covalent bonds. An example of such bond formation is illustrated as follows:

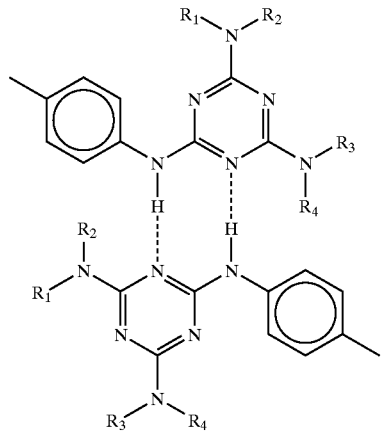

While not being limited to any particular theory, it is believed that in the inks of the present invention, some of these hydrogen bonds can be broken at the temperatures at which hot melt ink jet printing occurs (typically, although not necessarily, over 100° C.). When the ink is printed onto an intermediate transfer member or a final recording substrate, the ink cools as it is printed, which results in reformation of any hydrogen bonds broken by heating. The polymer-like materials thus formed behave like conventional covalently-bonded polymers to enhance image permanence.

The formation of hydrogen-bonded oligomers or polymers from specific ink carrier materials can be determined by any desired method. For example, a dramatic onset of resinous and viscoelastic characteristics on cooling is indicative of the formation of hydrogen-bonded oligomers or polymers from the ink carrier material or combination of materials. The formation of hydrogen bonds and hydrogen-bonded oligomers or polymers can also be detected by IR spectroscopy. NMR spectroscopy may also help to detect the presence of hydrogen-bonded oligomers or polymers. In situations wherein the ink carrier material is crystalline, X-ray crystallography can be used to define the oligomeric or polymeric structure.

In the direct printing mode, the phase change carrier composition in one embodiment contains one or more materials that enable the phase change ink (1) to be applied in a thin film of uniform thickness on the final recording substrate (such as paper, transparency material, and the like) when cooled to ambient temperature after printing directly to the recording substrate, (2) to be ductile while retaining sufficient flexibility so that the applied image on the substrate will not fracture upon bending, and (3) to possess a high degree of lightness, chroma, transparency, and thermal stability.

In an offset printing transfer or indirect printing mode, the phase change carrier composition in one embodiment exhibits not only the characteristics desirable for direct printing mode inks, but also certain fluidic and mechanical properties desirable for use in such a system, as described in, for example, U.S. Pat. No. 5,389,958, the disclosure of which is totally incorporated herein by reference.

In some embodiments of the present invention, the compound of the present invention functions as the sole phase change ink carrier for the ink composition. In other embodiments, if desired, other phase change ink carrier materials can be present in combination with the compound of the present invention.

When the compounds of the present invention are present in combination with other phase change ink carrier materials, the compounds of the formulae

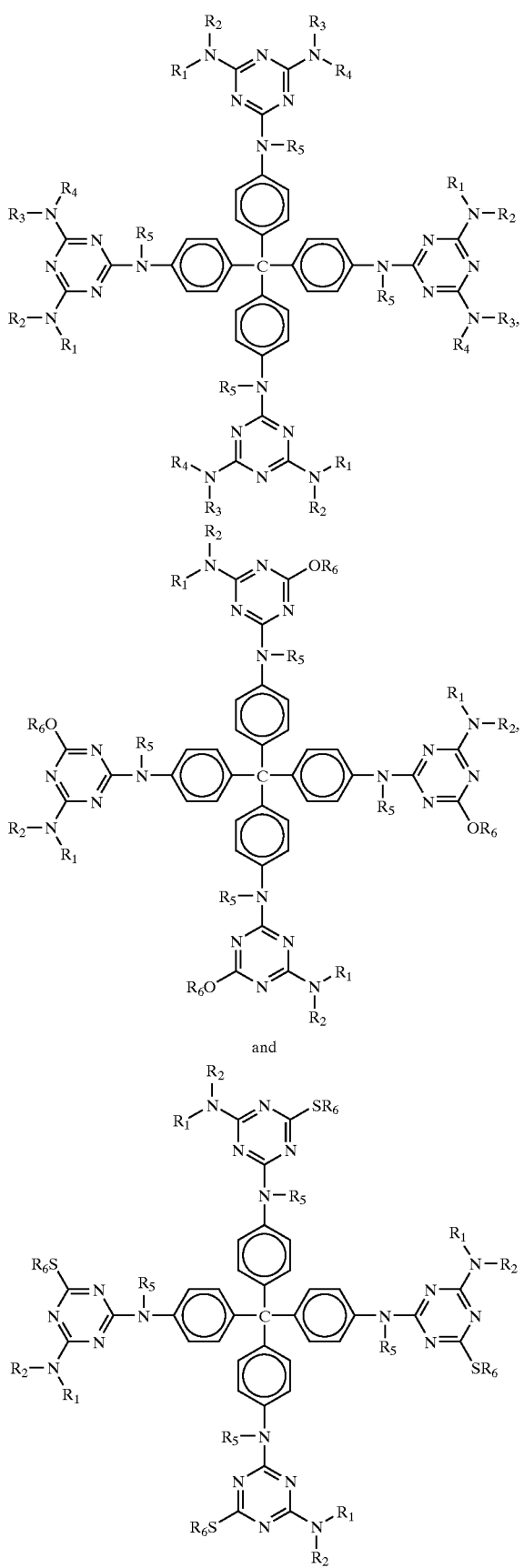

and are present in any desired or effective amount, in one embodiment at least about 0.1 percent by weight of the ink composition, in another embodiment at least about 1 percent by weight of the ink composition, in yet another embodiment at least about 5 percent by weight of the ink composition, and in still another embodiment at least about 10 percent by weight of the ink composition, and in one embodiment no more than about 40 percent by weight of the ink composition, in another embodiment no more than about 25 percent by weight of the ink composition, in yet another embodiment no more than about 20 percent by weight of the ink composition, and in still another embodiment no more than about 15 percent by weight of the ink composition, although the amount of this material in the ink can be outside of these ranges.

When other phase change ink carrier materials are used in combination with the compounds of the present invention, any desired or effective carrier composition can be used. Examples of suitable ink carrier materials include fatty amides, such as monoamides, tetra-amides, mixtures thereof, and the like. Specific examples of suitable fatty amide ink carrier materials include stearyl stearamide, a dimer acid based tetra-amide that is the reaction product of dimer acid, ethylene diamine, and stearic acid, a dimer acid based tetra-amide that is the reaction product of dimer acid, ethylene diamine, and a carboxylic acid having at least about 36 carbon atoms, and the like, as well as mixtures thereof. When the fatty amide ink carrier is a dimer acid based tetra-amide that is the reaction product of dimer acid, ethylene diamine, and a carboxylic acid having at least about 36 carbon atoms, the carboxylic acid is of the general formula

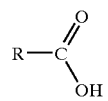

wherein R is an alkyl group, including linear, branched, saturated, unsaturated, and cyclic alkyl groups, said alkyl group in one embodiment having at least about 36 carbon atoms, in another embodiment having at least about 40 carbon atoms, said alkyl group in one embodiment having no more than about 200 carbon atoms, in another embodiment having no more than about 150 carbon atoms, and in yet another embodiment having no more than about 100 carbon atoms, although the number of carbon atoms can be outside of these ranges. Carboxylic acids of this formula are commercially available from, for example, Baker Petrolite, Tulsa, Okla., and can also be prepared as described in Example 1 of U.S. Pat. No. 6,174,937, the disclosure of which is totally incorporated herein by reference. Further information on fatty amide carrier materials is disclosed in, for example, U.S. Pat. No. 4,889,560, U.S. Pat. No. 4,889,761, U.S. Pat. No. 5,194,638, U.S. Pat. No. 4,830,671, U.S. Pat. No. 6,174,937, U.S. Pat. No. 5,372,852, U.S. Pat. No. 5,597,856, U.S. Pat. No. 6,174,937, and British Patent GB 2 238 792, the disclosures of each of which are totally incorporated herein by reference.

Also suitable as phase change ink carrier materials are isocyanate-derived resins and waxes, such as urethane isocyanate-derived materials, urea isocyanate-derived materials, urethane/urea isocyanate-derived materials, mixtures thereof, and the like. Further information on isocyanate-derived carrier materials is disclosed in, for example, U.S. Pat. No. 5,750,604, U.S. Pat. No. 5,780,528, U.S. Pat. No. 5,782,966, U.S. Pat. No. 5,783,658, U.S. Pat. No. 5,827,918, U.S. Pat. No. 5,830,942, U.S. Pat. No. 5,919,839, U.S. Pat. No. 6,255,432, U.S. Pat. No. 6,309,453, British Patent GB 2 294 939, British Patent GB 2 305 928, British Patent GB 2 305 670, British Patent GB 2 290 793, PCT Publication WO 94/14902, PCT Publication WO 97/12003, PCT Publication WO 97/13816, PCT Publication WO 96/14364, PCT Publication WO 97/33943, and PCT Publication WO 95/04760, the disclosures of each of which are totally incorporated herein by reference.

Mixtures of fatty amide materials and isocyanate-derived materials can also be employed as the ink carrier composition for inks of the present invention.

Additional suitable phase change ink carrier materials for the present invention include paraffins, microcrystalline waxes, polyethylene waxes, ester waxes, amide waxes, fatty acids, fatty alcohols, fatty amides and other waxy materials, sulfonamide materials, resinous materials made from different natural sources (such as, for example, tall oil rosins and rosin esters), and many synthetic resins, oligomers, polymers and copolymers, such as ethylene/vinyl acetate copolymers, ethylene/acrylic acid copolymers, ethylene/vinyl acetate/acrylic acid copolymers, copolymers of acrylic acid with polyamides, and the like, ionomers, and the like, as well as mixtures thereof. One or more of these materials can also be employed in a mixture with a fatty amide material and/or an isocyanate-derived material.

In one specific embodiment, the phase change ink carrier comprises the ink carrier comprises (a) a polyethylene wax, present in the ink in an amount in one embodiment of at least about 25 percent by weight of the ink, in another embodiment of at least about 30 percent by weight of the ink, and in yet another embodiment of at least about 37 percent by weight of the ink, and in one embodiment of no more than about 60 percent by weight of the ink, in another embodiment of no more than about 53 percent by weight of the ink, and in yet another embodiment of no more than about 48 percent by weight of the ink, although the amount can be outside of these ranges; (b) a stearyl stearamide wax, present in the ink in an amount in one embodiment of at least about 8 percent by weight of the ink, in another embodiment of at least about 10 percent by weight of the ink, and in yet another embodiment of at least about 12 percent by weight of the ink, and in one embodiment of no more than about 32 percent by weight of the ink, in another embodiment of no more than about 28 percent by weight of the ink, and in yet another embodiment of no more than about 25 percent by weight of the ink, although the amount can be outside of these ranges; (c) a dimer acid based tetra-amide that is the reaction product of dimer acid, ethylene diamine, and a carboxylic acid derivative of a long chain alcohol having greater than thirty six carbon atoms, present in the ink in an amount in one embodiment of at least about 10 percent by weight of the ink, in another embodiment of at least about 13 percent by weight of the ink, and in yet another embodiment of at least about 16 percent by weight of the ink, and in one embodiment of no more than about 32 percent by weight of the ink, in another embodiment of no more than about 27 percent by weight of the ink, and in yet another embodiment of no more than about 22 percent by weight of the ink, although the amount can be outside of these ranges; (d) a urethane resin derived from the reaction of two equivalents of hydroabietyl alcohol and one equivalent of isophorone diisocyanate, present in the ink in an amount in one embodiment of at least about 6 percent by weight of the ink, in another embodiment of at least about 8 percent by weight of the ink, and in yet another embodiment of at least about 10 percent by weight of the ink, and in one embodiment of no more than about 16 percent by weight of the ink, in another embodiment of no more than about 14 percent by weight of the ink, and in yet another embodiment of no more than about 12 percent by weight of the ink, although the amount can be outside of these ranges; (e) a urethane resin that is the adduct of three equivalents of stearyl isocyanate and a glycerol-based alcohol, present in the ink in an amount in one embodiment of at least about 2 percent by weight of the ink, in another embodiment of at least about 3 percent by weight of the ink, and in yet another embodiment of at least about 4.5 percent by weight of the ink, and in one embodiment of no more than about 13 percent by weight of the ink, in another embodiment of no more than about 10 percent by weight of the ink, and in yet another embodiment of no more than about 7.5 percent by weight of the ink, although the amount can be outside of these ranges; and (f) an antioxidant, present in the ink in an amount in one embodiment of at least about 0.01 percent by weight of the ink, in another embodiment of at least about 0.05 percent by weight of the ink, and in yet another embodiment of at least about 0.1 percent by weight of the ink, and in one embodiment of no more than about 1 percent by weight of the ink, in another embodiment of no more than about 0.5 percent by weight of the ink, and in yet another embodiment of no more than about 0.3 percent by weight of the ink, although the amount can be outside of these ranges.

The ink carrier is present in the phase change ink of the present invention in any desired or effective amount, in one embodiment of at least about 0.1 percent by weight of the ink, in another embodiment of at least about 50 percent by weight of the ink, and in yet another embodiment of at least about 90 percent by weight of the ink, and in one embodiment of no more than about 99 percent by weight of the ink, in another embodiment of no more than about 98 percent by weight of the ink, and in yet another embodiment of no more than about 95 percent by weight of the ink, although the amount can be outside of these ranges.

Any desired or effective colorant can be employed in the inks of the present invention, including dyes, pigments, mixtures thereof, and the like, provided that the colorant can be dissolved or dispersed in the phase change ink carrier. The phase change carrier compositions of the current invention can be used in combination with conventional phase change ink colorant materials, such as Color Index (C.I.) Solvent Dyes, Disperse Dyes, modified Acid and Direct Dyes, Basic Dyes, Sulphur Dyes, Vat Dyes, and the like. Examples of suitable dyes include Neozapon Red 492 (BASF); Orasol Red G (Ciba-Geigy); Direct Brilliant Pink B (Crompton & Knowles); Aizen Spilon Red C-BH (Hodogaya Chemical); Kayanol Red 3BL (Nippon Kayaku); Levanol Brilliant Red 3BW (Mobay Chemical); Levaderm Lemon Yellow (Mobay Chemical); Spirit Fast Yellow 3G; Aizen Spilon Yellow C-GNH (Hodogaya Chemical); Sirius Supra Yellow GD 167; Cartasol Brilliant Yellow 4GF (Sandoz); Pergasol Yellow CGP (Ciba-Geigy); Orasol Black RLP (Ciba-Geigy); Savinyl Black RLS (Sandoz); Dermacarbon 2GT (Sandoz); Pyrazol Black BG (ICI); Morfast Black Conc. A (Morton-Thiokol); Diaazol Black RN Quad (ICI); Orasol Blue GN (Ciba-Geigy); Savinyl Blue GLS (Sandoz); Luxol Blue MBSN (Morton-Thiokol); Sevron Blue 5GMF (ICI); Basacid Blue 750 (BASF), Neozapon Black X51 [C.I. Solvent Black, C.I. 12195] (BASF), Sudan Blue 670 [C.I. 61554] (BASF), Sudan Yellow 146 [C.I. 12700] (BASF), Sudan Red 462 [C.I. 26050] (BASF), Intratherm Yellow 346 from Crompton and Knowles, C.I. Disperse Yellow 238, Neptune Red Base NB543 (BASF, C.I. Solvent Red 49), Neopen Blue FF-4012 from BASF, Lampronol Black BR from ICI (C.I. Solvent Black 35), Morton Morplas Magenta 36 (C.I. Solvent Red 172), metal phthalocyanine colorants such as those disclosed in U.S. Pat. No. 6,221,137, the disclosure of which is totally incorporated herein by reference, and the like. Polymeric dyes can also be used, such as those disclosed in, for example, U.S. Pat. No. 5,621,022 and U.S. Pat. No. 5,231,135, the disclosures of each of which are totally incorporated herein by reference, and commercially available from, for example, Milliken & Company as Milliken Ink Yellow 869, Milliken Ink Blue 92, Milliken Ink Red 357, Milliken Ink Yellow 1800, Milliken Ink Black 8915-67, uncut Reactant Orange X-38, uncut Reactant Blue X-17, and uncut Reactant Violet X-80.

Pigments are also suitable colorants for the phase change inks of the present invention. Examples of suitable pigments include Violet Toner VT-8015 (Paul Uhlich); Paliogen Violet 5100 (BASF); Paliogen Violet 5890 (BASF); Permanent Violet VT 2645 (Paul Uhlich); Heliogen Green L8730 (BASF); Argyle Green XP-111-S (Paul Uhlich); Brilliant Green Toner GR 0991 (Paul Uhlich); Lithol Scarlet D3700 (BASF); Toluidine Red (Aldrich); Scarlet for Thermoplast NSD PS PA (Ugine Kuhlmann of Canada); E.D. Toluidine Red (Aldrich); Lithol Rubine Toner (Paul Uhlich); Lithol Scarlet 4440 (BASF); Bon Red C (Dominion Color Company); Royal Brilliant Red RD-8192 (Paul Uhlich); Oracet Pink RF (Ciba-Geigy); Paliogen Red 3871K (BASF); Paliogen Red 3340 (BASF): Lithol Fast Scarlet L4300 (BASF); Heliogen Blue L6900, L7020 (BASF); Heliogen Blue K6902, K6910 (BASF); Heliogen Blue D6840, D7080 (BASF); Sudan Blue OS (BASF); Neopen Blue FF4012 (BASF); PV Fast Blue B2G01 (American Hoechst); Irgalite Blue BCA (Ciba-Geigy); Paliogen Blue 6470 (BASF); Sudan III (Red Orange) (Matheson, Colemen Bell); Sudan II (Orange) (Matheson, Colemen Bell); Sudan Orange G (Aldrich), Sudan Orange 220 (BASF); Paliogen Orange 3040 (BASF); Ortho Orange OR 2673 (Paul Uhlich); Paliogen Yellow 152, 1560 (BASF); Lithol Fast Yellow 0991K (BASF); Paliotol Yellow 1840 (BASF); Novoperm Yellow FGL (Hoechst); Permanent Yellow YE 0305 (Paul Uhlich); Lumogen Yellow D0790 (BASF); Suco-Yellow L1250 (BASF); Suco-Yellow D1355 (BASF); Suco Fast Yellow D1355, D1351 (BASF); Hostaperm Pink E (American Hoechst); Fanal Pink D4830 (BASF); Cinquasia Magenta (Du Pont); Paliogen Black L0084 (BASF); Pigment Black K801 (BASF); and carbon blacks such as REGAL 330® (Cabot), Carbon Black 5250, Carbon Black 5750 (Columbia Chemical), and the like.

Also suitable as colorants are the isocyanate-derived colored resins disclosed in U.S. Pat. No. 5,780,528, the disclosure of which is totally incorporated herein by reference.

Also suitable are the colorants disclosed in Copending Application U.S. Ser. No. 10/072,241, filed Feb. 8, 2002, entitled "Phthalocyanine Compositions," Copending Application U.S. Ser. No. 10/072,210, Feb. 8, 2002, entitled "Ink Compositions Containing Phthalocyanines," Copending Application U.S. Ser. No. 10/072,237, filed Feb. 8, 2002, entitled "Methods For Preparing Phthalocyanine Compositions," Copending Application U.S. Ser. No. 10/185,261, filed Jun. 27, 2002, entitled "Processes for Preparing Dianthranilate Compounds and Diazopyridone Colorants," Copending Application U.S. Ser. No. 10/185, 994, filed Jun. 27, 2002, entitled "Dimeric Azo Pyridone Colorants," Copending Application U.S. Ser. No. 10/184, 269, filed Jun. 27, 2002, entitled "Phase Change Inks Containing Dimeric Azo Pyridone Colorants," Copending Application U.S. Ser. No. 10/185,264, filed Jun. 27, 2002, entitled "Phase Change Inks Containing Azo Pyridone Colorants," Copending Application U.S. Ser. No. 10/186, 024, filed Jun. 27, 2002, entitled "Azo Pyridone Colorants," Copending Application U.S. Ser. No. 10/185,597, filed Jun. 27, 2002, entitled "Process for Preparing Substituted Pyridone Compounds," Copending Application U.S. Ser. No. 10/185,828, filed Jun. 27, 2002, entitled "Method for Making Dimeric Azo Pyridone Colorants," Copending Application U.S. Ser. No. 10/186,023, filed Jun. 27, 2002, entitled "Dimeric Azo Pyridone Colorants," and Copending Application U.S. Ser. No. 10/184,266, filed Jun. 27, 2002, entitled "Phase Change Inks Containing Dimeric Azo Pyridone Colorants," the disclosures of each of which are totally incorporated herein by reference.

Other ink colors besides the subtractive primary colors can be desirable for applications such as postal marking or industrial marking and labeling using phase change printing, and the present invention is applicable to these needs. Further, infrared (IR) or ultraviolet (UV) absorbing dyes can also be incorporated into the inks of the present invention for use in applications such as "invisible" coding or marking of products. Examples of such infrared and ultraviolet absorbing dyes are disclosed in, for example, U.S. Pat. No. 5,378,574, U.S. Pat. No. 5,146,087, U.S. Pat. No. 5,145,518, U.S. Pat. No. 5,543,177, U.S. Pat. No. 5,225,900, U.S. Pat. No. 5,301,044, U.S. Pat. No. 5,286,286, U.S. Pat. No. 5,275,647, U.S. Pat. No. 5,208,630, U.S. Pat. No. 5,202,265, U.S. Pat. No. 5,271,764, U.S. Pat. No. 5,256,193, U.S. Pat. No. 5,385,803, and U.S. Pat. No. 5,554,480, the disclosures of each of which are totally incorporated herein by reference.

The colorant is present in the phase change ink of the present invention in any desired or effective amount to obtain the desired color or hue, in one embodiment at least about 0.1 percent by weight of the ink, in another embodiment at least about 0.5 percent by weight of the ink, and in yet another embodiment at least about 2 percent by weight of the ink, and in one embodiment no more than about 15 percent by weight of the ink, in another embodiment no more than about 8 percent by weight of the ink, and in yet another embodiment no more than about 6 percent by weight of the ink, although the amount can be outside of these ranges.

The inks of the present invention can also optionally contain an antioxidant. The optional antioxidants of the ink compositions protect the images from oxidation and also protect the ink components from oxidation during the heating portion of the ink preparation process. Specific examples of suitable antioxidants include NAUGUARD® 524, NAUGUARD® 76, and NAUGUARD® 512, commercially available from Uniroyal Chemical Company, Oxford, Conn., IRGANOX® 1010, commercially available from Ciba Geigy, and the like. When present, the optional antioxidant is present in the ink in any desired or effective amount, in one embodiment of at least about 0.01 percent by weight of the ink, in another embodiment of at least about 0.1 percent by weight of the ink, and in yet another embodiment of at least about 1 percent by weight of the ink, and in one embodiment of no more than about 20 percent by weight of the ink, in another embodiment of no more than about 5 percent by weight of the ink, and in yet another embodiment of no more than about 3 percent by weight of the ink, although the amount can be outside of these ranges.

The inks of the present invention can also optionally contain a viscosity modifier. Examples of suitable viscosity modifiers include aliphatic ketones, such as stearone, and the like. When present, the optional viscosity modifier is present in the ink in any desired or effective amount, in one embodiment of at least about 0.1 percent by weight of the ink, in another embodiment of at least about 1 percent by weight of the ink, and in yet another embodiment of at least about 10 percent by weight of the ink, and in one embodiment of no more than about 99 percent by weight of the ink, in another embodiment of no more than about 30 percent by weight of the ink, and in yet another embodiment of no more than about 15 percent by weight of the ink, although the amount can be outside of these ranges.

Other optional additives to the inks include clarifiers, such as UNION CAMP® X37-523-235 (commercially available from Union Camp), in an amount in one embodiment of at least about 0.01 percent by weight of the ink, in another embodiment of at least about 0.1 percent by weight of the ink, and in yet another embodiment of at least about 5 percent by weight of the ink, and in one embodiment of no more than about 98 percent by weight of the ink, in another embodiment of no more than about 50 percent by weight of the ink, and in yet another embodiment of no more than about 10 percent by weight of the ink, although the amount can be outside of these ranges, tackifiers, such as FORAL® 85, a glycerol ester of hydrogenated abietic (rosin) acid (commercially available from Hercules), FORAL® 105, a pentaerythritol ester of hydroabietic (rosin) acid (commercially available from Hercules), CELLOLYN® 21, a hydroabietic (rosin) alcohol ester of phthalic acid (commercially available from Hercules), ARAKAWA KE-311 Resin, a triglyceride of hydrogenated abietic (rosin) acid (commercially available from Arakawa Chemical Industries, Ltd.), synthetic polyterpene resins such as NEVTAC® 2300, NEVTAC® 100, and NEVTAC® 80 (commercially available from Neville Chemical Company), WINGTACK® 86, a modified synthetic polyterpene resin (commercially available from Goodyear), and the like, in an amount in one embodiment of at least about 0.1 percent by weight of the ink, in another embodiment of at least about 5 percent by weight of the ink, and in yet another embodiment of at least about 10 percent by weight of the ink, and in one embodiment of no more than about 98 percent by weight of the ink, in another embodiment of no more than about 75 percent by weight of the ink, and in yet another embodiment of no more than about 50 percent by weight of the ink, although the amount can be outside of these range, adhesives, such as VERSAMID® 757, 759, or 744 (commercially available from Henkel), in an amount in one embodiment of at least about 0.1 percent by weight of the ink, in another embodiment of at least about 1 percent by weight of the ink, and in yet another embodiment of at least about 5 percent by weight of the ink, and in one embodiment of no more than about 98 percent by weight of the ink, in another embodiment of no more than about 50 percent by weight of the ink, and in yet another embodiment of no more than about 10 percent by weight of the ink, although the amount can be outside of these ranges, plasticizers, such as UNIPLEX® 250 (commercially available from Uniplex), the phthalate ester plasticizers commercially available from Monsanto under the trade name SANTICIZER®, such as dioctyl phthalate, diundecyl phthalate, alkylbenzyl phthalate (SANTICIZER® 278), triphenyl phosphate (commercially available from Monsanto), KP-140®, a tributoxyethyl phosphate (commercially available from FMC Corporation), MORFLEX® 150, a dicyclohexyl phthalate (commercially available from Morflex Chemical Company Inc.), trioctyl trimellitate (commercially available from Eastman Kodak Co.), and the like, in an amount in one embodiment of at least about 0.1 percent by weight of the ink, in another embodiment of at least about 1 percent by weight of the ink, and in yet another embodiment of at least about 2 percent by weight of the ink, and in one embodiment of no more than about 50 percent by weight of the ink, in another embodiment of no more than about 30 percent by weight of the ink, and in yet another embodiment of no more than about 10 percent by weight of the ink, although the amount can be outside of these ranges, and the like.

Optionally, the inks of the present invention contain a component that, in its pure form, is a liquid at room temperature (typically about 20° C.), but, when incorporated into the inks of the present invention, enable the ink to be a solid at 35° C. or higher. The selected liquid or mixture of liquids are chosen to be compatible with the other ink components, and can be either polar or nonpolar in nature. Specific examples of suitable liquids include aliphatic hydrocarbons, including those with boiling points of about 150° C. or higher, such as squalene, ISOPAR® V, and the like, polar liquids such as glycol ethers, esters, amides, alcohols, and the like, with specific examples including butyl carbitol, tripropylene glycol monomethyl ether, 1-phenoxy-2-propanol, dibutyl phthalate, dibutyl sebacate, 1-dodecanol, and the like, as well as mixtures thereof.

The ink compositions of the present invention typically are solid at temperatures of about 35° C. and lower, preferably solid at temperatures of 50° C. and lower, more preferably solid at temperatures of about 70° C. and lower, and even more preferably solid at temperatures of about 80° C. and lower, and typically have viscosity values of from about 5 to 30 centipoise at temperatures no higher than about 160° C., preferably no higher than about 140° C., and more preferably no higher than about 120° C., although the temperature at which these viscosities are achieved can be outside of these ranges.

The ink compositions of the present invention generally have viscosities at the jetting temperature (typically no lower than about 75° C., preferably no lower than about 100° C., and more preferably no lower than about 120° C., and typically no higher than about 180° C., preferably no higher than about 150° C., and more preferably no higher than about 130° C., although the jetting temperature can be outside of these ranges) typically of no more than about 30 centipoise, preferably no more than about 20 centipoise, and even more preferably no more than about 15 centipoise, and typically of no less than about 2 centipoise, preferably no less than about 5 centipoise, and even more preferably no less than about 7 centipoise, although the melt viscosity can be outside of these ranges.

The ink compositions of the present invention can be prepared by any desired or suitable method. For example, the ink ingredients can be mixed together, followed by heating, typically to a temperature of from about 100 to about 140° C., although the temperature can be outside of this range, and stirring or milling until a homogeneous ink composition is obtained, followed by cooling the ink to ambient temperature (typically from about 20 to about 25° C.). The inks of the present invention are solid at ambient temperature.

The present invention is also directed to a process which entails incorporating an ink of the present invention into an ink jet printing apparatus, melting the ink, and causing droplets of the melted ink to be ejected in an imagewise pattern onto a recording sheet. In one specific embodiment, the printing apparatus employs a piezoelectric printing process wherein droplets of the ink are caused to be ejected in imagewise pattern by oscillations of piezoelectric vibrating elements. In another specific embodiment, the droplets of melted ink are caused to be ejected onto an intermediate transfer member, followed by transfer of the image from the intermediate transfer member to a recording sheet. In a specific embodiment, the intermediate transfer member is heated to a temperature above that of the final recording sheet and below that of the melted ink in the printing apparatus. Inks of the present invention can also be employed in other hot melt printing processes, such as hot melt thermal ink jet printing, hot melt continuous stream or deflection ink jet printing, hot melt acoustic ink jet printing, or the like.

Any suitable substrate or recording sheet can be employed, including plain papers such as Xerox® 4024 papers, Xerox® Image Series papers, Courtland 4024 DP paper, ruled notebook paper, bond paper, silica coated papers such as Sharp Company silica coated paper, JuJo paper, and the like, transparency materials, fabrics, textile products, plastics, polymeric films, inorganic substrates such as metals and wood, and the like. In a preferred embodiment, the process entails printing onto a porous or ink absorbent substrate, such as plain paper.

Specific embodiments of the invention will now be described in detail. These examples are intended to be illustrative, and the invention is not limited to the materials, conditions, or process parameters set forth in these embodiments. All parts and percentages are by weight unless otherwise indicated.

SYNTHESIS OF STARTING MATERIALS

EXAMPLE A

Synthesis of Tetraphenylmethane

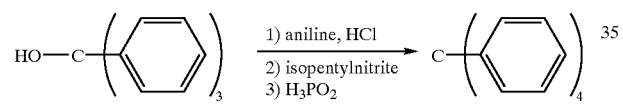

In a 1 liter round-bottom flask, triphenylmethanol (26.0 grams, 0.100 mol; obtained from Aldrich Chemical Co., Milwaukee, Wis.) and aniline (14.6 milliliters, 0.160 mol) were added to a solution of concentrated aqueous hydrochloric acid (47 milliliters) in acetic acid (312 milliliters). The resulting solution was stirred and heated at reflux for 48 hours. The yellow solution was then cooled to room temperature and solvents were removed by evaporation under reduced pressure. Ethanol (700 milliliters) was added to dissolve all the off-white solid residue, and the stirred solution was cooled to −10° C. Sulfuric acid (52 milliliters) was then added, and the cold mixture was stirred for 20 minutes. Isopentylnitrite (31.2 milliliters; obtained from Aldrich Chemical Co.) was then added and the solution was stirred for an additional 20 minutes. Thereafter, hypophosphorous acid (89 milliliters, 50 percent by weight aqueous solution; obtained from Aldrich Chemical Co.) was added, still at −10° C., and the solution was gradually heated to reflux and stirred for 2 hours. The mixture was then cooled to room temperature, giving an off-white precipitate, which was recovered by filtration, successively washed with water, hexanes, methanol, ethanol, methanol, and finally with pentane, and dried under reduced pressure to give the targeted tetraphenylmethane as a colorless solid (28.0 grams, 90 percent yield).

EXAMPLE B

Synthesis of Tetrakis(4-nitrophenyl)methane

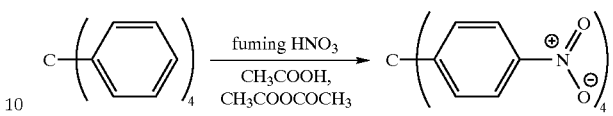

In a 500 milliliter round-bottom flask, 125 milliliters of fuming nitric acid (≧90 percent) was cooled to −40° C. Tetraphenylmethane (25 grams, 78 mmol; prepared as described in Example A) was slowly added to the stirred solution at a rate that maintained the temperature of the mixture below −20° C. When the addition was completed, a mixture of acetic anhydride (47 milliliters; obtained from Anachemia, Montreal, QC) and acetic acid (90 milliliters) was added to the resulting brown sludge, and the stirred mixture was warmed to room temperature, giving a yellow precipitate. More acetic acid was added (173 milliliters), and the precipitate was isolated by filtration and successively washed with acetic acid, methanol, hexanes, and pentane. The resulting yellow powder was dried under reduced pressure, giving the targeted tetrakis(4-nitrophenyl)methane in a 64 percent yield (24.8 grams).

EXAMPLE C

Synthesis of Tetrakis(4-aminophenyl)methane

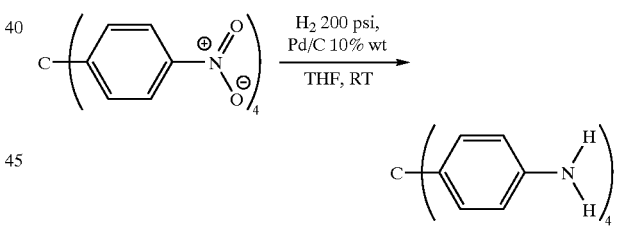

In a Parr reactor, tetrakis(4-nitrophenyl)methane (17.0 grams, 34.0 mmol; prepared as described in Example B) and palladium, weight percent on activated carbon (2.15 grams, 2.00 mmol; obtained from Aldrich Chemical Co., Milwaukee, Wis.) were added to tetrahydrofuran (450 milliliters). The reactor was closed, and the mixture was stirred under 200 pounds per square inch (13.6 atmospheres) of hydrogen pressure for 72 hours at room temperature. The mixture was then filtered through CELITE, solvent was removed from the filtrate by evaporation under reduced pressure, and the resulting white solid was triturated in chloroform. The solid was then recovered by filtration, washed with chloroform again, and dried under reduced pressure at room temperature to give the targeted tetrakis (4-aminophenyl)methane as a white powder in a quantitative yield (12.9 grams).

EXAMPLE D

Synthesis of Tetrakis[4[(2,4-dichloro-1,3,5-triazin-6-yl)amino]phenyl]methane

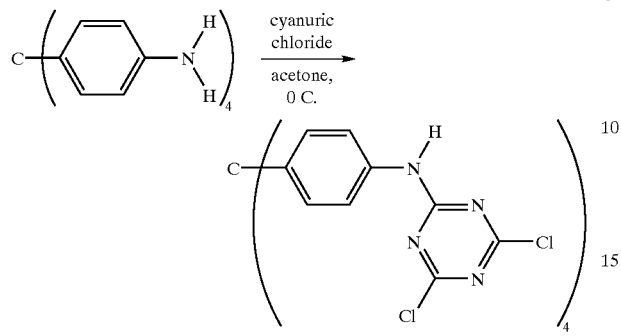

A solution of tetrakis(4-aminophenyl)methane (4.57 grams, 12.0 mmol; prepared as described in Example C) in acetone (96 milliliters) was added dropwise at 0° C. to a stirred solution of cyanuric chloride (9.06 grams, 49.1 mmol; obtained from Aldrich Chemical Co., Milwaukee, Wis.) in acetone (144 milliliters). The resulting mixture was kept at 0° C. for 1 hour, treated with $Na_2CO_3$ (5.21 grams, 49.2 mmol), and poured into water (960 milliliters). The precipitate was separated by filtration, washed with water, and dried to give the tetrakis[4-[(2,4-dichloro-1,3,5-triazin-6-yl)amino]phenyl]methane (7.97 grams, 8.20 mmol, 68 percent yield) as a colorless solid: mp>310° C.; $^1$H NMR (400 MHz, DMSO-$d_6$, 25° C.) δ 7.18 (d, 8H, $^3J$=8.7 Hz), 7.55 (d, 8H, $^3J$=8.7 Hz), 11.18 (s, 4H); $^{13}$C NMR (75.4 MHz, DMSO-$d_6$, 25° C.) δ 64.1, 121.7, 131.7, 135.8, 143.8, 164.6, 169.7, 170.7; MS (FAB, 2-nitrobenzyl alcohol) m/e 969. Anal. Calcd for $C_{37}H_{20}Cl_8N_{16}$: C, 45.71; H, 2.07; N, 23.05. Found: C, 46.03; H, 2.09; N, 22.61.

GENERAL SYNTHESIS OF TETRAKIS[4[(N-[4,6-BIS(ALKYLAMINO)-1,3,5-TRIAZIN-2-YL)AMINO]PHENYL]METHANE DERIVATIVES FROM TETRAKIS[4[(2,4-DICHLORO-1,3,5-TRIAZIN-6-YL)AMINO]PHENYL]METHANE

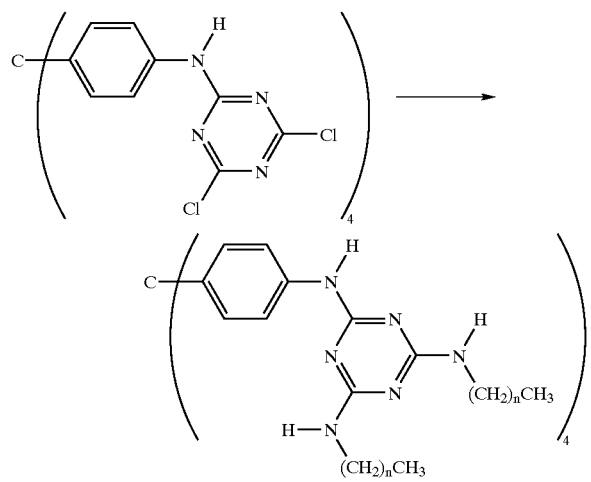

In a 250 milliliter round-bottom flask at room temperature an alkylamine (18 equivalents) was added to a solution of tetrakis[4[(2,4-dichloro-1,3,5-triazin-6-yl)amino]phenyl] methane (7.63 grams, 7.85 mmol; prepared as described in Example D) in tetrahydrofuran (90 milliliters). The stirred mixture was then heated at reflux for 4 hours. Volatiles were removed by evaporation under reduced pressure. The residual solid was dissolved in chloroform, and the organic phase was extracted with aqueous 3 Molar hydrochloric acid and aqueous 1 Molar sodium hydroxide, and was finally washed with water until neutral. The organic solution was finally dried over $Na_2SO_4$, and solvent was removed by evaporation under reduced pressure. The resulting white solid was dried under reduced pressure to give the targeted tetrakis[4[(N-[4,6-bis(alkylamino)-1,3,5-triazin-2-yl)amino]phenyl]methane.

GENERAL SYNTHESIS OF TETRAKIS[4[(N-[4,6-BIS(ALKYLAMINO)-1,3,5-TRIAZIN-2-YL)AMINO]PHENYL]METHANE DERIVATIVES FROM TETRAKIS(4-AMINOPHENYL)METHANE

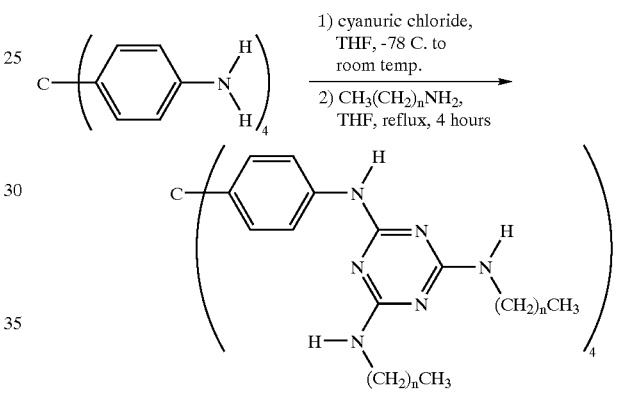

In a 100 milliliter round-bottom flask at −78° C., tetrakis(4-aminophenyl)methane (380 milligrams, 1.00 mmol; prepared as described in Example C) in tetrahydrofuran (20 milliliters) was added dropwise to a stirred solution of cyanuric chloride (812 milligrams, 4.40 mmol; obtained from Aldrich Chemical Co., Milwaukee, Wis.) in tetrahydrofuran (20 milliliters). The resulting mixture was gradually warmed to room temperature, 25 equivalents of the corresponding alkylamine was added, and the mixture was stirred at reflux for 2 hours. The mixture was then cooled to room temperature, solvent was removed under reduced pressure, the residue was dissolved in chloroform, and the organic phase was extracted with aqueous 3 Molar hydrochloric acid and aqueous 1 Molar sodium hydroxide, and was finally washed with water until neutral. Solvent was removed from the organic phase under reduced pressure, and the residue was triturated in methanol, and washed with water, methanol, and pentane. The targeted compound was finally purified by column chromatography on $SiO_2$ using successively chloroform and ethyl acetate as eluant.

This method gave tetrakis[4[(N-[4,6-bis(octylamino)-1,3,5-triazin-2-yl)amino]phenyl]methane from tetrakis(4-aminophenyl)methane, cyanuric chloride, and octylamine in a 72 percent yield.

EXAMPLE I

Synthesis of Tetrakis[4[(N-[4,6-bis(butylamino)-1,3,5-triazin-2-yl)amino]phenyl]methane

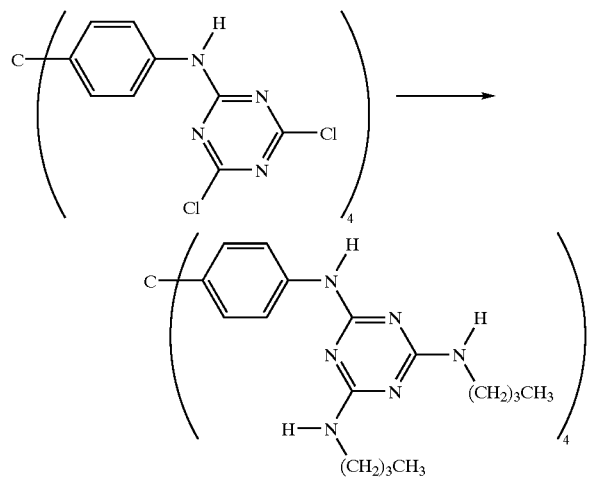

Tetrakis[4[(N-[4,6-bis(butylamino)-1,3,5-triazin-2-yl)amino]phenyl]methane was prepared according to the general procedure described herein using butylamine (obtained from Aldrich Chemical Co., Milwaukee, Wis.). Purification was achieved in the following way. The crude product was triturated with methanol/water, and the precipitate was recovered by filtration, washed with methanol, triturated in acetone, isolated by filtration, and finally dried under reduced pressure to give a white powder in an 89 percent yield. Softening point=175–200° C. $^1$H NMR (DMSO-d$_6$, 373 K) δ: 8.33 (s, 4H); 7.66 (d, 8H, J=8.8 Hz); 6.98 (d, 8H, J=8.8 Hz); 6.23 (m, 8H); 3.26 (m, 16H); 1.52 (m, 16H); 1.32 (m, 16H); 0.89 (t, 24H, J=7.2 Hz). $^{13}$C NMR (DMSO-d$_6$, 373 K) δ: 165.7; 164.0; 139.7; 138.5; 130.4; 118.3; 62.2; 39.2; 31.6; 19.8; 13.9. IR (KBr): 3413; 3276; 2956; 2929; 2869; 1571; 1507; 1416; 1362; 1236; 1187; 1168; 1115; 809 cm$^{-1}$. MS (MALDI TOF): 1266; 296. Anal. Calcd for C$_{69}$H$_{100}$N$_{24}$: C, 65.48; H, 7.96; N, 26.56. Found: C, 65.31; H, 8.13; N, 26.32.

EXAMPLE II

Synthesis of Tetrakis[4[(N-[4,6-bis(octylamino)-1,3,5-triazin-2-yl)amino]phenyl]methane

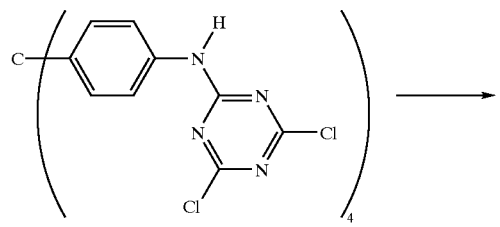

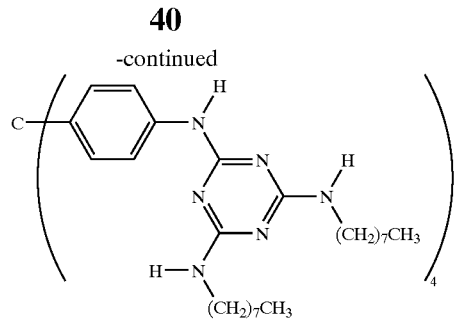

Tetrakis[4[(N-[4,6-bis(octylamino)-1,3,5-triazin-2-yl)amino]phenyl]methane was prepared according to the general procedure described herein using octylamine (obtained from Aldrich Chemical Co., Milwaukee, Wis.). 89 percent yield. Softening point=130–133° C. $^1$H NMR (DMSO-d$_6$, 373 K) δ: 88.29 (s, 4H); 7.65 (d, 8H, J=8.9 Hz); 6.98 (d, 8H, J=8.9 Hz); 6.21 (m, 8H); 3.25 (m, 16H); 1.52 (m, 16H); 1.27 (m, 80H); 0.84 (t, 24H, J=6.7 Hz). $^{13}$C NMR (DMSO-d$_6$, 373 K) δ: 165.6; 163.8; 139.6; 138.0; 129.9; 117.8; 61.5; 39.2; 30.7; 29.0; 28.3; 28.1; 26.0; 21.4; 13.1. IR (KBr): 3442; 3270; 2928; 2856; 1573; 1507; 1419; 1359; 1215; 810 cm$^{-1}$. MS (MALDI TOF): 1715. Anal. Calcd for C$_{101}$H$_{164}$N$_{24}$: C, 70.75; H, 9.64; N, 19.61. Found: C, 70.90; H, 10.21; N, 19.54.

EXAMPLE III

Synthesis of Tetrakis[4[(N-[4,6-bis(decylamino)-1,3,5-triazin-2-yl)amino]phenyl]methane

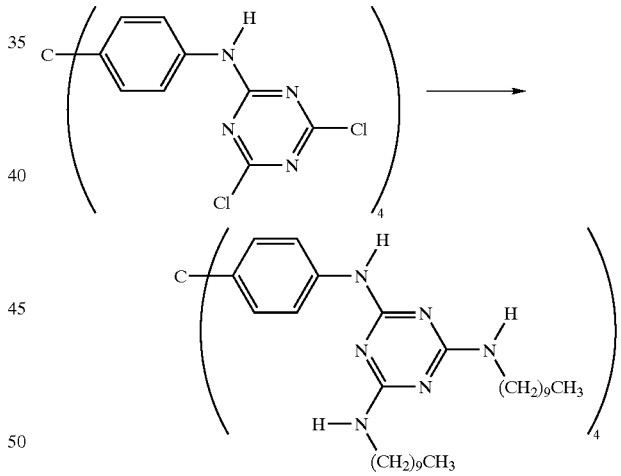

Tetrakis[4[(N-[4,6-bis(decylamino)-1,3,5-triazin-2-yl)amino]phenyl]methane was prepared according to the general procedure described herein using decylamine (obtained from Aldrich Chemical Co., Milwaukee, Wis.). 80 percent yield. Softening point=115–128° C. $^1$H NMR (DMSO-d$_6$, 373 K) δ: 8.23 (s, 4H); 7.65 (d, 8H, J=8.9 Hz); 6.99 (d, 8H, J=8.9 Hz); 6.16 (m, 8H); 3.25 (m, 16H); 1.52 (m, 16H); 1.24 (m, 112H); 0.84 (t, 24H, J=6.7 Hz). $^{13}$C NMR (DMSO-d$_6$, 373 K) δ: 165.5; 163.7; 139.5; 137.8; 129.7; 1 17.7; 61.9; 39.6; 30.6; 28.8; 28.3; 28.2; 28.2; 27.9; 25.9; 21.3; 13.0. IR (KBr): 3431, 3404; 3269; 3168; 2954; 2923; 2853; 1574; 1503; 1415; 1355; 1234; 1186; 810 cm$^{-1}$. MS (MALDI TOF): 1715. Anal. Calcd for C$_{117}$H$_{196}$N$_{24}$: C, 72.47; H, 10.19; N, 17.34. Found: C, 72.35; H, 10.25; N, 17.36.

EXAMPLE IV

Synthesis of Tetrakis[4[(N-[6-amino-2-chloro-1,3,5-triazin-4-yl)amino]phenyl]methane

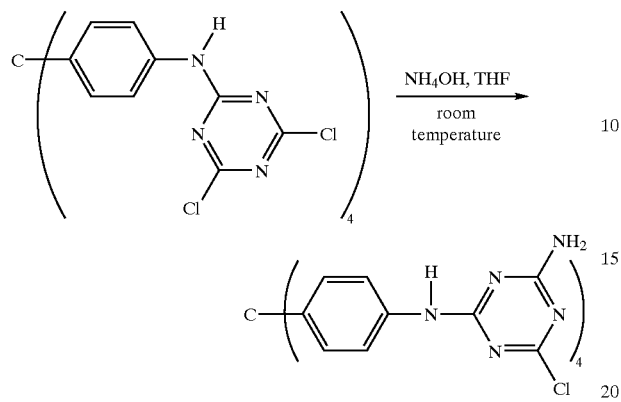

In a 250 milliliter round-bottom flask, a stirred solution of tetrakis[4[(2,4-dichloro-1,3,5-triazin-6-yl)amino]phenyl]methane (1.900 grams, 1.954 mmol; prepared as described in Example D) in tetrahydrofuran (80 milliliters) was cooled to 0° C. and was treated dropwise with aqueous ammonium hydroxide (30 percent by weight, 35 milliliters). The resulting mixture was then stirred at 25° C. for 16 hours. Volatiles were then removed by evaporation under reduced pressure, and the residue was washed with water, filtered, rinsed again with water, and finally dried under reduced pressure to give the targeted tetrakis[4[(N-[6-amino-2-chloro-1,3,5-triazin-4-yl)amino]phenyl]methane (1.748 grams, 1.953 mmol) in quantitative yield as an off-white powder.

EXAMPLE V

Synthesis of Tetrakis[4[(N-[6-amino-4-(octylamino)-1,3,5-triazin-2-yl)amino]phenyl]methane

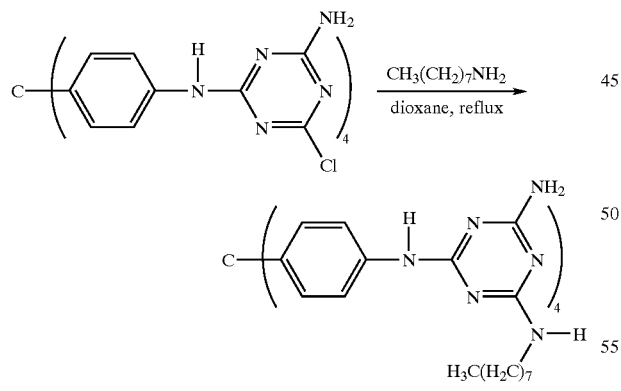

In a 250 milliliter round-bottom flask, octylamine (8.0 milliliters, 50 mmol; obtained from Aldrich Chemical Co., Milwaukee, Wis.) was added to a suspension of tetrakis[4[(N-[6-amino-2-chloro-1,3,5-triazin-4-yl)amino]phenyl]methane (1.750 grams, 1.956 mmol; prepared as described in Example IV) in dioxane (65 milliliters). The stirred mixture was heated at reflux for 2 hours. Dioxane was then removed by evaporation under reduced pressure, and the remaining residue triturated in acetone (50 milliliters). The solid was then filtered off, washed with acetone, redissolved in chloroform, and precipitated with methanol. The resulting precipitate was recovered by filtration, rinsed with methanol, and dried under reduced pressure to give tetrakis[4[(N-[6-amino-4-(octylamino)-1,3,5-triazin-2-yl)amino]phenyl]methane (2.129 grams, 1.682 mmol) as an off-white powder, 86 percent yield. Softening point=171–179° C. $^1$H NMR (DMSO-$d_6$, 373 K) δ: 8.37 (s, 4H); 7.66 (d, 8H, J=9.0 Hz); 6.99 (d, 8H, J=9.0 Hz); 6.26 (m, 4H); 5.83 (s, 8H); 3.24 (m, 8H); 1.51 (m, 8H); 1.25 (m, 40H); 0.84 (t, 12H, J=6.9 Hz). $^{13}$C NMR (DMSO-$d_6$, 373 K) δ: 166.6; 165.9; 164.1; 139.5; 137.8; 129.8; 117.8; 62.0; 39.6; 30.5; 28.8; 28.1; 27.9; 25.9; 21.3; 13.0. IR (KBr): 3405; 2925; 2853; 1571; 1507; 1464; 1415; 1369; 1237; 1187; 811 cm$^{-1}$. MS (MALDI TOF): 1265. Anal. Calcd for $C_{69}H_{100}N_{24}$: C, 64.98; H, 8.10; N, 26.03. Found: C, 65.46; H, 7.97; N, 26.57.

EXAMPLE VI

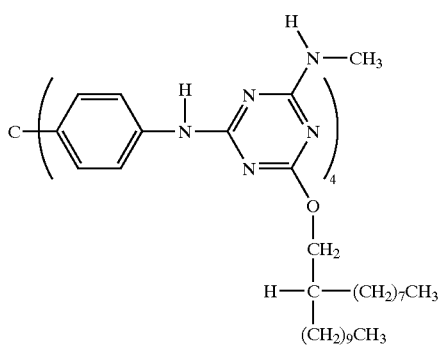

Tetrakis[4[(N-[6-amino-2-chloro-1,3,5-triazin-4-yl)amino]phenyl]methane is prepared as described in Example IV. This compound is then reacted with sodium dodecyloxide in a solvent such as tetrahydrofuran, dioxane, dimethylformamide, or the like at a temperature of from about 50 to about 60° C. to obtain the desired product.

EXAMPLE VII

A compound of the formula is prepared as follows.

Part A

Cyanuric chloride is reacted with a compound of the formula

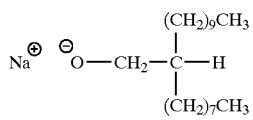

in diethyl ether at 0° C. to obtain a compound of the formula

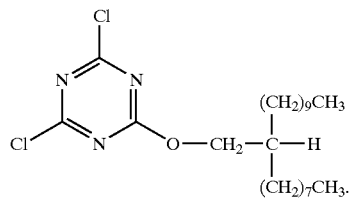

Part B

A solution of tetrakis(4-aminophenyl)methane, of the formula

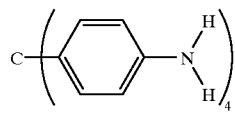

(prepared as described in Example C) in acetone is added dropwise at 0° C. to a stirred solution of the compound of the formula

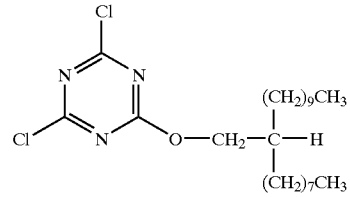

prepared in Part A of this Example in acetone. The resulting mixture is kept at 0° C. for 1 hour, treated with $Na_2CO_3$, and poured into water. The precipitate is separated by filtration, washed with water, and dried to give a product of the formula

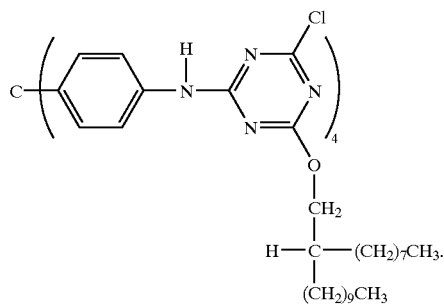

Part C

The compound of the formula

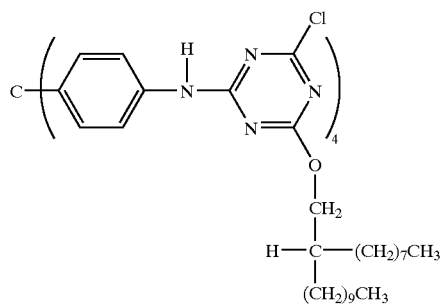

prepared in Part C of this Example is reacted with aminomethane ($CH_3NH_2$) in tetrahydrofuran or dioxane at a temperature of from about 50 to about 60° C. to give a product of the formula

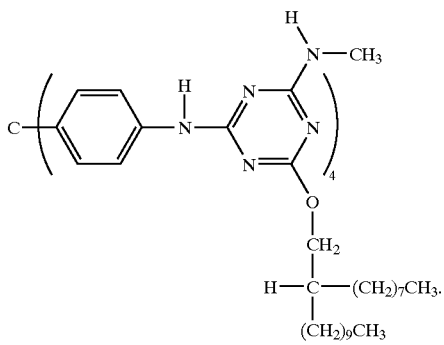

A compound of the formula

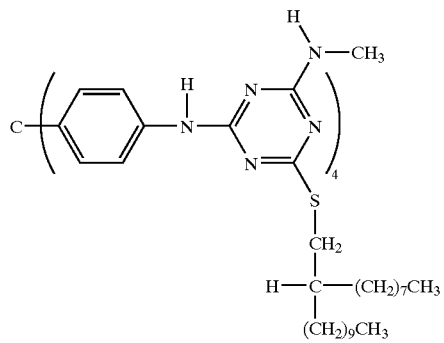

is prepared by an analogous procedure.

EXAMPLE VIII

Colorless ink compositions containing the materials prepared in Examples I, II, and III and, for comparison purposes, an ink that did not contain any of these additives were prepared as follows.

Ink A: In a stainless steel beaker were combined (1) polyethylene wax (PE 655, obtained from Baker Petrolite, Tulsa, Okla., of the formula $CH_3(CH_2)_{50}CH_3$), (2) stearyl stearamide wax (KEMAMIDE® S-180, obtained from Crompton Corporation, Greenwich, Conn.), (3) a tetra-amide resin obtained from the reaction of one equivalent of dimer acid with two equivalents of ethylene diamine and UNICID® 700 (obtained from Baker Petrolite, Tulsa, Okla., a carboxylic acid derivative of a long chain alcohol), prepared as described in Example 1 of U.S. Pat. No. 6,174,937, the disclosure of which is totally incorporated herein by reference, (4) a urethane resin obtained from the reaction of two equivalents of ABITOL® E hydroabietyl alcohol (obtained from Hercules Inc., Wilmington, Del.), and one equivalent of isophorone diisocyanate, prepared as described in Example 1 of U.S. Pat. No. 5,782,966, the disclosure of which is totally incorporated herein by reference, (5) a urethane resin that was the adduct of three equivalents of stearyl isocyanate and a glycerol-based alcohol prepared as described in Example 4 of U.S. Pat. No. 6,309,453, the disclosure of which is totally incorporated herein by reference, and (6) NAUGUARD® 445 antioxidant (obtained from Uniroyal Chemical Co., Middlebury, Conn.). The materials were melted together at a temperature of about 135° C. in an oven, then blended by stirring in a temperature controlled mantle at about 135° C. for about 0.2 hour. To this mixture was then added (6) the material prepared in Example I. After stirring for about 2 additional hours, the ink thus formed was filtered through a heated MOTT® apparatus (obtained from Mott Metallurgical) using NAE 0.2 micro filter and Whatman #3 filter paper (on top of NAE filter) under a pressure of about 15 pounds per square inch. The filtered phase change ink was poured into an aluminum mold and allowed to solidify to form an ink block. The colorless phase change ink thus prepared exhibited a viscosity of about 13.4 centipoise as measured by a Rheometrics cone-plate viscometer at about 140° C., melting points of about 86° C. and 104° C. as measured by differential scanning calorimetry using a DSC 7 from Perkin Elmer, and a glass transition temperature ($T_g$) of about 14° C.

Ink B: Ink B was prepared in a similar manner to that used to prepare Ink A but using the material prepared in Example II instead of the material prepared in Example I.

Ink C: Ink C was prepared in a similar manner to that used to prepare Ink A but using the material prepared in Example III instead of the material prepared in Example I.

Ink D: Ink D was prepared in a similar manner to that used to prepare Ink A but no additive such as those prepared in Examples I through III was present.

Relative amounts of the ingredients in each of these inks, expressed in percent by weight of the ink, are indicated in the table below:

| Ingredient | Ink A | Ink B | Ink C | Ink D |
|---|---|---|---|---|
| POLYWAX | 34.64 | 34.64 | 34.64 | 38.30 |
| S-180 | 19.00 | 19.00 | 19.00 | 21.20 |
| Tetra-amide | 19.22 | 19.22 | 19.22 | 21.40 |
| Urethane Resin 1* | 10.73 | 10.73 | 10.73 | 11.96 |
| Urethane Resin 2* | 6.23 | 6.23 | 6.23 | 6.94 |
| Example I material | 10.00 | — | — | — |
| Example II material | — | 10.00 | — | — |
| Example III material | — | — | 10.00 | — |
| NAUGUARD 445 | 0.18 | 0.18 | 0.18 | 0.20 |
| Total | 100.0 | 100.0 | 100.0 | 100.0 |

*ABITOL E based urethane resin
**glycerol alcohol based urethane resin

Dynamic mechanical analysis data were obtained to produce evidence of increased toughness of inks according to the present invention. Particularly, the toughness as well as the Young's modulus and flexural strength of ink samples were estimated by typical stress-strain measurements at room temperature using a Solid State Analyzer, RSAII from Rheometrics Scientific. The samples tested were prepared as follows: the ink was put into a pan and was melted on a hotplate at 150° C. It was then transferred onto a rectangular mold that was sitting on a hot plate at 80° C. The mold was then covered with a flat glass plate and allowed to sit for 10 minutes at 80° C. The sample was then removed from the mold and allowed to cool to room temperature. The samples obtained were rectangular, with a length of 49 millimeters, a width of 12 millimeters, and a thickness of 3 millimeters. The dynamic mechanical experiment performed was a dynamic strain rate at 23° C. using a three-point bending geometry configuration. The variation of the stress versus the applied deformation or strain was recorded. The slope from the curve stress versus strain is equal to the Young's modulus, the area under the curve is proportional to the toughness, and the stress value at which the sample breaks is the flexural strength. Inks A through C were found to have a toughness value of about 6,000 while Ink D had a toughness value of about 4,500 under the same conditions. The flexural strength was found to be about 6.0 Mpa for Inks A through C, while Ink D had a flexural strength of about 4.8.

EXAMPLE IX

Yellow ink compositions containing the materials prepared in Examples I through III and, for comparison purposes, an ink that does not contain any of these additives are prepared as follows.

Ink E: In a stainless steel beaker are combined (1) polyethylene wax (PE 655, obtained from Baker Petrolite, Tulsa, Okla., of the formula $CH_3(CH_2)_{50}CH_3$), (2) stearyl stearamide wax (KEMAMIDE® S-180, obtained from Crompton Corporation, Greenwich, Conn.), (3) a tetra-amide resin obtained from the reaction of one equivalent of dimer acid with two equivalents of ethylene diamine and UNICID® 700 (obtained from Baker Petrolite, Tulsa, Okla., a carboxylic acid derivative of a long chain alcohol), prepared as described in Example 1 of U.S. Pat. No. 6,174,937, the disclosure of which is totally incorporated herein by reference, (4) a urethane resin obtained from the reaction of two equivalents of ABITOL® E hydroabietyl alcohol (obtained from Hercules Inc., Wilmington, Del.), and one equivalent of isophorone diisocyanate, prepared as described in Example 1 of U.S. Pat. No. 5,782,966, the disclosure of which is totally incorporated herein by reference, (5) a urethane resin that was the adduct of three equivalents of stearyl isocyanate and a glycerol-based alcohol prepared as described in Example 4 of U.S. Pat. No. 6,309,453, the disclosure of which is totally incorporated herein by reference, and (6) NAUGUARD® 445 antioxidant (obtained from Uniroyal Chemical Co., Middlebury, Conn.). The materials are melted together at a temperature of about 135° C. in an oven, then blended by stirring in a temperature controlled mantle at about 135° C. for about 0.2 hour. To this mixture is then added (6) the material prepared in Example I and (7) NEOPEN YELLOW 075 (obtained from BASF). After stirring for about 2 additional hours, the yellow ink thus formed is filtered through a heated MOTT® apparatus (obtained from Mott Metallurgical) using NAE 0.2 micro filter and Whatman #3 filter paper (on top of NAE filter) under a pressure of about 15 pounds per square inch. The filtered phase change ink is poured into an aluminum mold and allowed to solidify to form an ink block. The yellow phase change ink thus prepared exhibits a viscosity of about 13.4 centipoise as measured by a Rheometrics cone-plate viscometer at about 140° C., melting points of about 86° C. and 104° C. as measured by differential scanning calorimetry using a DSC 7 from Perkin Elmer, a glass transition temperature ($T_g$) of about 14° C., and a spectral strength, determined by using a spectrophotographic procedure based on the measurement of the colorant in solution by dissolving the solid ink in n-butanol and measuring the absorbance using a Perkin Elmer Lambda 2S UV/VIS spectrophotometer, of about 3500 milliliters absorbance per gram at 429 nanometers.

Ink F: Ink F is prepared in a similar manner to that used to prepare Ink E but using the material prepared in Example II instead of the material prepared in Example I.

Ink G: Ink G is prepared in a similar manner to that used to prepare Ink E but using the material prepared in Example III instead of the material prepared in Example I.

Ink H: Ink H is prepared in a similar manner to that used to prepare Ink E but no additive such as those prepared in Examples I through III was present.

Relative amounts of the ingredients in each of these inks, expressed in percent by weight of the ink, are indicated in the table below:

| Ingredient | Ink E | Ink F | Ink G | Ink H |
|---|---|---|---|---|
| POLYWAX | 33.92 | 33.92 | 33.92 | 37.48 |
| S-180 | 18.59 | 18.59 | 18.59 | 20.73 |
| Tetra-amide | 18.80 | 18.80 | 18.80 | 20.95 |
| Urethane Resin 1* | 10.49 | 10.49 | 10.49 | 11.70 |
| Urethane Resin 2** | 6.09 | 6.09 | 6.09 | 6.79 |
| Neopen Yellow 075 | 2.15 | 2.15 | 2.15 | 2.15 |
| Example I material | 9.78 | — | — | — |
| Example II material | — | 9.78 | — | — |
| Example III material | — | — | 9.78 | — |
| NAUGUARD 445 | 0.18 | 0.18 | 0.18 | 0.20 |
| Total | 100.0 | 100.0 | 100.0 | 100.0 |

*ABITOL E based urethane resin
**glycerol alcohol based urethane resin

The yellow inks thus prepared are printed on HAMMERMILL LASERPRINT® paper (obtained from International Paper, Memphis, Tenn.) in a XEROX® PHASER 850 printer, which uses a printing process wherein the ink is first jetted in an imagewise pattern onto an intermediate transfer member followed by transfer of the imagewise pattern from the intermediate transfer member to a final recording substrate. Solid field images with a resolution of 355 dpi×464 dpi are generated from the printer.

Another type of printed sample is generated on HAMMERMILL LASERPRINT® paper using K Printing Proofer (manufactured by RK Print Coat Instrument Ltd., Litlington, Royston, Herts, U.K.). In this method, the tested inks are melted onto a printing plate set at 150° C. A roller bar fitted with the paper is then rolled over the plate containing the melted ink on its surface. The ink on the paper is cooled, resulting in three separated images of rectangular blocks. The most intensely colored block contains the most ink deposited on the paper, and is therefore used to obtain scratch value measurements. It is believed that the inks of the present invention will be found to have good scratch resistance.

Other embodiments and modifications of the present invention may occur to those of ordinary skill in the art subsequent to a review of the information presented herein; these embodiments and modifications, as well as equivalents thereof, are also included within the scope of this invention.

The recited order of processing elements or sequences, or the use of numbers, letters, or other designations therefor, is not intended to limit a claimed process to any order except as specified in the claim itself.

What is claimed is:
1. An ink composition comprising a colorant and a phase change ink carrier comprising a compound of the formula

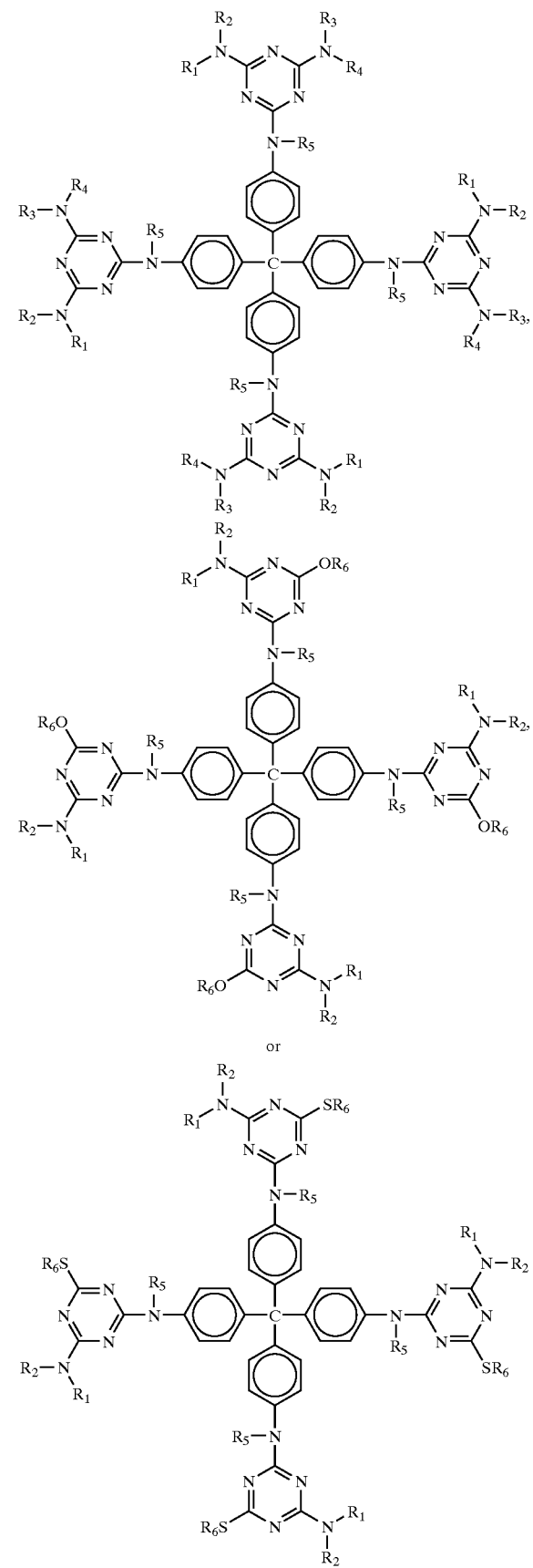

wherein, provided that at least one of $R_1$, $R_2$, $R_3$, $R_4$, $R_5$, and $R_6$ is a hydrogen atom, and provided that at least one of $R_1$, $R_2$, $R_3$, $R_4$, $R_5$, and $R_6$ is not a hydrogen atom, $R_1$, $R_2$, $R_3$, $R_4$, $R_5$, and $R_6$ each, independently of the others, is (i) a hydrogen atom (ii) an alkyl group, (iii) an aryl group, (iv) an arylalkyl group, or (v) on alkylaryl group.

2. An ink composition according to claim 1 wherein the compound of the formula

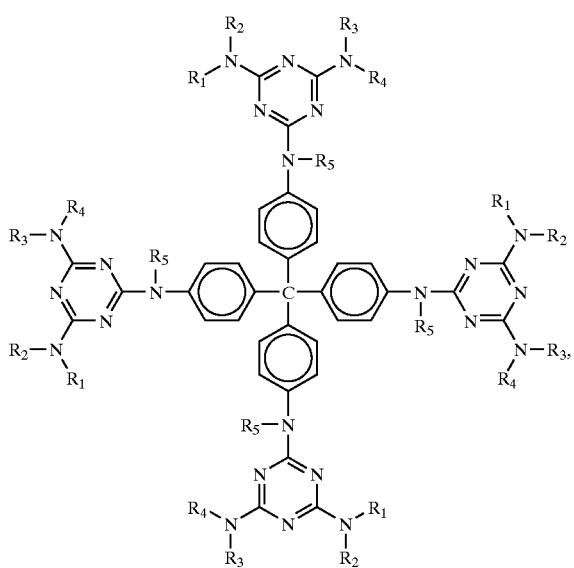

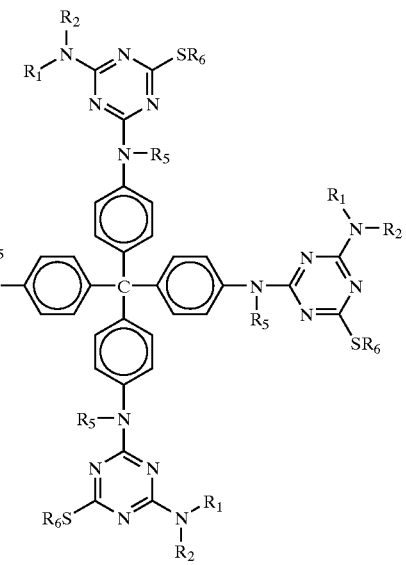

is present in the ink in an amount of at least about 0.1 percent by weight.

3. An ink composition according to claim 1 wherein the compound of the formula

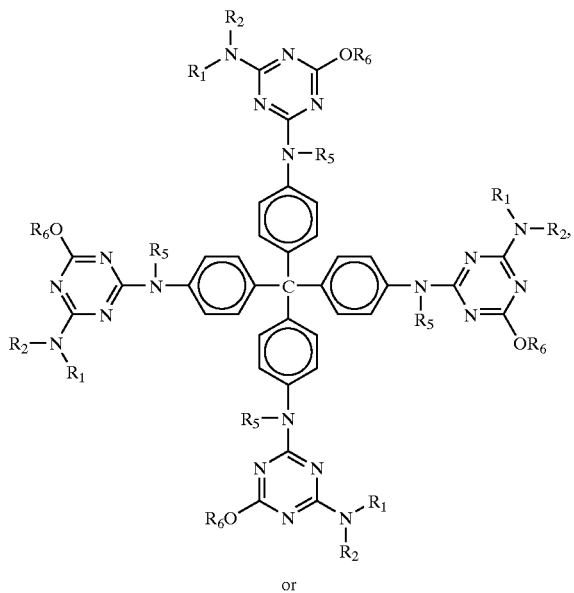

or

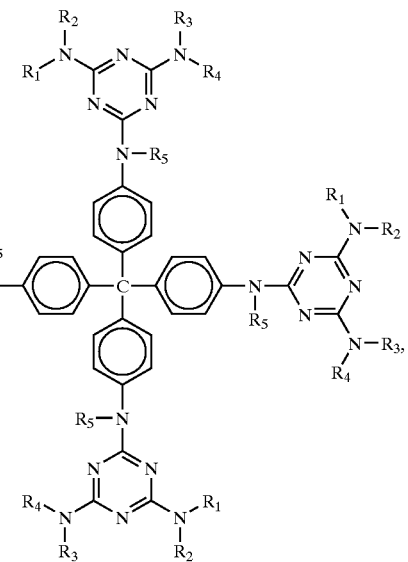

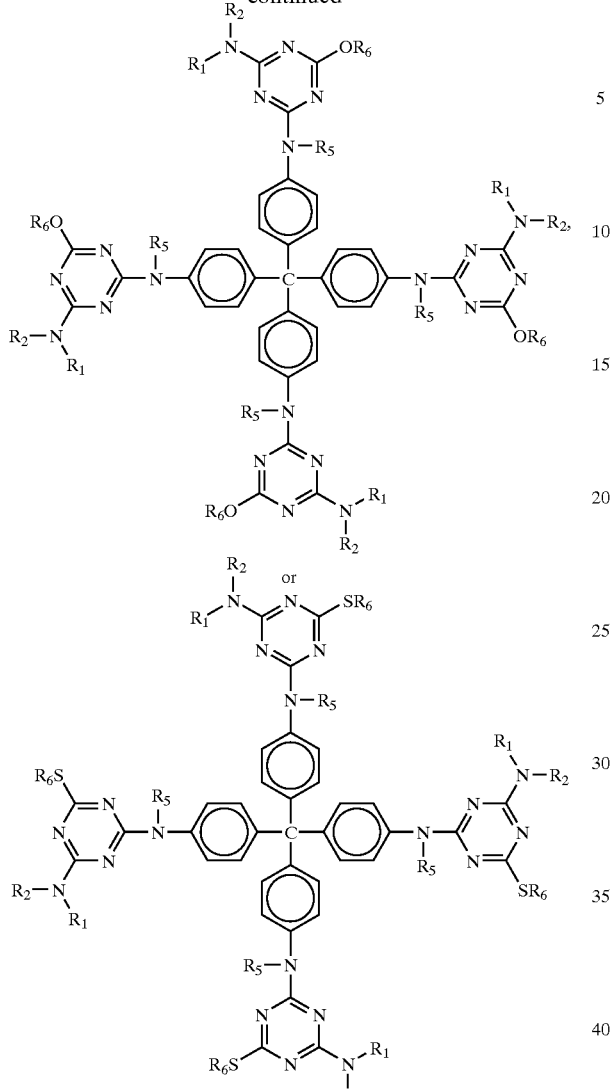
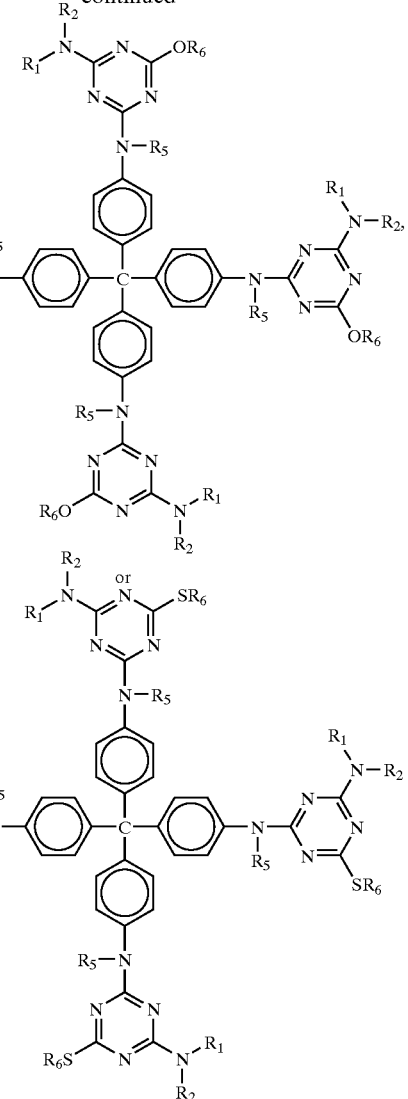
is present in the ink in an amount of at least about 5 percent by weight.
4. An ink composition according to claim 1 wherein the compound of the formula
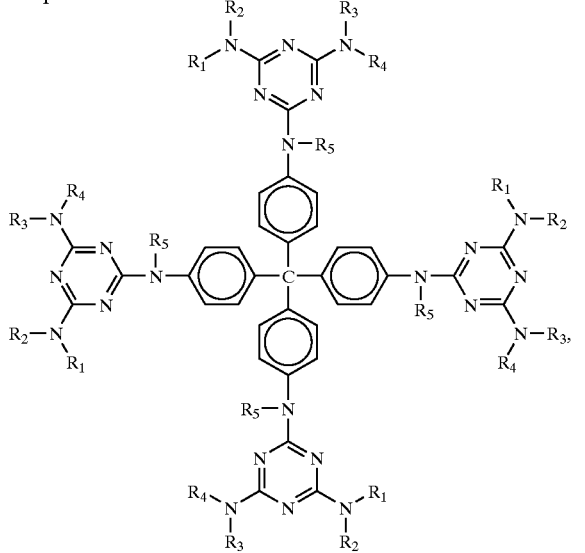
is present in the ink in an amount of no more than about 40 percent by weight.
5. An ink composition according to claim 1 wherein the compound of the formula
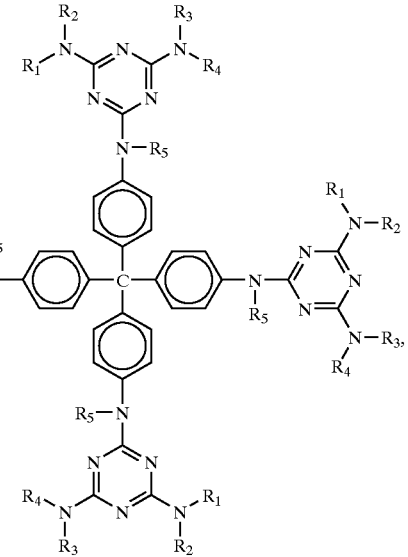

-continued

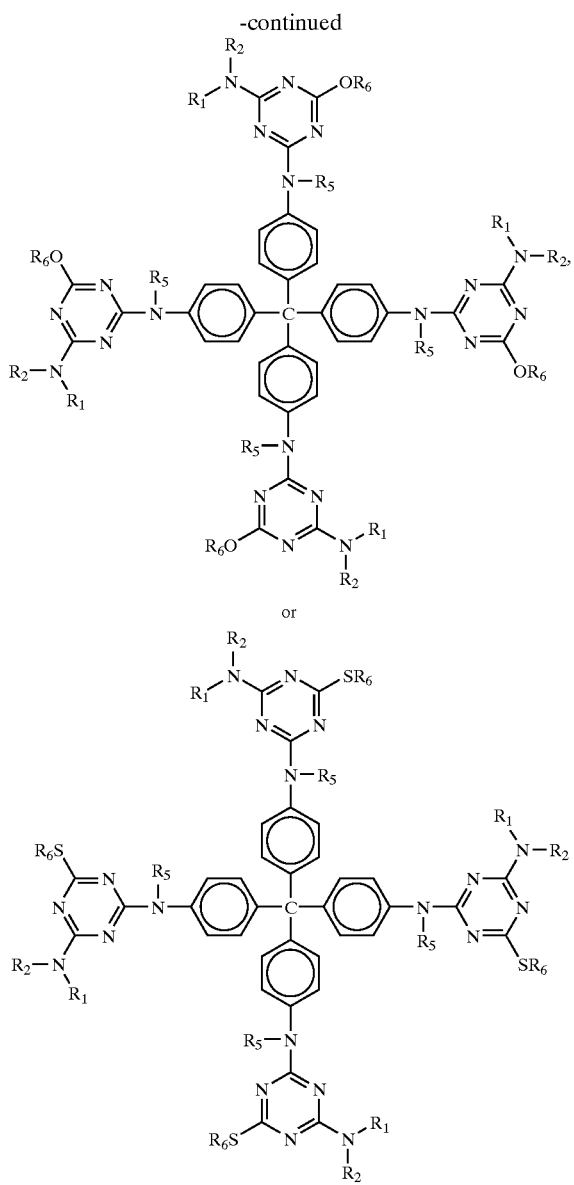

is present in the ink in an amount of no more than about 20 percent by weight.

6. A process which comprises (a) incorporating into an ink jet printing apparatus a phase change ink composition according to claim 1, (b) melting the ink; and (c) causing droplets of the melted ink to be ejected in an imagewise pattern onto a substrate.

7. A process according to claim 6 wherein the printing apparatus employs a piezoelectric printing process wherein droplets of the ink are caused to be ejected in imagewise pattern by oscillations of piezoelectric vibrating elements.

8. A process according to claim 6 wherein the substrate is a final recording sheet and droplets of the melted ink are ejected in an imagewise pattern directly onto the final recording sheet.

9. A process according to claim 6 wherein the substrate is an intermediate transfer member and droplets of the melted ink are ejected in an imagewise pattern onto the intermediate transfer member followed by transfer of the imagewise pattern from the intermediate transfer member to a final recording sheet.

10. A process according to claim 9 wherein the intermediate transfer member is heated to a temperature above that of the final recording sheet and below that of the melted ink in the printing apparatus.

11. An ink according to claim 1 wherein the ink carrier further comprises a monoamide, a tetra-amide, or a mixture thereof.

12. An ink according to claim 1 wherein the ink carrier further comprises (a) stearyl stearamide, (b) a dimer acid based tetra-amide that is the reaction product of dimer acid, ethylene diamine, and stearic acid, or (c) mixtures thereof.

13. An ink according to claim 1 wherein the ink carrier further comprises (a) stearyl stearamide, (b) a dimer acid based tetra-amide that is the reaction product of dimer acid, ethylene diamine, and a carboxylic acid having at least about 36 carbon atoms, or (c) mixtures thereof.

14. An ink according to claim 13 wherein the carboxylic acid has at least about 40 carbon atoms, and wherein the carboxylic acid has no more than about 200 carbon atoms.

15. An ink according to claim 1 wherein the ink carrier further comprises an isocyanate-derived material.

16. An ink according to claim 1 wherein the ink carrier further comprises a urethane isocyanate-derived material, a urea isocyanate-derived material, a urethane/urea isocyanate-derived material, or mixture thereof.

17. An ink according to claim 1 wherein the ink carrier further comprises a mixture of one or more amides and one or more isocyanate-derived materials.

18. An ink according to claim 1 wherein the ink carrier further comprises one or more materials selected from paraffins, microcrystalline waxes, polyethylene waxes, ester waxes, amide waxes, fatty acids, fatty alcohols, fatty amides, sulfonamide materials, tall oil rosins, rosin esters, ethylene/vinyl acetate copolymers, ethylene/acrylic acid copolymers, ethylene/vinyl acetate/acrylic acid copolymers, copolymers of acrylic acid with polyamides, ionomers, and mixtures thereof.

19. An ink according to claim 1 wherein the ink carrier further comprises (a) a polyethylene wax, (b) a stearyl stearamide wax, (c) a dimer acid based tetra-amide that is the reaction product of dimer acid, ethylene diamine, and a carboxylic acid having at least about 36 carbon atoms, (d) a urethane resin derived from the reaction of two equivalents of hydroabietyl alcohol and one equivalent of isophorone diisocyanate, (e) a urethane resin that is the adduct of three equivalents of stearyl isocyanate and a glycerol-based alcohol, and (f) an antioxidant.

20. An ink according to claim 1 wherein the ink carrier is present in the ink in an amount of at least about 0.1 percent by weight of the ink.

21. An ink according to claim 1 wherein the ink carrier is present in the ink in an amount of at least about 50 percent by weight of the ink.

22. An ink according to claim 1 wherein the ink carrier is present in the ink in an amount of at least about 90 percent by weight of the ink.

23. An ink according to claim 1 wherein the ink carrier is present in the ink in an amount of no more than about 99 percent by weight of the ink.

24. An ink according to claim 1 wherein the ink carrier is present in the ink in an amount of no more than about 98 percent by weight of the ink.

25. An ink according to claim 1 wherein the ink carrier is present in the ink in an amount of no more than about 95 percent by weight of the ink.

26. An ink according to claim 1 wherein the colorant is present in the ink in an amount of at least about 0.1 percent by weight of the ink.

27. An ink according to claim 1 wherein the colorant is present in the ink in an amount of at least about 0.5 percent by weight of the ink.

28. An ink according to claim 1 wherein the colorant is present in the ink in an amount of at least about 2 percent by weight of the ink.

29. An ink according to claim 1 wherein the colorant is present in the ink in an amount of no more than about 15 percent by weight of the ink.

30. An ink according to claim 1 wherein the colorant is present in the ink in an amount of no more than about 8 percent by weight of the ink.

31. An ink according to claim 1 wherein the colorant is present in the ink in an amount of no more than about 6 percent by weight of the ink.

32. An ink according to claim 1 wherein the ink further comprises a liquid component that, in its pure form, is in a liquid state at room temperature, but, when incorporated into the ink, enables the ink to be a solid at 35° C. or higher.

33. An ink according to claim 32 wherein the liquid component is an aliphatic hydrocarbon, a glycol ether, an ester, an amide, an alcohol, or a mixture thereof.

34. An ink according to claim 32 wherein the liquid component is squalene, butyl carbitol, tripropylene glycol monomethyl ether, 1-phenoxy-2-propanol, dibutyl phthalate, dibutyl sebacate, 1-dodecanol, or mixtures thereof.

35. An ink according to claim 1 wherein the ink is a solid at temperatures of about 35° C. and lower.

36. An ink according to claim 1 wherein the ink is a solid at temperatures of about 50° C. and lower.

37. An ink according to claim 1 wherein the ink is a solid at temperatures of about 70° C. and lower.

38. An ink according to claim 1 wherein the ink has a viscosity at jetting temperatures of no more than about 30 centipoise.

39. An ink according to claim 1 wherein the ink has a viscosity at jetting temperatures of no more than about 20 centipoise.

40. An ink according to claim 1 wherein the ink has a viscosity at jetting temperatures of no more than about 15 centipoise.

41. An ink according to claim 1 wherein the ink has a viscosity at jetting temperatures of no less than about 2 centipoise.

42. An ink according to claim 1 wherein the ink has a viscosity at jetting temperatures of no less than about 5 centipoise.

43. An ink according to claim 1 wherein the ink has a viscosity at jetting temperatures of no less than about 7 centipoise.

44. An ink composition according to claim 1 wherein the compound of the formula

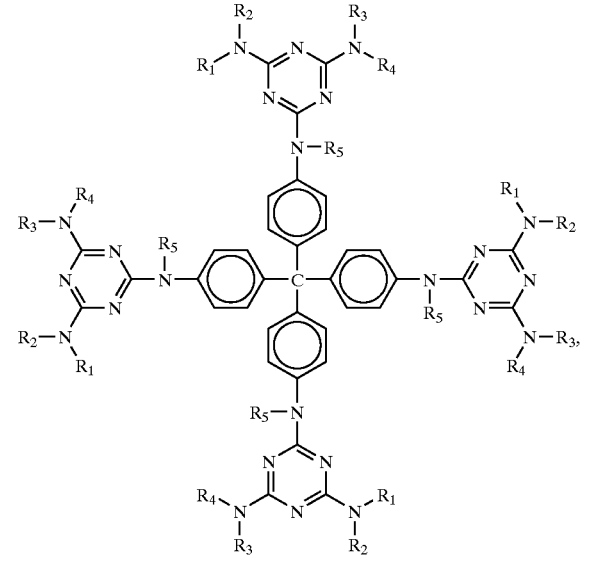

is present in the ink in an amount at least about 1 percent by weight.

45. An ink composition according to claim 1 wherein the compound of the formula

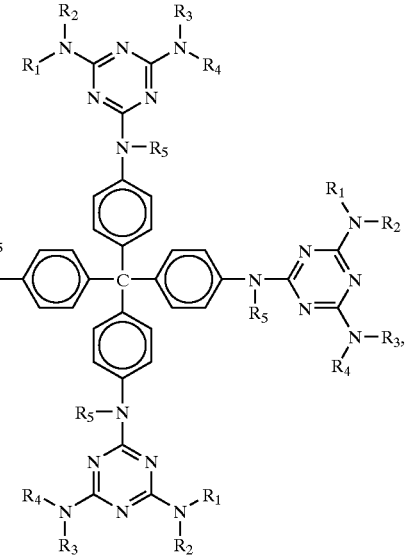

-continued
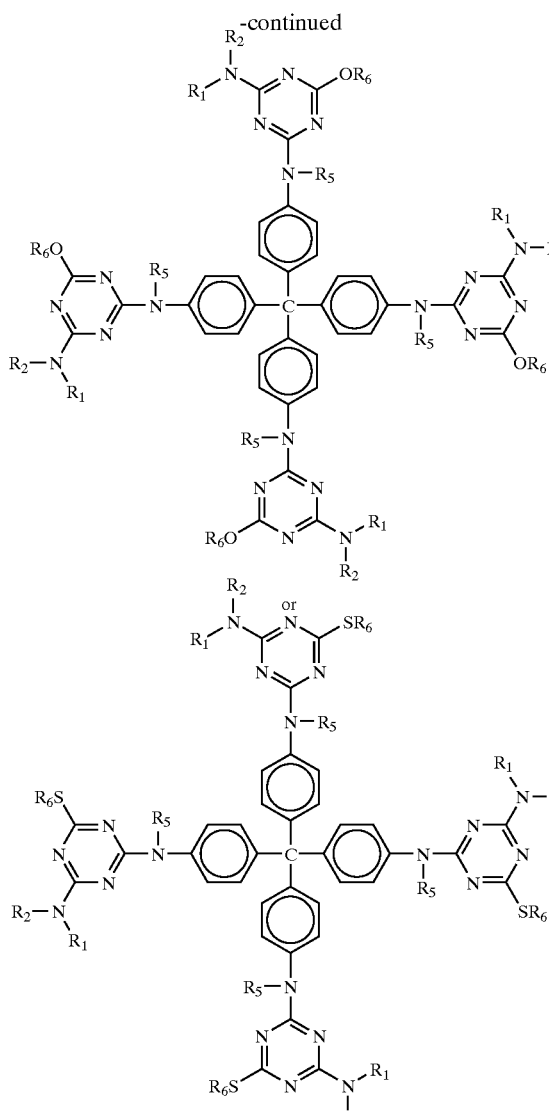
is present in the ink in an amount at least about 10 percent by weight.
46. An ink composition according to claim 1 wherein the compound of the formula
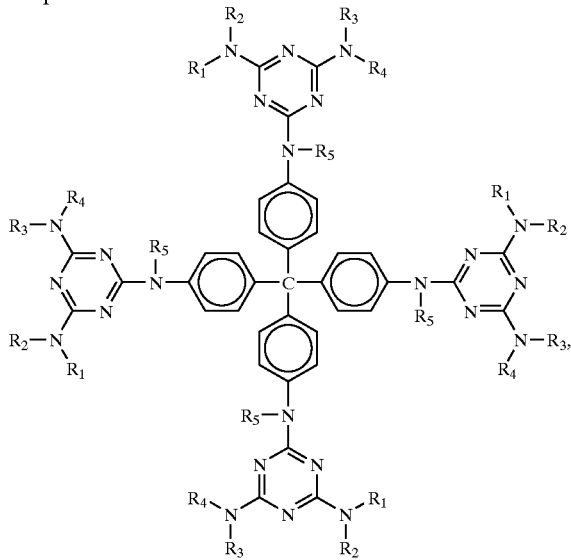
-continued
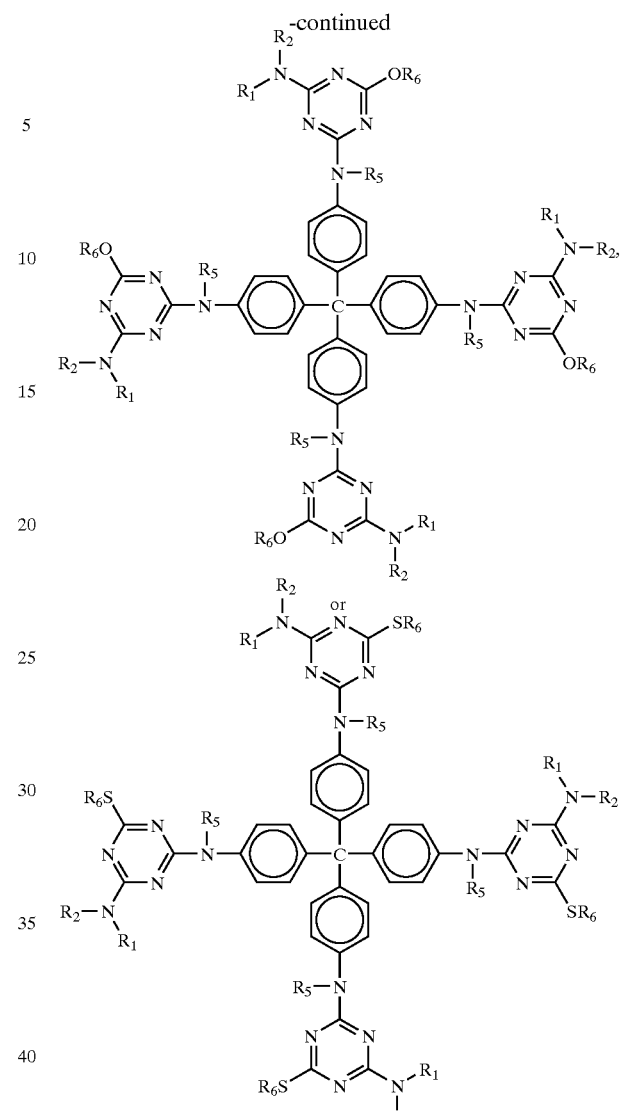
is present in the ink in an amount of no more than about 25 percent by weight.
47. An ink composition according to claim 1 wherein the compound of the formula
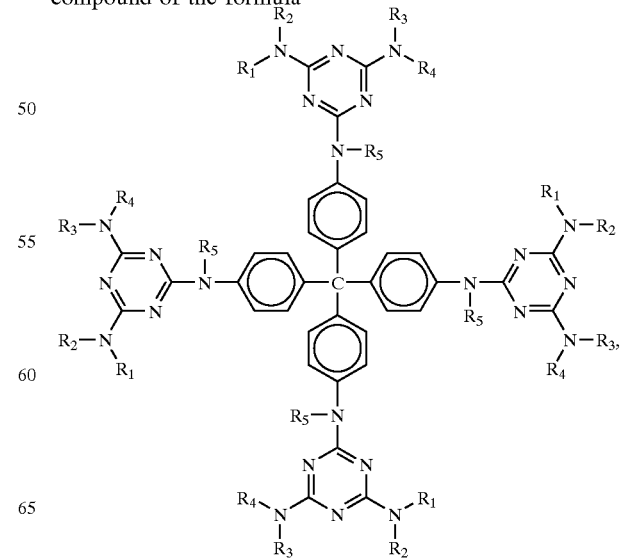

-continued

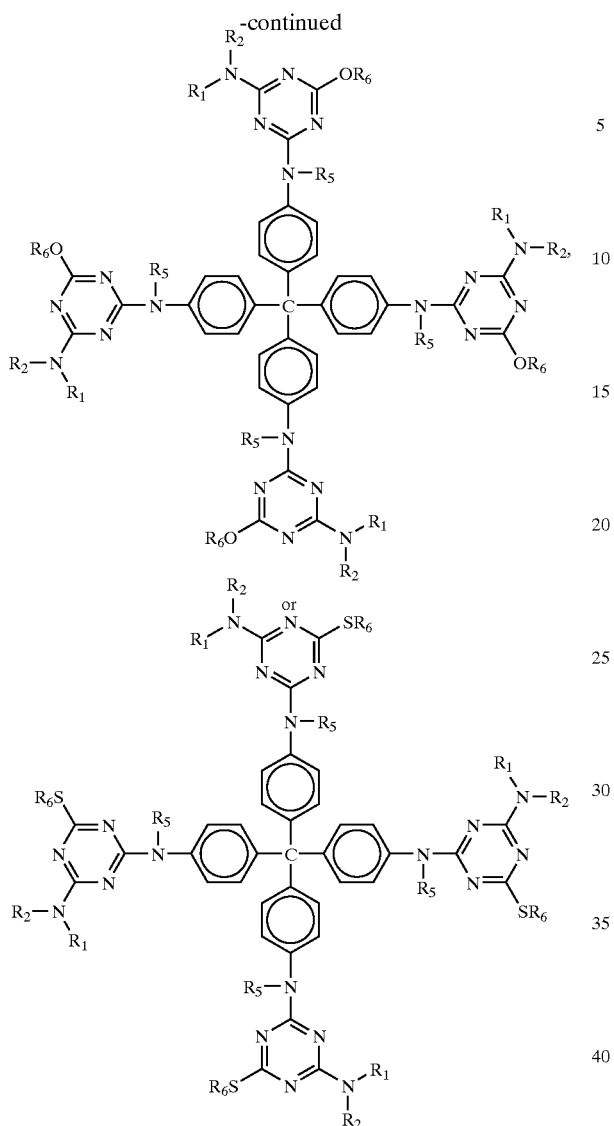

is present in the ink in an amount of no more than about 15 percent by weight.

48. An ink composition according to claim 1 wherein the compound is of the formula

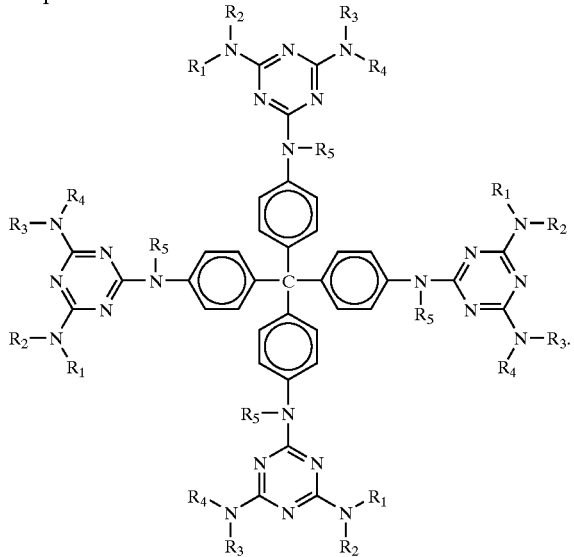

49. An ink composition according to claim 1 wherein the compound is of the formula

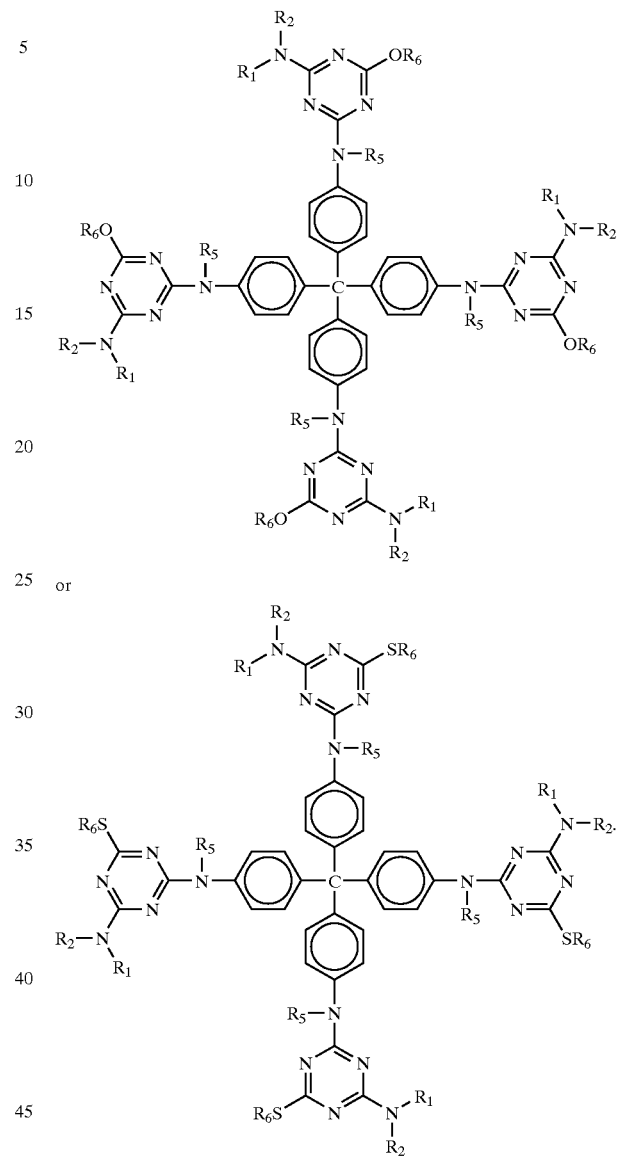

50. An ink composition according to claim 1 wherein, provided that at least one of $R_1$, $R_2$, $R_3$, $R_4$, $R_5$, and $R_6$ is a hydrogen atom, and provided that at least one of $R_1$, $R_2$, $R_3$, $R_4$, $R_5$, and $R_6$ is not a hydrogen atom, $R_1$, $R_2$, $R_3$, $R_4$, $R_5$, and $R_6$ each, independently of the others, is (i) a hydrogen atom, (ii) an alkyl group having at least 1 carbon atom and having no more than about 96 carbon atoms, (iii) an aryl group having at least about 6 carbon atoms and having no more than about 50 carbon atoms, (iv) an arylalkyl group having at least about 7 carbon atoms and having no more than about 96 carbon atoms, or (v) an alkylaryl group having at least about 7 carbon atoms and having no more than about 96 carbon atoms.

51. An ink composition according to claim 1 wherein at least one of $R_1$, $R_2$, $R_3$, $R_4$, $R_5$, and $R_6$ is an unsubstituted alkyl group, an unsubstituted aryl group, an unsubstituted arylalkyl group, or an unsubstituted alkylaryl group.

52. An ink composition according to claim 1 wherein at least one of $R_1$, $R_2$, $R_3$, $R_4$, $R_5$, and $R_6$ is a substituted alkyl group, a substituted aryl group, a substituted arylalkyl group, or a substituted alkylaryl group.

53. An ink composition according to claim 52 wherein the substituents are hydroxy groups, halogen atoms, amine groups, imine groups, ammonium groups, pyridine groups, pyridinium groups, ether groups, aldehyde groups, ester groups, amide groups, carbonyl groups, thiocarbonyl groups, sulfate groups, sulfonate groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, azo groups, cyanato groups, isocyanato groups, thiocyanato groups, isothiocyanato groups, alkoxy groups, aryloxy groups, arylalkyloxy groups, alkylaryloxy groups, polyalkyleneoxy groups wherein the alkyl portion of the repeat alkyleneoxy groups has from about 1 to about 12 carbon atoms and wherein the number of repeat alkyleneoxy groups is from about 2 to about 50, polyaryleneoxy groups wherein the aryl portion of the repeat aryleneoxy groups has from about 6 to about 14 carbon atoms and wherein the number of repeat aryleneoxy groups is from about 2 to about 20, polyarylalkyleneoxy groups wherein the arylalkyl portion of the repeat arylalkyleneoxy groups has from about 7 to about 50 carbon atoms and wherein the number of repeat arylalkyleneoxy groups is from about 2 to about 20, polyalkylaryleneoxy group wherein the alkylaryl portion of the repeat alkylaryleneoxy groups has from about 7 to about 50 carbon atoms and wherein the number of repeat alkylaryleneoxy groups is from about 2 to about 20, silyl groups, siloxane groups, polysilylene groups with from 2 to about 100 repeat silylene units, polysiloxane groups with from 2 to about 200 repeat siloxane units, or mixtures thereof, wherein two or more substituents can be joined together to form a ring.

54. An ink composition according to claim 1 wherein $R_1$, $R_2$, $R_3$, and $R_4$ each, independently of the others, is methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, or eicosyl.

55. An ink composition according to claim 1 wherein $R_5$ is hydrogen.

56. An ink composition according to claim 1 wherein $R_6$ is hydrogen, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl,

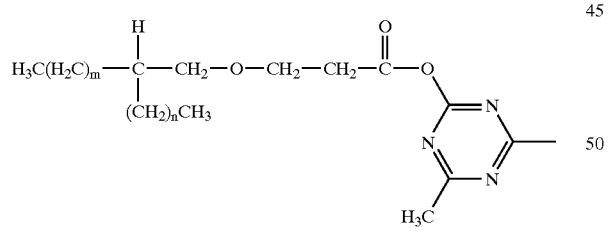

wherein m and n each represent numbers of repeat —$CH_2$— groups and each, independently of the other, is from 1 to about 40,

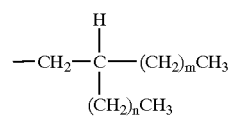

wherein m and n each represent numbers of repeat —$CH_2$— groups and each, independently of the other, is from 1 to about 40,

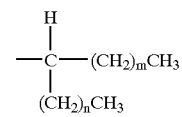

wherein m and n each represent numbers of repeat —$CH_2$— groups and each, independently of the other, is from 1 to about 40,

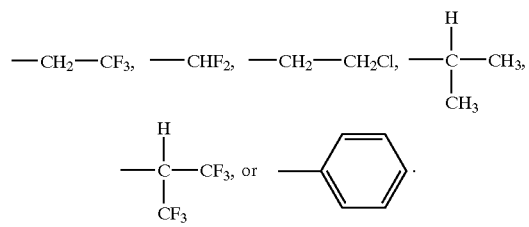

57. An ink composition according to claim 1 wherein the compound is of the formula

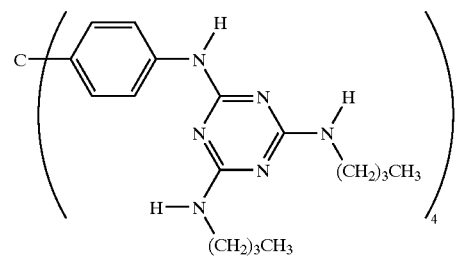

58. An ink composition according to claim 1 wherein the compound is of the formula

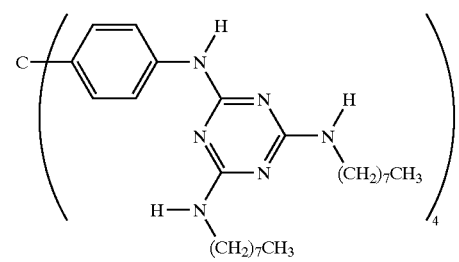

59. An ink composition according to claim 1 wherein the compound is of the formula

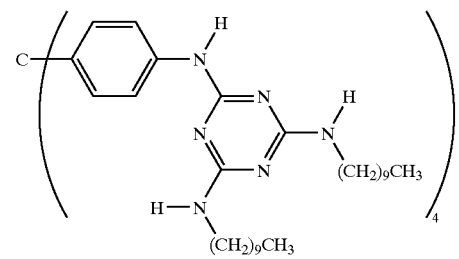

60. An ink composition according to claim 1 wherein the compound is of the formula

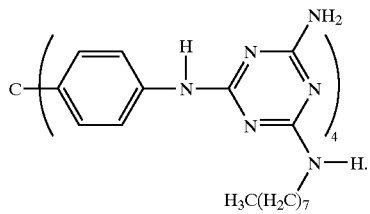

61. An ink composition according to claim 1 wherein the compound is of the formula

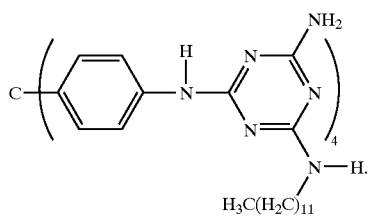

62. An ink composition according to claim 1 wherein the compound is of the formula

63. An ink composition according to claim 1 wherein the compound is of the formula

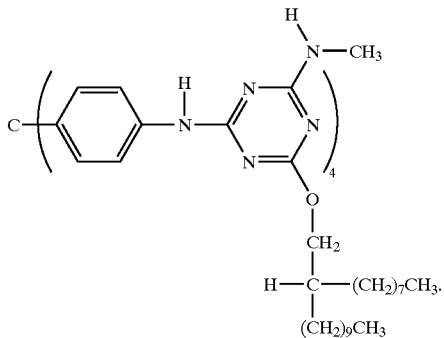

63. An ink composition according to claim 1 wherein the compound is of the formula

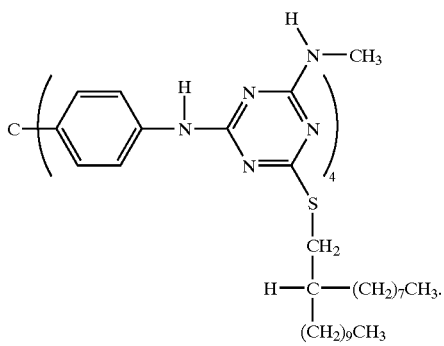

* * * * *